United States Patent [19]
Klieman et al.

[11] Patent Number: 5,792,165
[45] Date of Patent: Aug. 11, 1998

[54] ENDOSCOPIC INSTRUMENT WITH DETACHABLE END EFFECTOR

[75] Inventors: Charles H. Klieman, 79 Cypress Way, Rolling Hills Estates, Calif. 90274; John M. Stiggelbout, Sausalito; Bruce M. Schena, Menlo Park, both of Calif.

[73] Assignee: Charles H. Klieman, Rolling Hills Estates, Calif.

[21] Appl. No.: 471,988

[22] Filed: Jun. 6, 1995

Related U.S. Application Data

[63] Continuation-in-part of Ser. No. 320,941, Oct. 11, 1994, Pat. No. 5,582,617, which is a continuation-in-part of Ser. No. 295,352, Aug. 24, 1994, abandoned, which is a continuation of Ser. No. 95,739, Jul. 21, 1993, abandoned.

[51] Int. Cl.$^6$ .................... A61B 17/28; A61B 17/32
[52] U.S. Cl. .................... 606/170; 606/205; 606/174
[58] Field of Search .................... 606/205–208, 606/174, 170; 128/751

[56] References Cited

U.S. PATENT DOCUMENTS

| | | |
|---|---|---|
| 3,730,185 | 5/1973 | Cook et al. |
| 3,888,004 | 6/1975 | Coleman |
| 4,258,716 | 3/1981 | Sutherland |
| 4,320,761 | 3/1982 | Haddad |
| 4,672,964 | 6/1987 | Dee et al. |
| 4,688,555 | 8/1987 | Wardle |
| 4,763,669 | 8/1988 | Jaeger |
| 4,838,853 | 6/1989 | Parisi |
| 4,861,332 | 8/1989 | Parisi |
| 4,872,456 | 10/1989 | Hasson |
| 4,877,026 | 10/1989 | de Laforcade |
| 4,880,015 | 11/1989 | Nierman |
| 4,940,468 | 7/1990 | Petillo |
| 4,978,333 | 12/1990 | Broadwin et al. |
| 4,986,825 | 1/1991 | Bays et al. |
| 5,024,652 | 6/1991 | Dumenek et al. |
| 5,026,387 | 6/1991 | Thomas |
| 5,112,299 | 5/1992 | Pasaloff |
| 5,133,736 | 7/1992 | Bales, Jr. et al. |
| 5,174,300 | 12/1992 | Bales et al. |
| 5,176,697 | 1/1993 | Hasson et al. |
| 5,209,747 | 5/1993 | Knoepfler |
| 5,224,954 | 7/1993 | Watts et al. |
| 5,254,130 | 10/1993 | Poncet et al. |

(List continued on next page.)

FOREIGN PATENT DOCUMENTS

| | | |
|---|---|---|
| 0 577 423 A2 | 1/1994 | European Pat. Off. |
| 2681775-A1 | 4/1993 | France |
| 43 00 307 A1 | 7/1994 | Germany |
| 43 07 539 A1 | 9/1994 | Germany |
| 980-703-A | 12/1982 | U.S.S.R. |
| WO 91/02493 | 3/1991 | WIPO |
| WO 93/07816 | 4/1993 | WIPO |
| WO 94/20034 | 9/1994 | WIPO |

OTHER PUBLICATIONS

Hospital Price List, effective Feb. 24, 1992, published by Ethicon, a Johnson & Johnson Company.

Advertisement dated May of 1992 for Auto–Sector TM published by Omni–Tract Surgical.

*Primary Examiner*—Michael H. Thaler
*Attorney, Agent, or Firm*—Fish & Richardson P.C., P.A.

[57] ABSTRACT

A surgical instrument having a handle, barrel and detachable end effector is provided. The barrel is generally tubular, with one end being connected to the handle. The end effector is releasably attached to the other end of the barrel, with jaws which may be pivoted, rotated and operated independently through multiple linkage members connected to a motive power source housed in or attached to the handle. The instrument is operated and controlled by a microprocessor and multidimensional controller or electrical contacts included in the handle. In the preferred embodiment, closing of jaws is manual with locking means; also, the end effector is scissor-like, but other end effectors such as graspers, clamps, dissectors or needle drivers, with appropriate operating and linkage members, may be attached to the handle.

38 Claims, 47 Drawing Sheets

U.S. PATENT DOCUMENTS

| | | |
|---|---|---|
| 5,258,007 | 11/1993 | Spetzler et al. . |
| 5,275,615 | 1/1994 | Rose . |
| 5,281,220 | 1/1994 | Blake, III . |
| 5,282,806 | 2/1994 | Haber et al. . |
| 5,282,807 | 2/1994 | Knoepfler . |
| 5,282,826 | 2/1994 | Quadri . |
| 5,300,081 | 4/1994 | Young et al. . |
| 5,308,358 | 5/1994 | Bond et al. . |
| 5,314,445 | 5/1994 | Heidmueller née Degwitz et al. . |
| 5,318,589 | 6/1994 | Lichman . |
| 5,330,502 | 7/1994 | Hassler et al. . |
| 5,350,355 | 9/1994 | Sklar . |
| 5,350,391 | 9/1994 | Iacovelli . |
| 5,368,606 | 11/1994 | Marlow et al. . |
| 5,374,277 | 12/1994 | Hassler . |
| 5,383,888 | 1/1995 | Zvenyatsky et al. . |
| 5,403,342 | 4/1995 | Tovey et al. . |

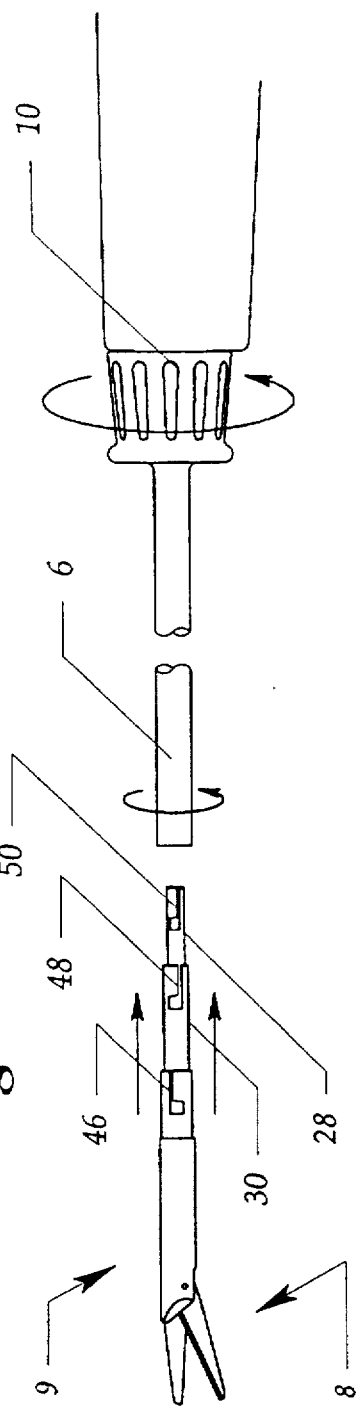
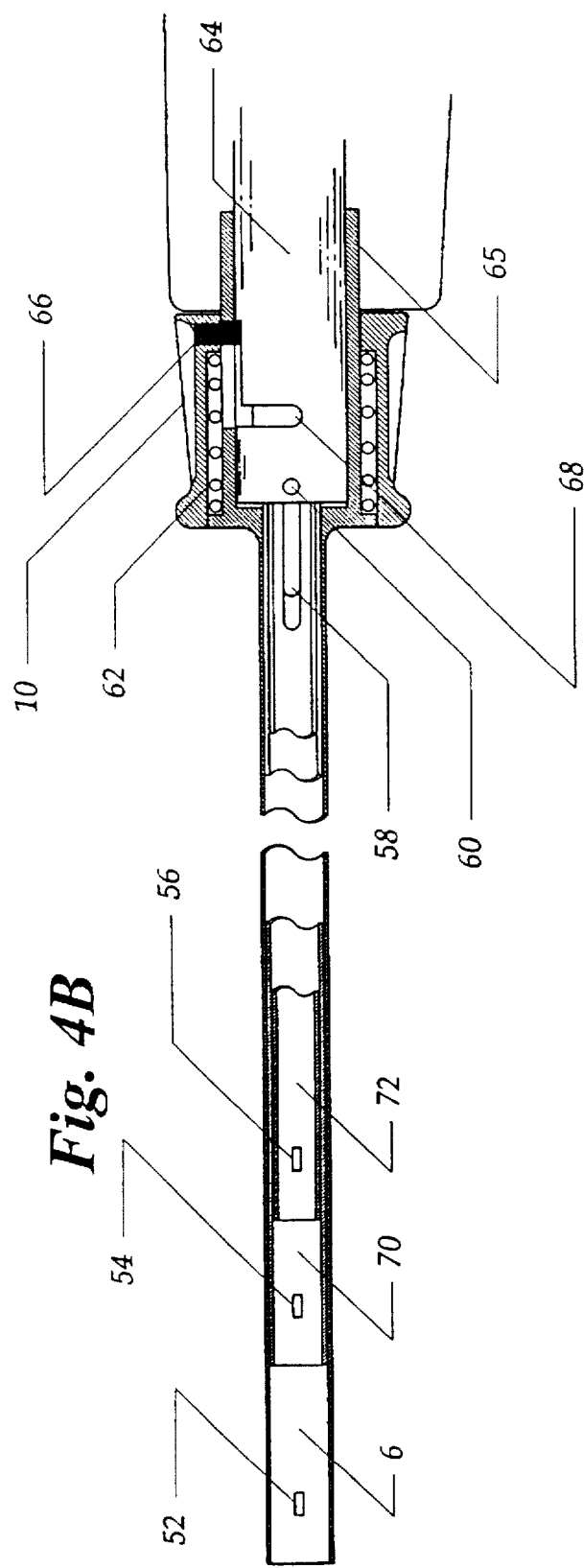
Fig. 4A
Fig. 4B

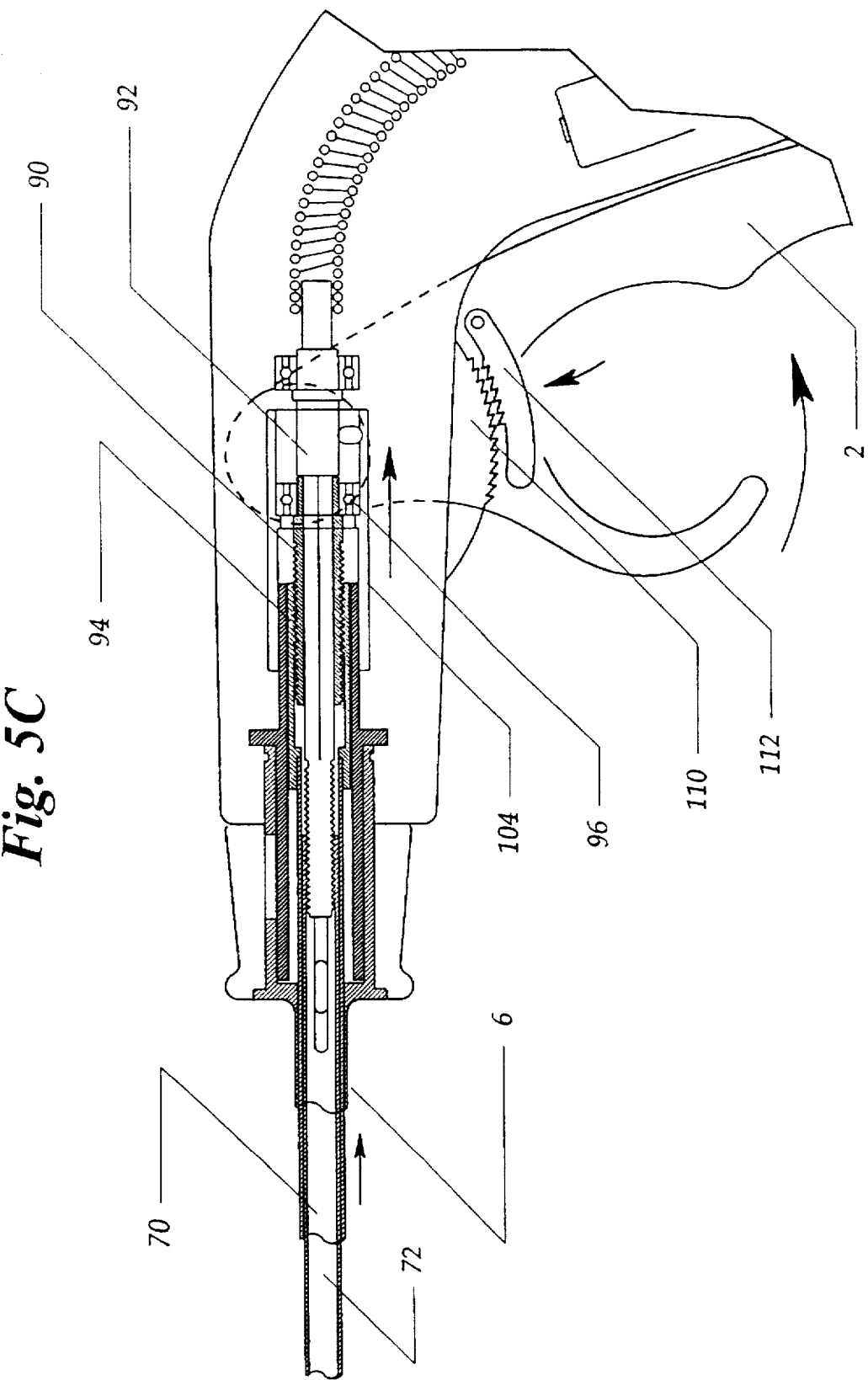

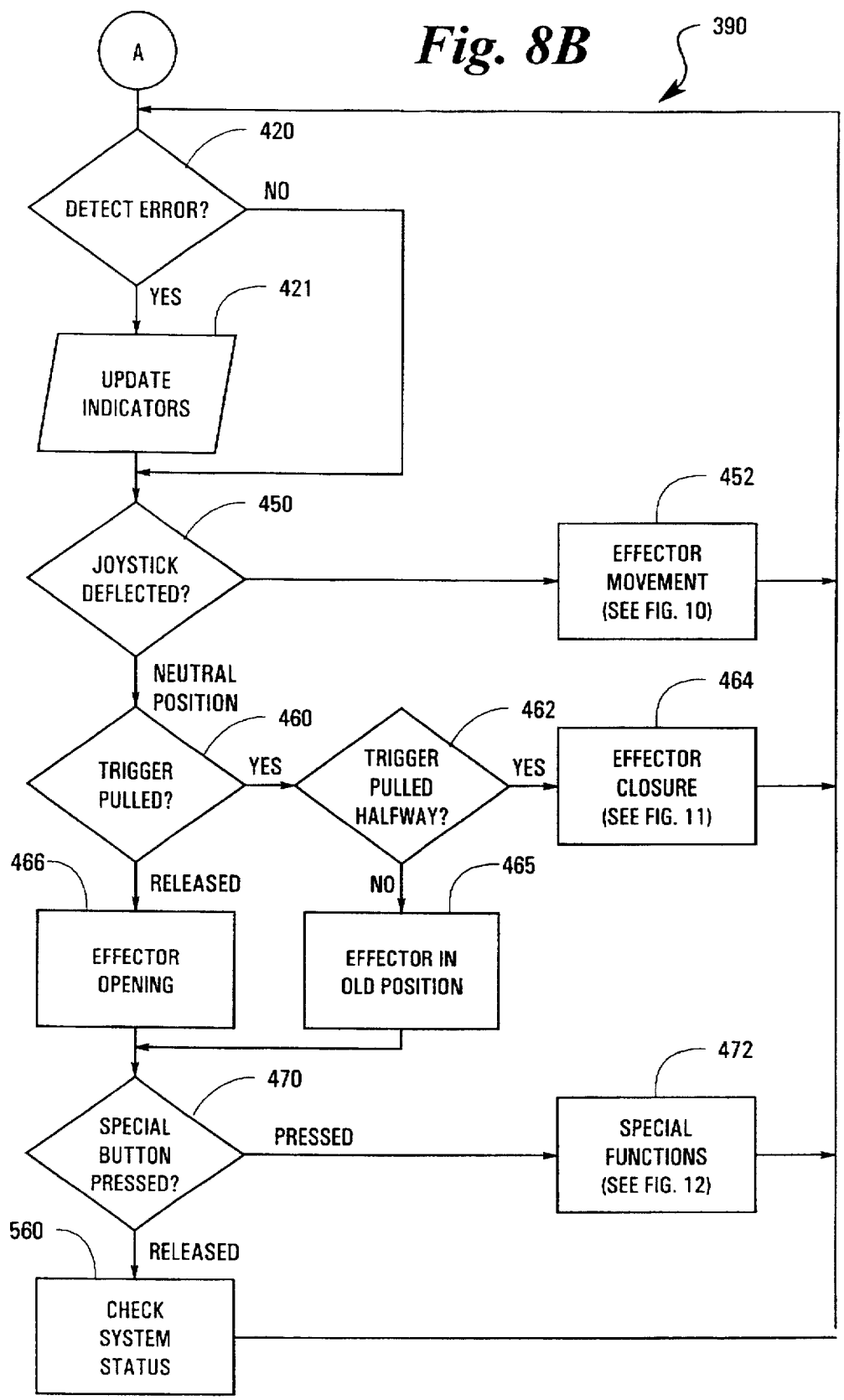

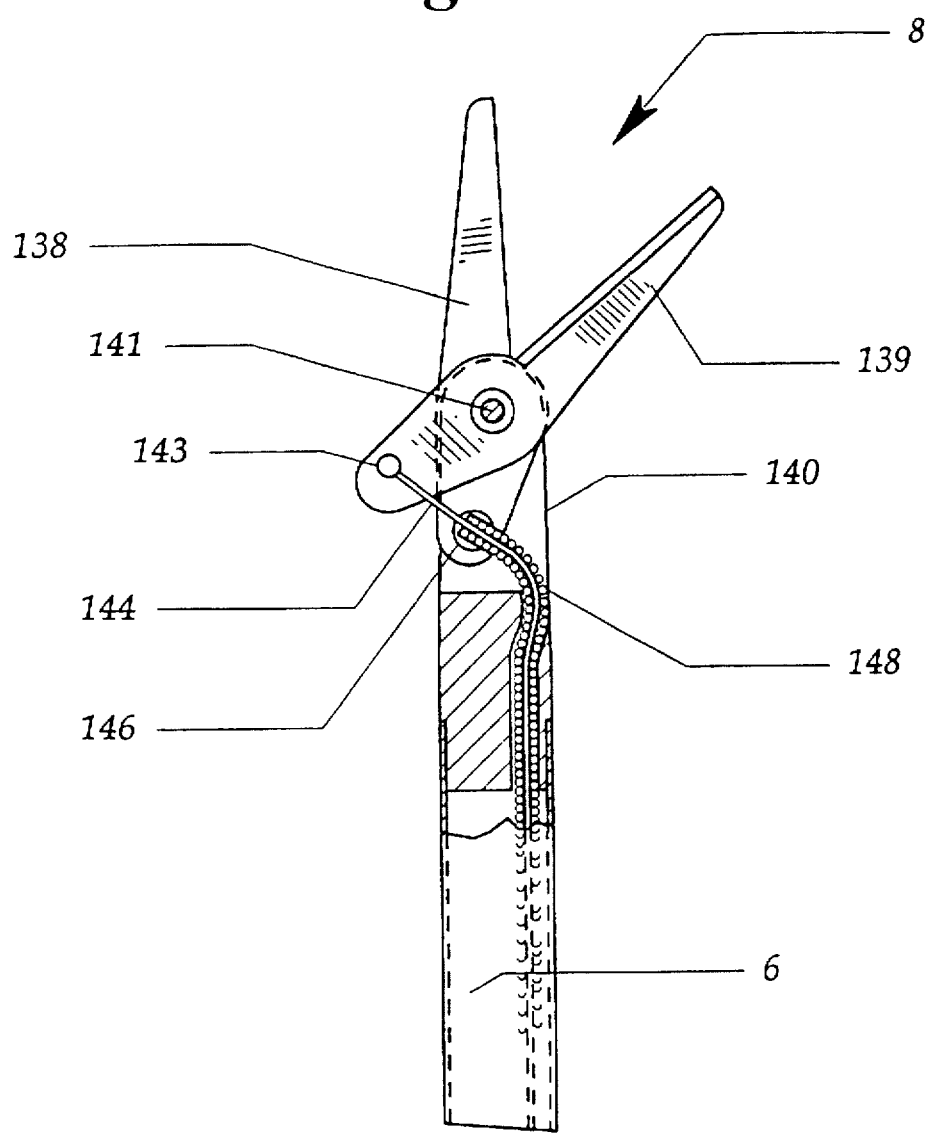

Fig. 24A
Fig. 24B
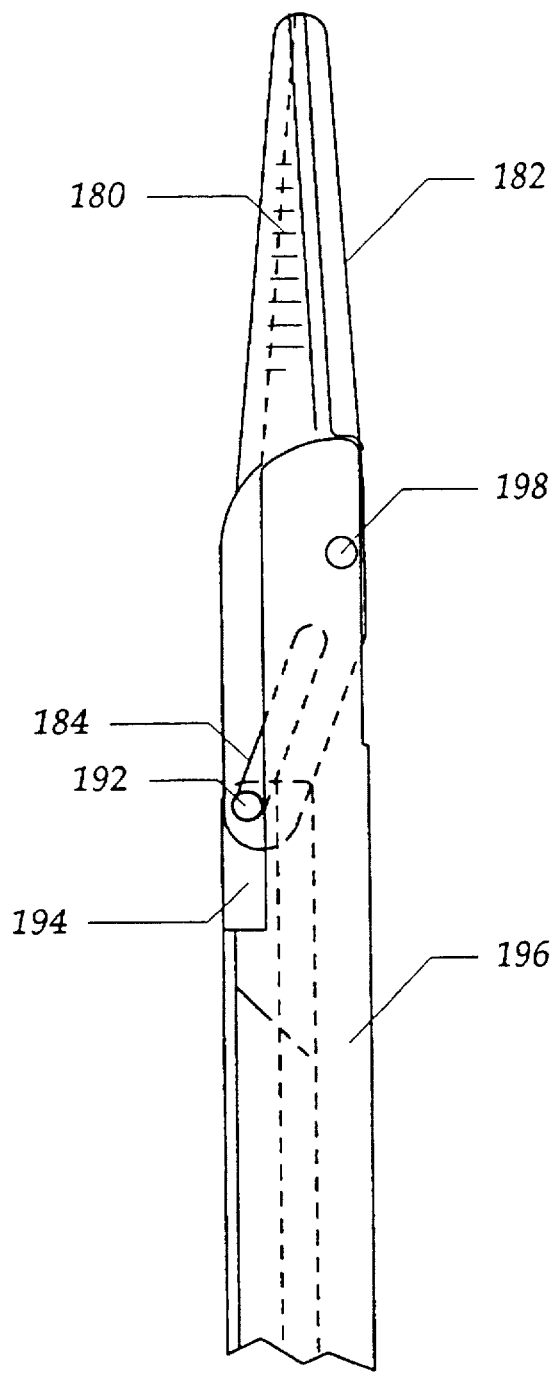
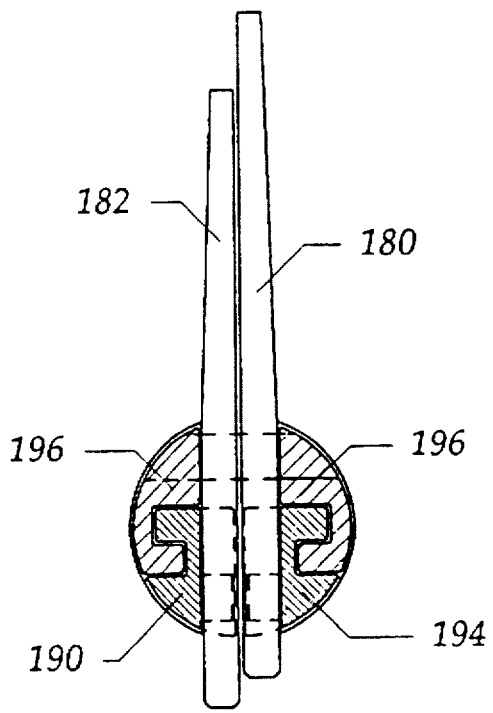

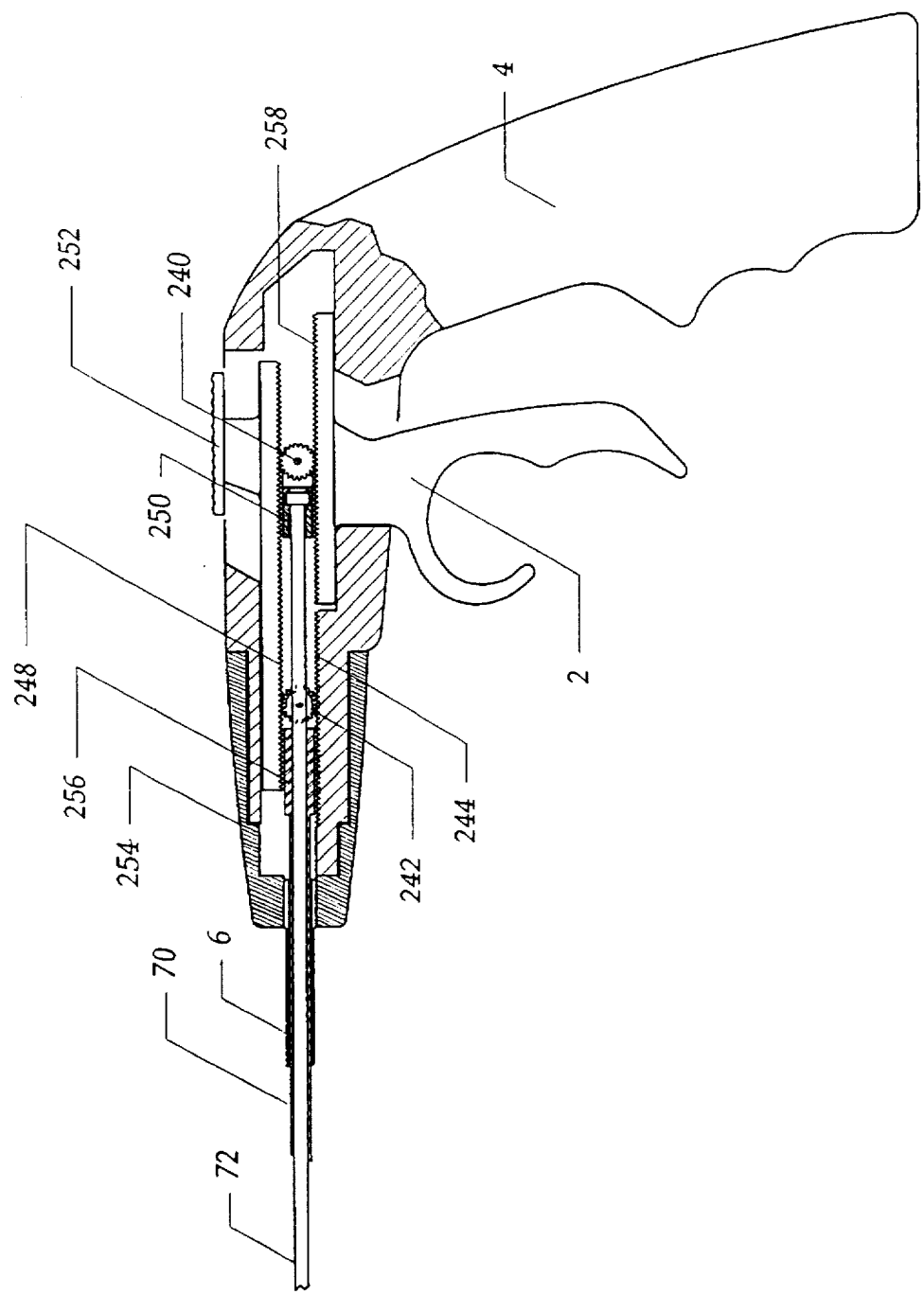

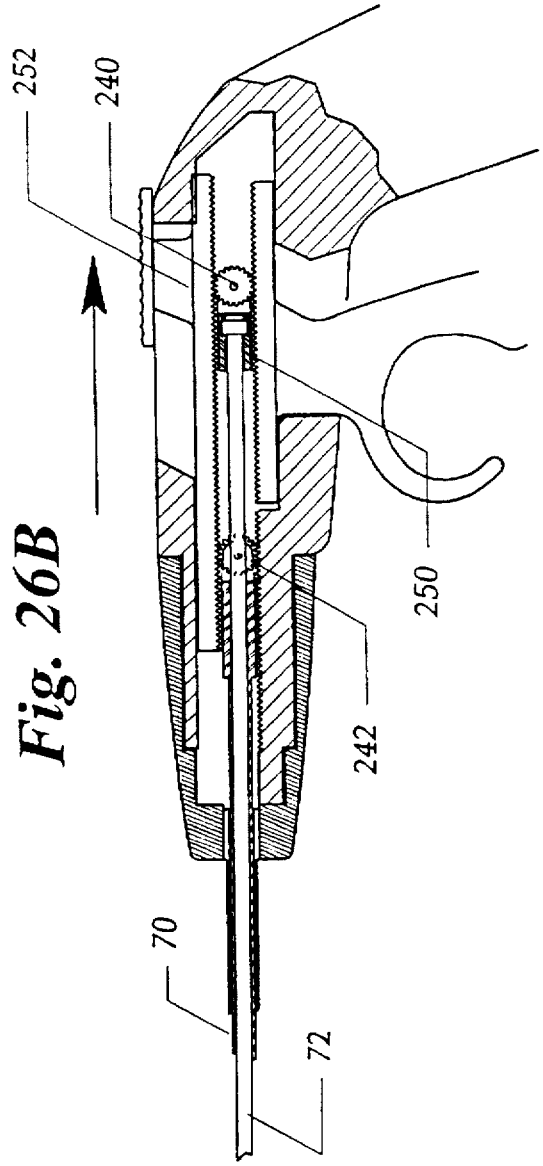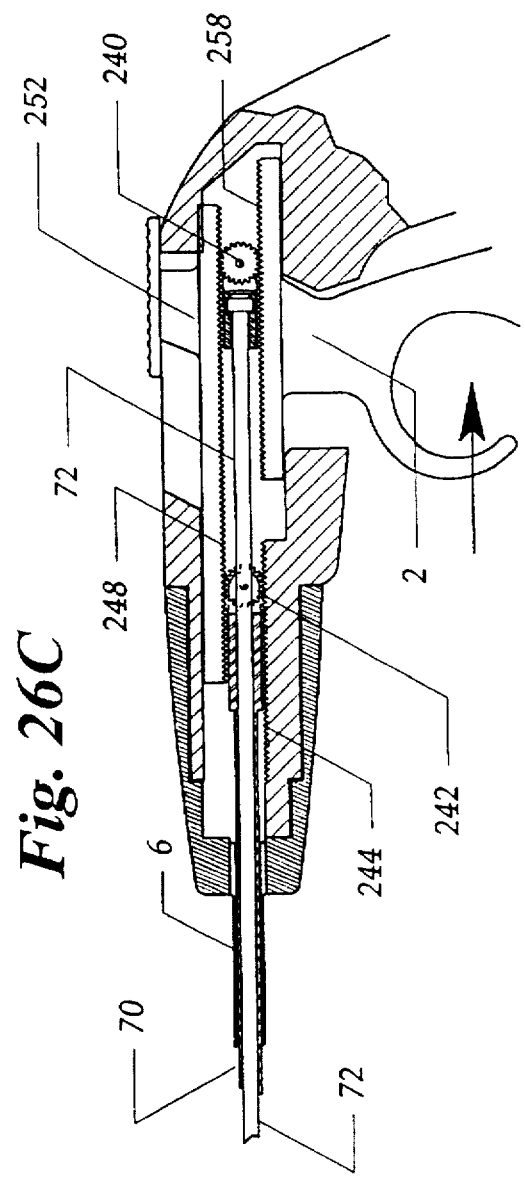

*Fig. 27B* *Fig. 27C*
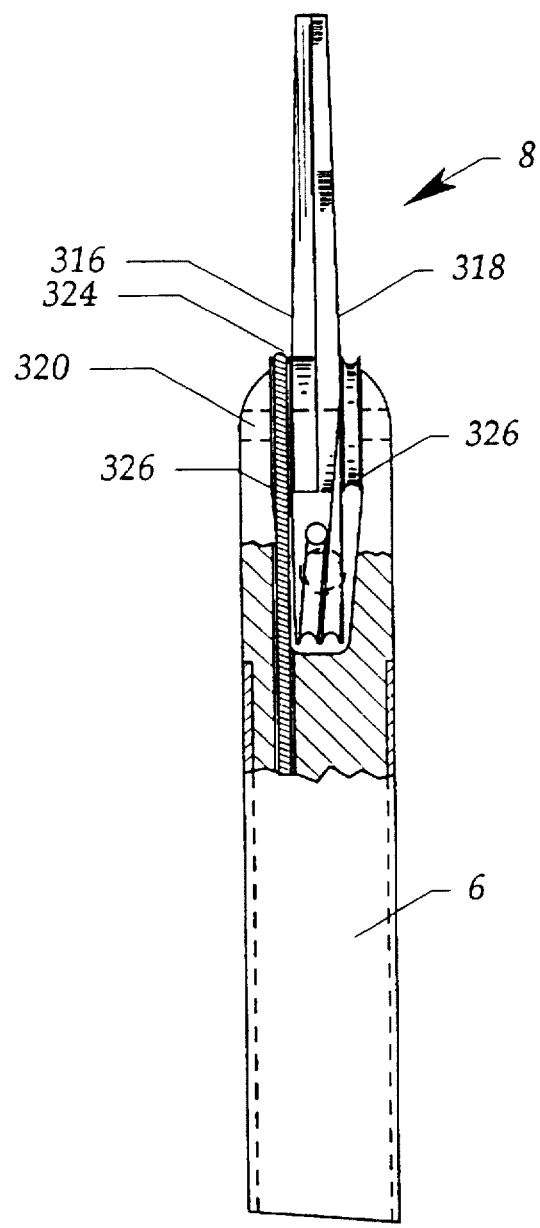 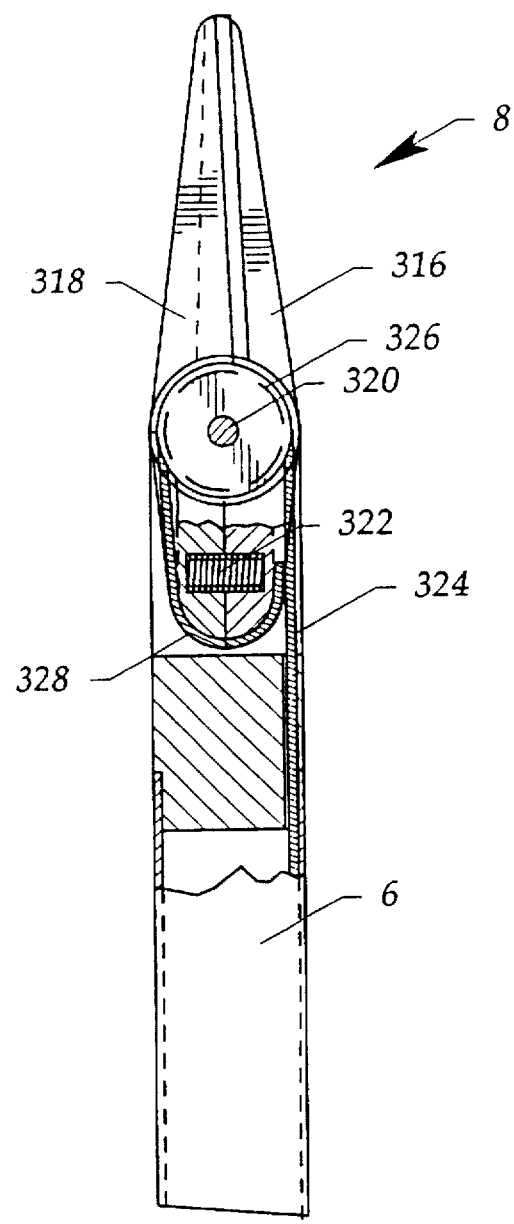

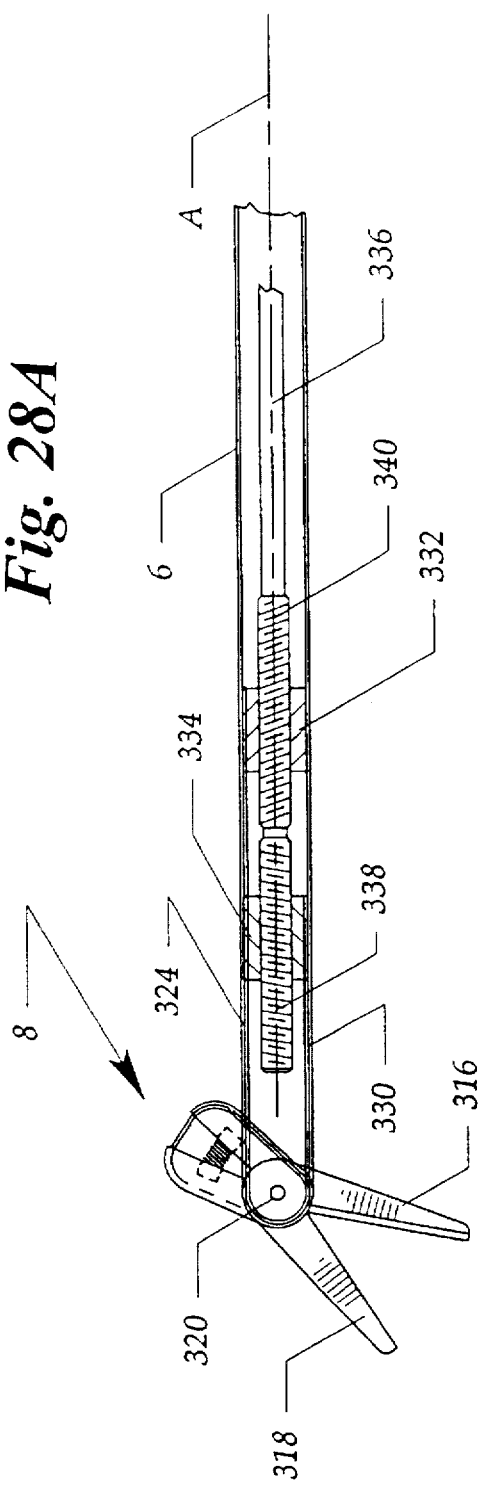
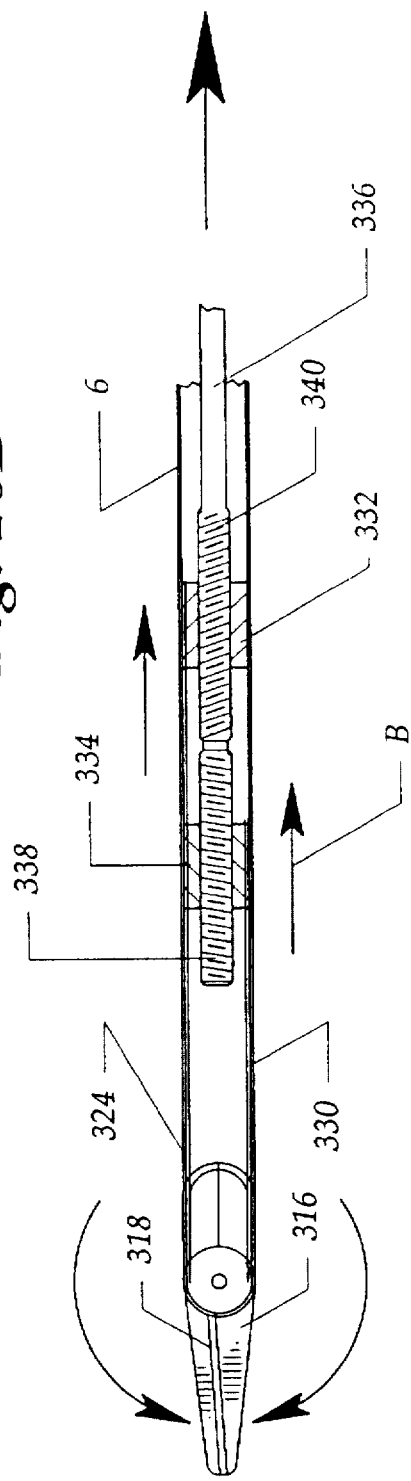
Fig. 28A
Fig. 28B

ENDOSCOPIC INSTRUMENT WITH DETACHABLE END EFFECTOR

RELATED APPLICATIONS

This application is a continuation-in-part of application Ser. No. 08/320,941, filed Oct. 11, 1994, now U.S. Pat. No. 5,582,617, which is a continuation-in-part of application Ser. No. 08/295,352, filed Aug. 24, 1994, now abandoned which is a continuation of application Ser. No. 08/095,739, filed Jul. 21, 1993 and now abandoned.

TECHNICAL FIELD

The present invention relates generally to the field of surgical instruments. In particular, it relates to a surgical instrument for use in endoscopic surgical procedures, wherein the instrument, especially the end effector carried thereby, may be positioned and operated with one hand.

BACKGROUND OF THE INVENTION

Endoscopy (e.g., laparoscopy, thoracoscopy, arthroscopy, etc.) is a form of surgery that involves visualizing the interior of the body using an illuminating optical instrument, an endoscope, and the performance of an operative procedure using surgical instruments. The endoscope and other surgical instruments are introduced into the body through small puncture orifices.

Endoscopic procedures typically are commenced by using a device known as a trocar. The trocar comprises a cannula or trocar sleeve (a hollow sheath or sleeve with a central lumen) and a sharp obturator received in the cannula. The trocar is used to penetrate the abdominal wall or chest. The obturator is withdrawn from the cannula after the intra-abdominal end of the trocar is in the abdominal cavity, and the cannula remains in the abdominal wall throughout the surgical procedure, allowing the introduction of surgical instruments. Trocars are available in different sizes, as are cannulae, to accommodate various instruments.

Endoscopy, in the form of laparoscopy, traditionally has been used almost exclusively for gynecological surgery. However, physicians specializing in other fields have begun to recognize the diagnostic and operative value of endoscopy.

The advantages of endoscopic surgery include: procedures may be performed on an outpatient basis; surgeons are given the opportunity to view intra-abdominal viscera without performing a laparotomy, a large incision of the abdominal wall; small puncture ports or wounds are created rather than large incisions, lessening trauma; patient and insurer medical costs are reduced by shorter hospital stays; and probable reduction of postoperative patient discomfort and recovery times.

Thus, there is a substantial interest in and need for providing task-specific surgical instruments particularly adapted to general surgical procedures now being performed endoscopically. Because endoscopy, particularly laparoscopy, is an evolving specialty within the field of general surgery, currently available instruments inadequately meet the needs of laparoscopic surgeons.

Surgical instruments designed for endoscopic procedures generally have taken the form of a surgical tool (hereinafter called an end effector), e.g., scissors, dissectors and cutting jaws, attached to the distal end of an elongated shaft, with an operating linkage mechanism internal or external to that shaft. A handle attached to the opposite, proximal end of the shaft usually has an associated manual mechanism for operating the end effector, and may have a second manual mechanism to rotate the shaft and end effector. Generally, in order to fit through the small diameter ports or incisions, an instrument is designed for a single, dedicated, specialized purpose. Ideally, a surgeon selects instruments according to his preferences and according to the procedure at hand. However, because of the costs involved with using additional instruments and the time associated with removing one and inserting another, a surgeon is inclined to make do with the instrument of initial use even though another instrument may be more suitable for the immediate task.

Current endoscopic surgical instruments provide a surgeon with only limited ability to reposition the end effector without having to remove the instrument from the patient. Of significant import is the limited ability to pivot the end effectors of existing instruments relative to the longitudinal axis of their elongated shafts. Typically, the end effectors are fixedly attached to the elongated shaft, and thus there is no pivoting capability whatsoever. When using an instrument with no pivoting capability, correct placement of the port is crucial for direct access to the subject tissue or internal structure. Frequently, due to the fixed position of the end effector relative to the instrument shaft, additional laparoscopic ports or incisions must be created to allow a suitable instrument angle and access to the tissue of interest.

U.S. Pat. No. 5,383,888 to Zvenyatsky et al. discloses an endoscopic surgical instrument having a means by which a surgeon is able to pivot the surgical tool while in use; however, this pivoting ability is limited by the pivoting means employed. The end effector of the Zvenyatsky et al. instrument is fixedly attached to an intermediate piece, called an articulating section, which in turn is what is pivotally attached to the instrument's elongated shaft. The pivoting action in the Zvenyatsky et al. instrument thus involves the pivoting of both the articulating member and the surgical tool. Thus, it can be seen that the total radius of articulation (i.e., pivot radius) in the Zvenyatsky et al. instrument equals the length of the articulating member plus the length of the surgical tool.

It is desirable to have the shortest possible radius of articulation. This is so because a surgeon is generally only interested in the location and angle of the surgical tool. In other words, it is seldom the case that the surgeon would use a pivoting head to reach a work area at a great distance perpendicular from the axis of the elongated shaft. Thus, while pivoting the surgical tool, the surgeon must move the elongated shaft laterally in the opposite direction a distance proportional to the radius of articulation. Although not difficult in itself, this movement is exaggerated by the length of the articulating section. Further complicating the precise positioning of the end effector laterally from the proximal end of the shaft is the lack of depth perception of the laproscopic camera. Thus, it can be seen that the greater the radius of articulation, the more difficult it is to precisely position the end effector. Furthermore, because space is generally restricted at the surgical site, the surgeon using the Zvenyatsky et al. instrument may not have enough space to move the elongated shaft laterally in one direction in order to pivot the surgical tool in the other direction, or similarly, there may not be enough space for the entire length of both the articulating member and the surgical tool to be pivoted.

Another limitation in the design of current endoscopic surgical instruments is that to reposition the end effector, a surgeon must use both hands—one hand to manipulate manually a thumbwheel or knob to rotate the shaft (and end effector), and one to hold the instrument. This means that a second instrument in use has to be released, or the assisting physician or nurse has to provide help.

Next, it is desirable that the end effector be easily detachable from the distal end of the elongated shaft. This allows a surgeon to use the same handle and elongated shaft for different surgical procedures, thus saving the expense of additional handles and shafts. Further, having a detachable end effector allows the end effector to be readily and easily cleaned or sharpened. In addition, the end effector may be designed to be disposable, whereas the handle and elongated shaft would be reusable.

No end effector detachment mechanism is known to exist for an endoscopic surgical instrument having an end effector with three degrees of freedom, e.g., rotation, pivot, and pinching. U.S. Pat. No. 5,368,606 to Marlow et al. discloses an endoscopic surgical tool in which the end tool is removable from the elongated shaft. The attachment mechanism consists of a threaded end effector support which is screwed into the elongated shaft. Internal to the end effector support is a stub shaft which is connected, via a ball captured in a socket, to a rod which extends internal to the elongated shaft. The stub shaft operating in conjunction with the rod is what controls the pinching action of the end effector. The instrument to which the Marlow et al. detachment means applies does not, however, have an end effector that is pivotable. It is believed the Marlow et al. detachment concept cannot be applied to operably connect the linkage mechanisms of an instrument with an end effector capable of being pivoted, as well as being rotated and pinched.

Accordingly, it is an object of the present invention to provide an endoscopic surgical instrument which enhances a surgeon's capability and dexterity, yet requires a minimum number of endoscopic ports. A further object is to design the endoscopic instrument to pass through trocar sleeves or endoscopic ports of various sizes, including 5 mm trocar sleeves, thereby permitting its use in minimally invasive procedures.

Another object of the present invention is to provide an endoscopic surgical device having a rotatable and pivotable end effector or instrument head, thus enabling the surgeon to reach areas difficult to access quickly and conveniently without having to move or reposition the instrument as a whole. In this regard, the objective is to provide an instrument having the capability of positionally rotating, pivoting and operating the selected end effector without the need for an additional articulating section. A more specific objective is that the radius of articulation of the end effector's pivoting movement is to be minimized.

Yet another object of the present invention is to provide an instrument adapted to accept various types of end effectors. Generally, the different interchangeable end effectors include those providing all cutting and pinching or grasping actions, those providing other movements at the distal end of the instrument, and single-piece, probe-like end effectors. A further objective is to provide for the easy detachability of these end effectors from the rest of the instrument.

Still another object of the present invention is to provide an endoscopic instrument wherein the positioning and the operation of the end effector is controlled, at least in part, by an integrated microprocessor.

The above and other objects of the present invention will become more apparent and understood upon consideration of the following description, in conjunction with the accompanying drawings and claims.

SUMMARY OF THE INVENTION

The present invention is directed toward an endoscopic surgical instrument that satisfies the aforementioned objectives. An endoscopic surgical instrument having the features of the present invention comprises a handle, a tubular member (also called a barrel, barrel tube, or tubular barrel), and an end effector for performing a surgical task. The handle provides for holding the instrument, and is the source of or conduit for motive power for operating and controlling the end effector. The barrel is generally tubular, with one end being rotatably connected to the handle. The end effector is pivotally attached to the other end of the barrel, and the instrument includes a means for operably linking the end effector and motive power. Closure of the end effector can be accomplished irrespective of the state of pivoting of the end effector pieces, thereby allowing independence between the pivoting, rotation and pinching movements.

In the preferred embodiment, the end effector comprises two pieces, both of which are pivotally attached to a clevis fork on the distal end of the tubular barrel. A pair of rack and pinion mechanisms actuate the end effector. A gear pinion is machined into the proximal end of each of the two pieces of the end effector, and each pinion is pivotally mounted in the clevis fork. A pair of linear racks are slidably mounted within the fork, each of which engages its respective pinion. Each rack and pinion pair is independent; therefore, moving one rack in the distal direction causes pivoting of that end effector piece relative to its neighbor. Pulling the rack in the proximal direction causes pivoting of that end effector piece in the straight direction. Pushing both racks in the distal direction causes pivoting of the end effector (i.e., both pieces thereof) and pulling both racks together causes straightening of both pieces of the end effector. Pushing one rack relative to the other causes opening of one end effector piece relative to the other while pulling one rack while holding the other stationary causes "snipping" action of the end effector pieces. Axial rotation (i.e., rotational movement about the longitudinal axis of the barrel) is achieved by rotating the tubular barrel, including the linkages and end effector assembly, relative to the handle. Coordinated movement of the racks is via two long linkage rods which extend back into the handle. The linkage rods are coaxial within the barrel. The two rods are constrained from rotating within the tubular barrel, but can move lengthwise inside the barrel. Each control rod has a threaded portion on its proximal end. When attached to the handle, each threaded portion mates to its own elongated screw. The two drive screws inside the handle rotate together, however one of them is restrained axially in position, while the second is attached to a trigger-like operator and can move proximally. Thus, when the trigger is moved, one rack moves relative to the other and closes the end effector. The end effector pivots when the two screws are driven as a pair and both linkages screw forward on their respective screws. Rotation of the screws, and the resulting pivoting of the end effector pieces, may be done manually, or with small gear motors. Movement of the two linkages and resultant closure of the pieces of the end effector relative to each other is accomplished either manually or automatically. In the manual embodiments, a set of levers and linkages is connected to a trigger-like arm attached to the pistol grip handle and is actuated by squeezing the hand closed. Manual closure offers direct tactile feedback to the user. A manual trigger lock is also provided for the user to grasp and lock onto tissue or implements.

In the electrically driven or powered embodiment, movement of the linkages is achieved with the aid of a geared motor or other source of motive power. The motor may be internal or external to the handle of the device, and an appropriately located power on/off switch, or switches, are associated with the handle.

The assembly comprising the end effector blades, racks and control rods, is detachable by disengaging a set of bayonet fittings connecting each control rod with its respective elongated control linkage. Disengagement is accomplished by rotating the tubular barrel relative to the two internal linkages.

The present invention may be sterilized using standard procedures such as steam or immersion. Furthermore, the invention is also suitable for use with electrocautery, and thus has a connection for an external electrocautery power supply.

In another embodiment, the end effector blades are pivotally attached to a clevis fork, crossing over one another at a pivot point, and the opposite portions of each piece are configured as levers, extending in the proximal direction. The external sheath of a control cable, capable of acting in both tension and compression, is attached to the proximal end of one blade. The center core of the control cable, which is slidable within the external sheath, is attached to the opposite blade and is also capable of acting via both tension and compression.

The other end of the control cable, including both the sheath and core, leads inside the tubular barrel and is suitably coupled to a pair of elongated linkages which extend back into the handle. Pushing the sheath and core together in the distal direction pushes a loop of sheath and core toward the end effector causing pivoting of both pieces of the end effector relative to the tube. Pushing and pulling the core relative to the sheath causes opening and closing of one end effector piece relative to the other. Pulling the cable (i.e., sheath and core together) causes straightening of the end effector and pulling the core only causes "snipping" action of the end effector pieces. This end effector assembly may also be detachably mounted to the handle by way of the bayonet coupling described above.

Yet another embodiment of the present invention utilizes a pair of long, sliding linkages, each of which directly engages one of the two pieces of the end effector. As with the second embodiment, the pieces (e.g., blades) cross over one another at a pivot point, and extend in the proximal direction, the opposite portions of each piece are configured as levers with elongated diagonal slots. The distal end of each linkage has an integral clevis pin which engages in the slot of its respective end effector piece. The two linkage/piece pairs work identically. Pushing one linkage in the distal direction causes the pin to slide up its slot toward the pivot, causing rotation of the piece. Pushing the linkage further in the distal direction causes continued rotation as the pin now progresses down the slot away from the pivot. In this way, pushing both linkages in the distal direction causes pivoting while pushing one and pulling the other causes scissoring. As above, this end effector assembly may be removably attached to the handle, also using bayonet fittings also.

In another embodiment of the present invention, the end effector may, as above, be scissor-like, having two blades pivotally connected to the distal end of the tubular barrel. One jaw end of each of the blades of the scissor end effector is sharpened to allow shearing between the two blades as they pivot against one another. The blades cross over one another at a pivot point, and the opposite portions of each blade are configured as levers extending a distance (depending on the leverage required) in the proximal direction. Between these levers is a spring biasing the levers apart, thereby opening the cutting jaws. On the outside edges of these levers are grooves which extend around a radius on the proximal end of the levers. The grooves are polished and wide enough to accommodate a high modulus tensile cord which is free to slide back and forth therein.

In this embodiment of the instrument, there are two tensile cords, each of which is attached to one blade and crosses around the proximal end of the opposite blade in its own groove. Each cord runs in the opposite direction around its own pulley on the opposite sides of the two blades. The free ends of the two cords lead inside the tubular barrel and are suitably coupled to an operating drive mechanism associated with the handle. These cords are kept in positive tension by the action of the spring between the lever end of the blades. Pulling one cord while releasing the other causes coordinated pivoting of the two blades. Pulling the two cords simultaneously causes coordinated closing of the blades. Rotating the tubular barrel causes axial rotation of the blades together with the pulleys and cords.

Coordinated movement of the two cords is achieved by the use of a threaded shaft mounted within the tubular barrel. The distal end of the internal shaft is threaded with a right-hand thread, followed by a left-hand thread. Two nuts (one threaded in right-hand orientation and the other in left-hand orientation) which are constrained from rotating, but can slide lengthwise inside the tube, are screwed onto the shaft. One of the above mentioned cords is attached to the first (distal end) nut while the second passes through a hole in the first nut and attaches to the second nut (proximal end). The threaded shaft, which can both rotate and slide axially inside the tubular barrel, is attached to a spline within the pistol grip handle. A cylindrical collar is also located within the handle and is attached to the shaft to allow engagement by a trigger mechanism to pull the shaft, together with the nuts and cords, in the proximal direction, thereby closing the scissor blades. Rotation of the shaft, by way of gears engaging the spline, allows coordinated movement of the nuts, and thereby the cords, pivoting the scissor blades in either direction.

A feature of the invention also is the inter-changeability of end effector tips. In one embodiment, the tubular barrel and shaft(s) have a splined section to allow engagement with gearing means within the handle. The retraction linkages or levers (which close the two pieces of two-piece end effectors) are capable of being disconnected from the collar attached to the threaded shaft inside the tubular barrel. Replacement of the tip and barrel is accomplished by pressing a button or otherwise releasing a detent mechanism on the handle, releasing one tip so that another tip of the same or a different type may be inserted.

The instrument of the present invention advantageously provides flexibility by including a family of instruments, through the use of a common handle and actuating drive mechanism, and different, replaceable end effector tips, each connectable quickly and conveniently to the drive mechanism according to need. This inter-changeability gives the user the ability to change from one functional device to another quickly and easily while continuing to use a common handle with its associated motors, gears and controls. It also permits parts of the device to be disposable while making the most expensive parts reusable. A major advantage is that the working end effector portion of the device which penetrates the patient's body cavity will be new, sharp, and guaranteed sterile, while the rest of the device can be cleaned, sterilized, and reused. of course, if justified by cost factors, the entire instrument may be disposable.

The present invention has several additional important advantages over existing endoscopic surgical instruments beyond the capability to incorporate various end effector tips and articulate the selected end effector. Incorporation of electronically controlled motors and clutches gives additional flexibility to the user interface which a surgeon uses to move the device in the desired directions. This interface may take the form of small slide switches, joysticks, knobs or buttons and electronic logic integrated into the handle or a remote interface controlled by a computer or other external device. An advantage of incorporating a microprocessor into the instrument of the present invention is that the logic can maintain accurate and repeatable positional control of drive motors or other motive, operational mechanisms.

The above and other features, objects and advantages of the present invention will become more fully apparent and understood upon consideration of the following detailed description, in conjunction with the accompanying drawings and claims. It should be understood that the descriptions and drawings are for purposes of description and illustration only and are not intended as a definition of the limits of the invention.

BRIEF DESCRIPTION OF THE DRAWINGS

FIG. 4A is an elevational view similar to that of FIG. 3 and depicts one embodiment of the connection between an end effector assembly and a portion of the elongated barrel of the present invention.

FIG. 4B is an elevational view of the proximal portion of the elongated barrel of the present invention, partially in section, depicting the attachment mechanism of the end effector assembly.

FIG. 5C is a view similar to that of FIG. 5A and depicts the movement of the linkages resulting in the pinching or closing of the end effector.

FIG. 8 (including FIGS. 8A and 8B) depicting the overall main operation and FIGS. 9–17 depicting subroutines.

FIG. 21 is similar to FIGS. 20A–C, but depicting coiled sheath used in the control cable.

FIG. 24A is a plan view of an end effector assembly similar to that of FIG. 23, with the jaws aligned with the barrel and closed.

FIG. 24B is an end elevational view, partially in section, of the end effector assembly shown in FIG. 23, with the end effector pivoted 45°.

FIG. 26A is an elevational view, partially in section, of an alternative embodiment of a manually operated handle utilizing rack & pinion mechanisms.

FIG. 26B is similar to FIG. 26A and depicts movement which results in the pivoting of the end effector.

FIG. 26C depicts movement of the trigger which results in the closing of the end effector.

FIG. 27B is a view similar to that of FIG. 27A and depicts the side view of the end effector assembly.

FIG. 27C is a view similar to that of FIG. 27 and depicts the end effector in the closed position.

FIG. 28A is an elevational view of the control linkage for the end effector of FIG. 27.

FIG. 28B is a view similar to that of FIG. 28A and depicts the closing of the blades of an end effector by moving the control linkage.

DETAILED DESCRIPTION OF THE INVENTION

Figure 1:
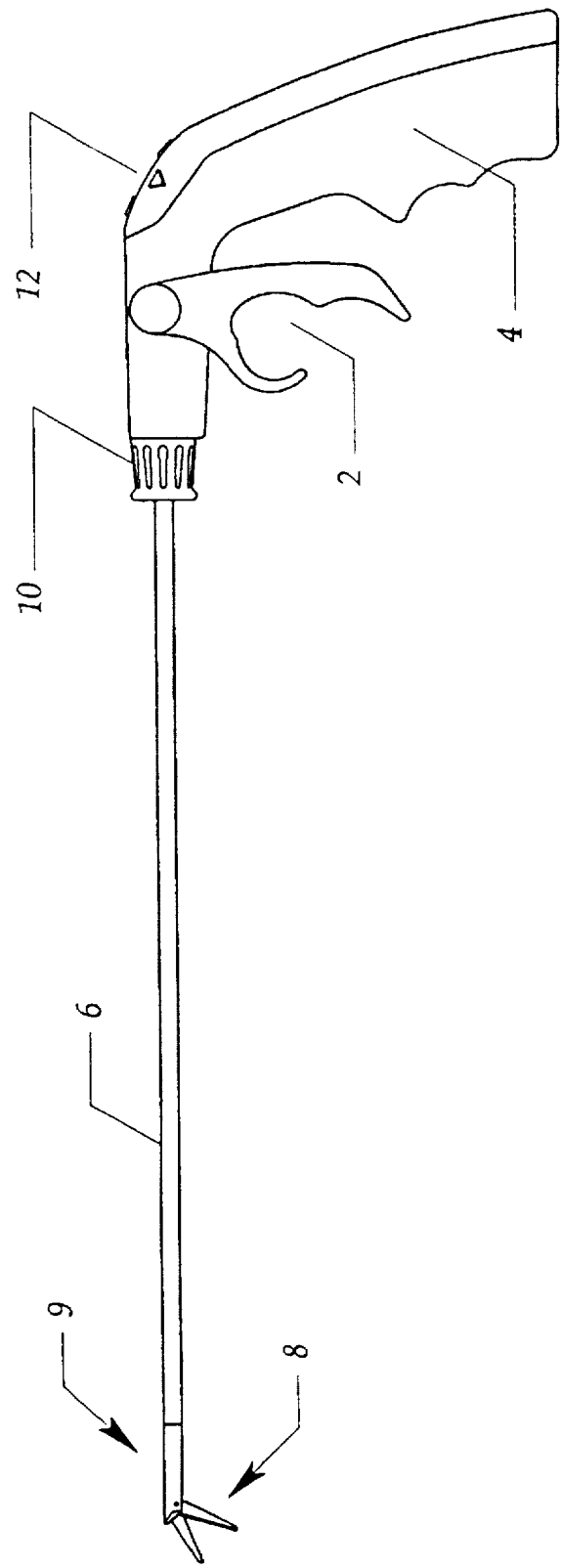
FIG. 1 is an elevational view of an embodiment of the entire instrument of the present invention.

Referring to FIG. 1, an embodiment of the present invention includes a handle 4 with an operating trigger 2 and control buttons 12, a tubular member 6 (also referred to herein as a barrel tube, tubular barrel, or just barrel), a removable end effector assembly 9 with an end effector 8, and a disconnect knob 10. As set forth in more detail herein below, the handle 4 houses an actuating means, including the drive and control mechanisms, motor(s) and associated gearing, batteries, control electronics, actuator switches and necessary wiring.

With regard to means for fastening, mounting, attaching or connecting the components of the present invention to form the surgical instrument as a whole, unless specifically described as otherwise, such means are intended to encompass conventional fasteners such as machine screws, rivets, nuts and bolts, toggles, pins, or the like. Other fastening or attachment means appropriate for connecting components include adhesives, welding and soldering, the latter particularly with regard to the electrical system.

All components of the electrical system and wiring harness of the present invention are conventional, commercially available components unless otherwise indicated. This is intended to include electrical components and circuitry, wires, fuses, soldered connections, circuit boards and microprocessor components.

Generally, unless specifically otherwise disclosed or taught, the materials from which the metallic parts (e.g., the barrel, end effector, etc.) of the present invention are formed are selected from appropriate materials such as stainless steel and metallic alloys. The handle may be formed of various plastics or the like.

Despite the foregoing indication that components and materials for use in and for forming or fabricating the surgical instrument of the present invention may be selected from commercially available, appropriate items, the following detailed description sets forth specific items and steps for use in the present invention, although it is possible that those skilled in the state of the art will be able to recognize and select equivalent items.

The tubular member 6 of the instrument houses linkage means 28, 30, 70, 72 (see, for example, FIGS. 3 and 4B) for closing and pivoting the end effector 8 and, referring to FIGS. 4A and 4B, includes a disengagement mechanism to allow removal of an assembly comprising end effector 8 from the remainder of the instrument. In FIG. 1, the end effector 8 is illustrated as a scissor-like working tip. However, other types of end effectors that can be used include graspers, extractors, clamps, forceps, retractors, biopsy tools, and other devices useful during surgery. The end effector 8 may be disposable or reusable.

Figure 2A:
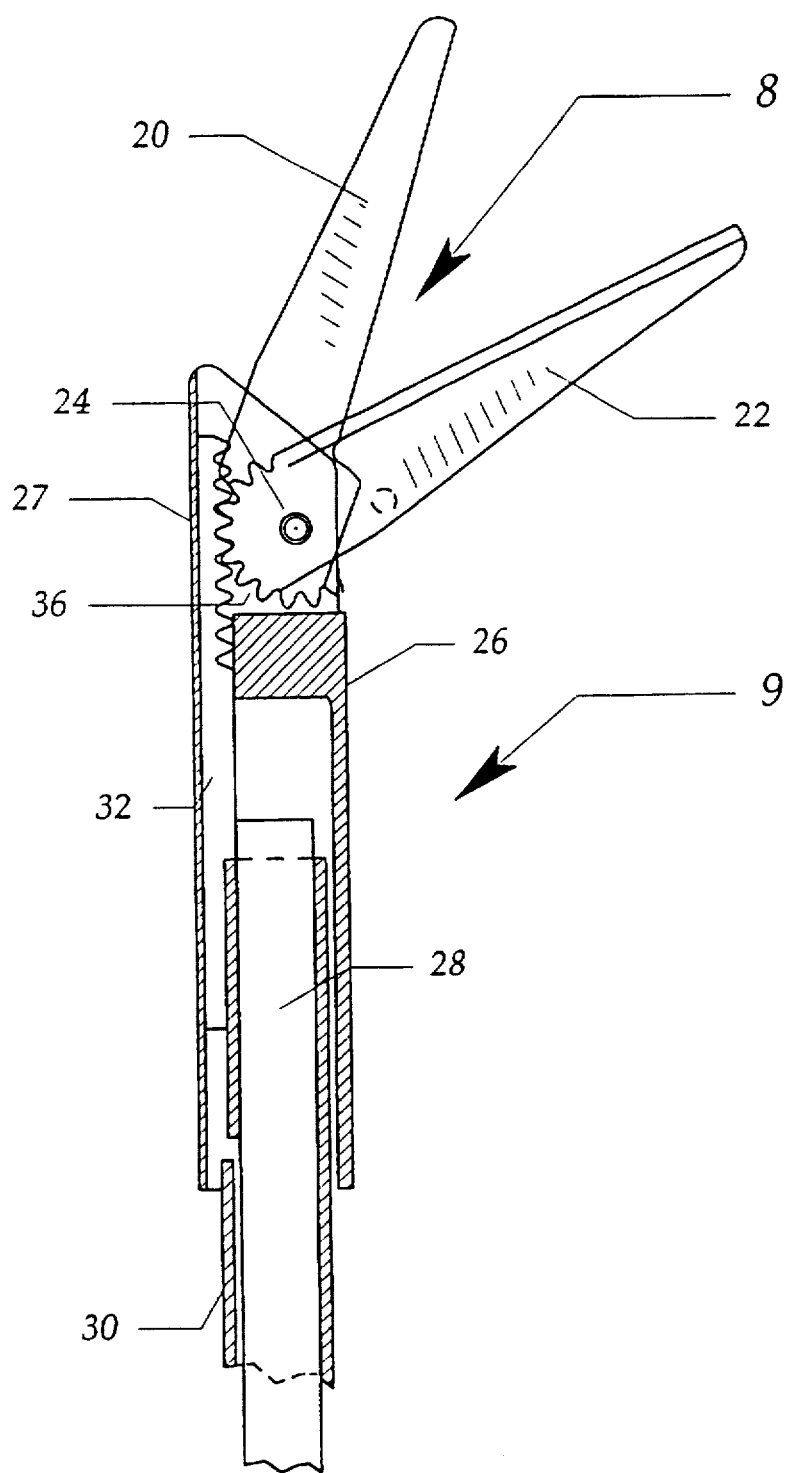
FIGS. 2A–E are elevational views, partially in section, depicting an embodiment of the end effector assembly utilizing rack & pinion mechanism.
Figure 2B:
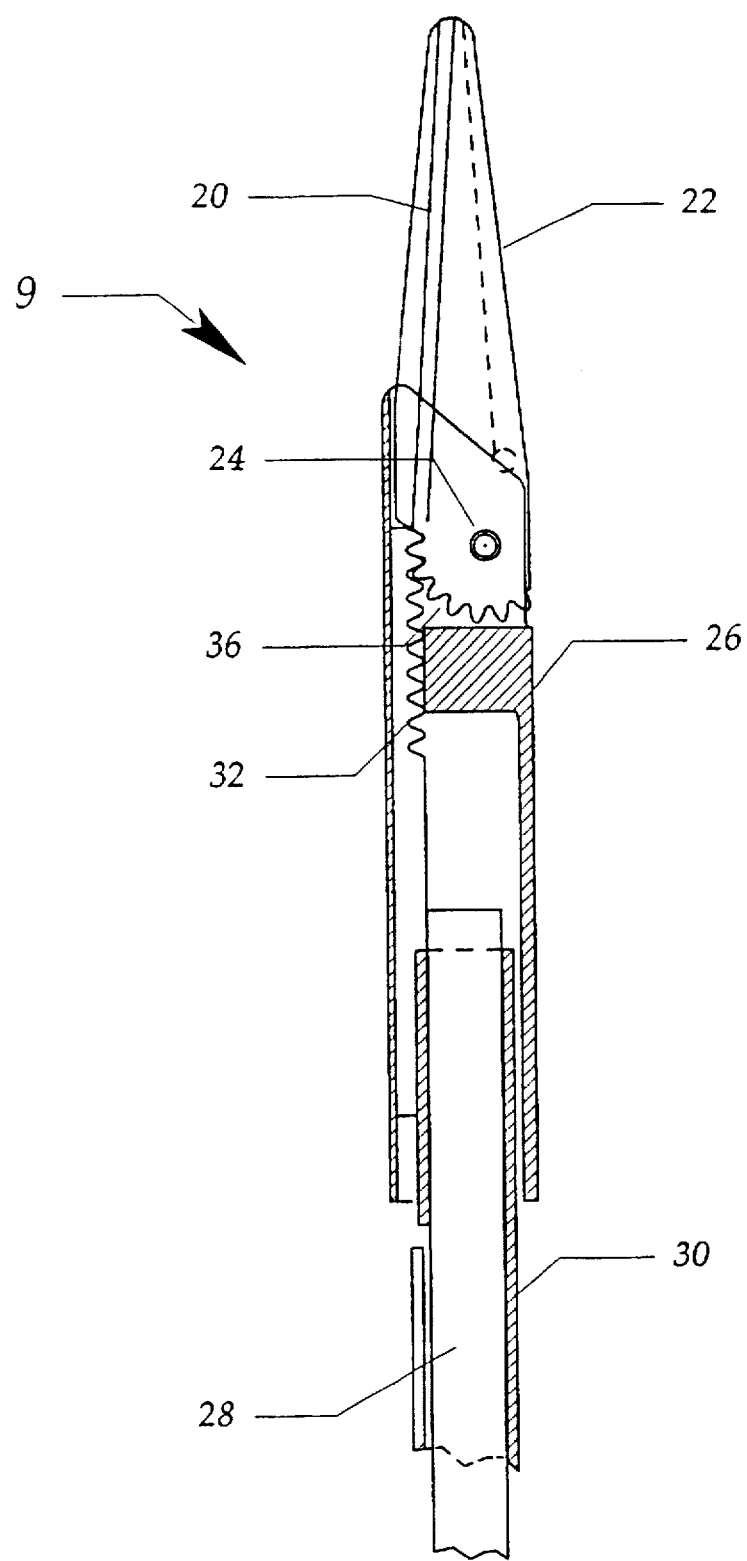
Figure 2C:
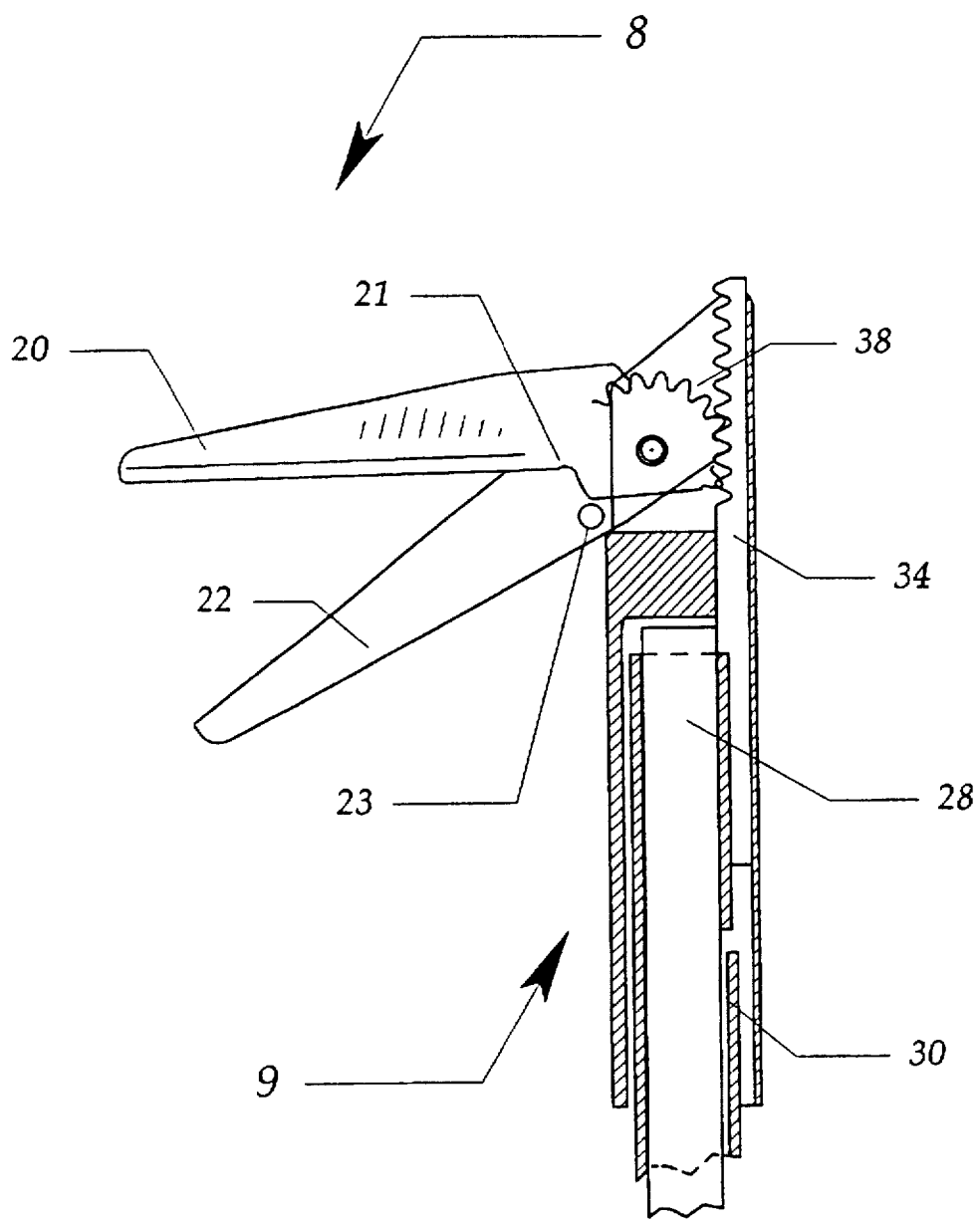
Figure 2D:
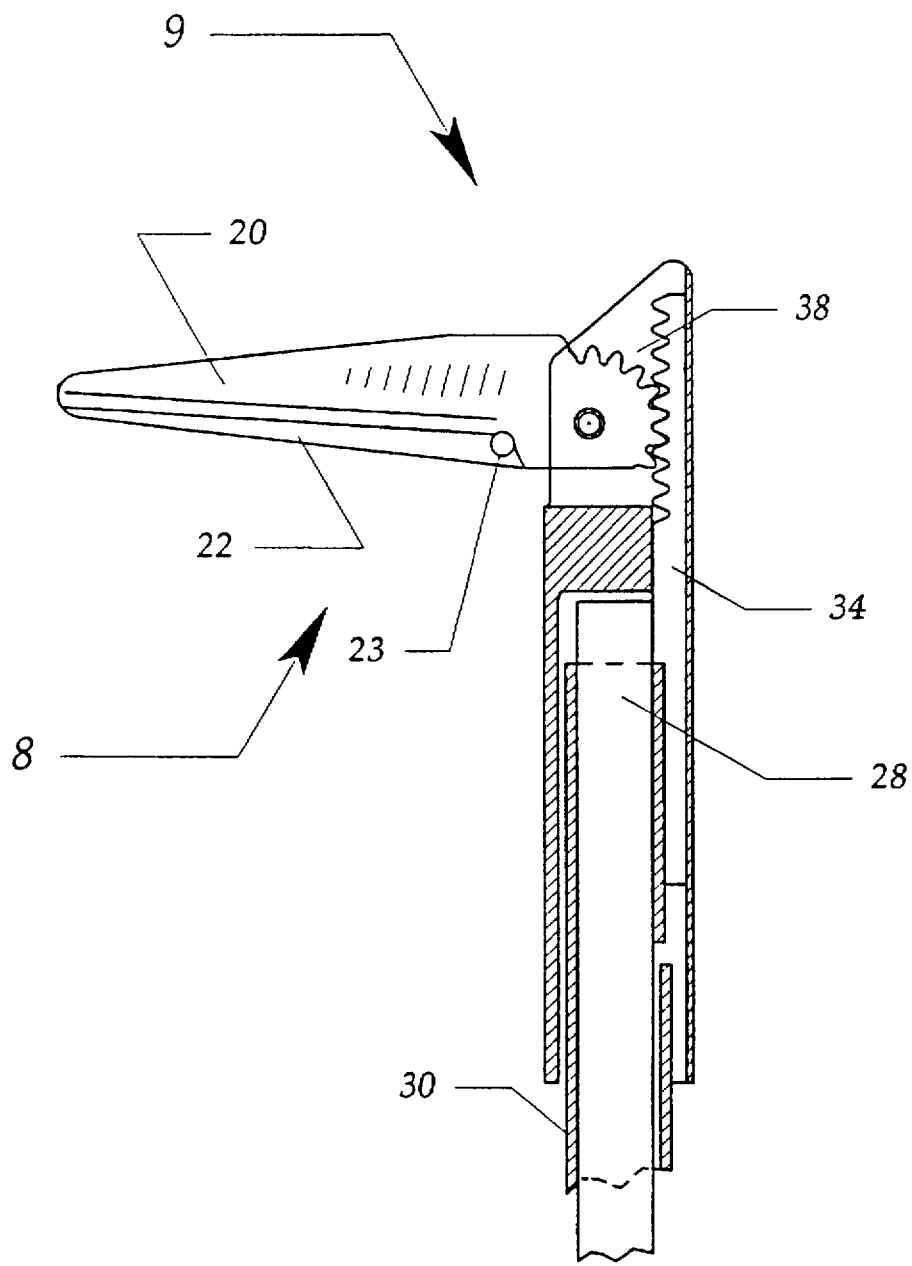
Figure 2E:
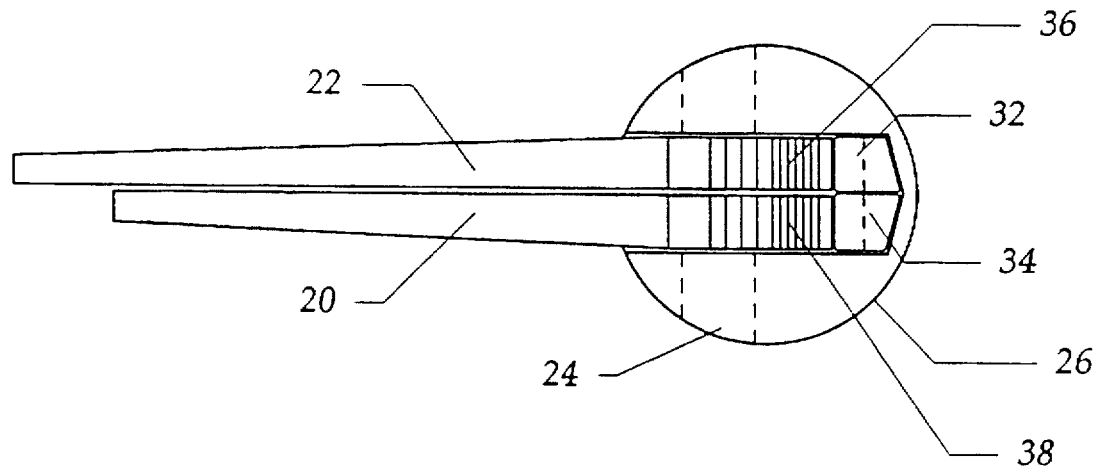

Referring to FIGS. 2A–E, a preferred embodiment of an end effector assembly 9 is depicted. In FIG. 2A, the end effector pieces 20 and 22 are pivotally attached to a clevis fork 26 by pin 24 such that both end effector pieces may pivot freely. On the proximal end of end effector piece 22 are gear teeth 36. These gear teeth 36 engage mating teeth disposed on rack 32. The tail of rack 32 is attached to a first control rod 30 which is slidably mounted in the clevis fork 26. Referring to FIG. 2E, end effector piece 20 has its own proximal gear teeth 38 and rack 34 which are independent of end effector piece 22 and rack 32. Referring back to FIG. 2C, rack 34 is attached to control rod 28 which is slidably disposed inside control rod 30. Both rack/control rod assemblies are free to slide longitudinally and are held in engagement with the gears by a side portion 27 (FIG. 2A) of the fork 26 which encloses the back of the rack. Pushing the rack 32 (see FIG. 2A) in the distal direction causes pivoting of the end effector piece 22, opening the blade relative to its neighbor. The rack is, protected from tissue by the angular protrusion of the fork in the region denoted 27 which can be seen in FIG. 2A. One characteristic of the small gear tooth design is that the tensile and compressive stresses are extremely high on the gear teeth and rack sections. For this reason both the gears and racks must be fabricated out of extremely high-toughness metal alloys having failure stresses in excess of 150,000 psi.

Now referring to FIG. 2A, the end effector 8 is pivoted 20° from straight, and the end effector pieces 20, 22 are open slightly. "Snipping" action is performed by pulling rack 32 in the distal direction, which causes end effector piece 22 to pivot counterclockwise, while rack 34 (not shown here) remains stationary. The resulting action is that end effector piece 22 "scissors" toward motionless end effector piece 20. Still referring to FIG. 2A, the simultaneous pivoting of both pieces 20, 22 of the end effector 8 is accomplished by simultaneously pushing both racks 32, 34 (34 is not shown in this Figure) in the distal direction. Conversely, straightening both pieces 20, 22 is accomplished by pulling both racks 32, 34 (see FIG. 2E) in the proximal direction. (FIG. 2B shows that end effector pieces 20, 22 closed and straight.) As described, the end effector pieces can be opened and closed when the pair is any angle between 0° and 100° from straight.

FIG. 2C is a view of the end effector assembly 9 from the side opposite that depicted in FIG. 2A and shows the end effector pivoted to its maximum angle (about 110°) and open maximally. A small pin 23 protrudes from end effector piece 22 and is received in small notch 21 of end effector piece 20 when the end effector is closed. This pin 23 and notch 21 prevents one end effector piece from crossing over center when closed. FIG. 2D shows the end effector pivoted 90° from straight and closed.

FIG. 2E is a distal end view of the end effector 8 with end effector pieces 20, 22 pivoted 60° over and open slightly. In this view, the two racks 32, 34 can be seen clearly as can the gear teeth 36, 38 of each end effector piece. As can be seen in FIG. 2B, none of the mechanism protrudes outside of the defined diameter of the barrel tube 6. In a preferred embodiment, that diameter is such that the instrument may readily pass through a 5 mm trocar sleeve or a laparoscopic port of only 5 mm (sleeve and port not shown). Thus, versatility and 3-dimensional control of the end effector 8 of the invention is achieved without sacrificing the small diameter required for minimally invasive surgical procedures.

Figure 3:
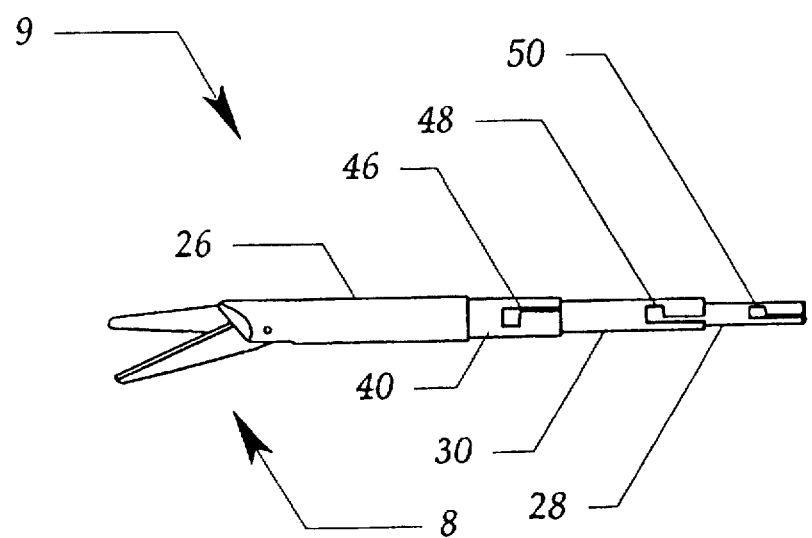
FIG. 3 is an elevational view of one embodiment of the detachable end effector assembly of the present invention.

As discussed previously, in the preferred embodiment of the present invention an assembly comprising end effector 8 is removable from the rest of the instrument. FIG. 3 shows such an assembly detached from the rest of the instrument. The end effector assembly 9 is comprised of (i) the end effector 8; (ii) the clevis fork 26 having a bayonet fitting 40 with a flag-shaped slot 46 cut such that the flag faces in a counterclockwise direction (when facing from the proximal direction); and (iii) control rods 28, 30. The control rods 28, 30, which are slidably mounted concentric inside the clevis fork 26, also have bayonet engagements 48, 50 cut in them. These flag-shaped slots 48, 50 are cut in the direction opposite that of the slot 46 in the clevis fork bayonet fitting 40. Both control rods 28, 30 are generally cylindrical in section but are connected in such a manner that they are restrained from rotating relative to one another or to the clevis fork 26. In the preferred embodiment, this is achieved by the attachment of the racks 32, 34 to the control rods 28, 30. The distal end of control rods 28, 30 are shown in FIGS. 2A–D.

Now referring to FIG. 4A, attaching the end effector assembly 9 to the barrel 6 is achieved by inserting the proximal end of the assembly into the distal end of the barrel tube 6 (as shown by arrows) and twisting the disconnect knob 10 in the clockwise direction (as show by arrow).

Referring to the distal end of FIG. 4B, engagement tabs 52, 54, 56 can be seen protruding radially into the interior of barrel tube 6 and control tubes 70, 72. These tabs respectively engage the flag-shaped slots 46, 48, 50 in the end effector assembly 9 shown in FIG. 4A. When the knob 10 is rotated into the unlocked position (clockwise when viewed from the proximal end), the barrel tube rotates with it, aligning the pair of tabs 52 (only one of which is shown) in the barrel tube with the pairs of tabs 54, 56 (only one of which is shown) inside the control tubes 70, 72. In the unlocked position, all pairs of tabs 52, 54, 56 align with the longitudinal pairs of slots 46, 48, 50 of the end effector assembly 9. The length of tabs 52, 54 are such that they do not engage or interfere with control rods internal to them, yet they fully engage their respective slots 46, 48. As the knob 10 is turned counterclockwise (as viewed from the proximal end), tab 52 engages slot 46 first. Continued rotation of the knob 10 then causes rotation of the clevis fork 26. Because control rods 28, 30 are constrained to rotate with each other and with clevis fork 26, rotation of the clevis fork 26 causes tab 54 to engage into slot 48 and tab 56 into slot 50 until all tabs are fully bottomed. At this point, the knob 10 and barrel tube 6 is torsionally locked relative to the control tubes 70, 72, thus prohibiting uncoupling of the end effector assembly. It is assumed that the user does not try to push the end effector rotate button 12 (see FIG. 1) and rotate the end effector 8 while trying to turn the knob 10.

Referring back to FIG. 4B, a compression spring 62 can be seen. The spring functions to hold the disconnect knob 10 in its proximal position thereby locking the knob against inadvertent rotation and disconnect of the end effector assembly 9. The spring 62 is compressed when knob 10 is pushed in the distal direction and held compressed as the knob 10 is turned. Also shown here, elongated control tubes 70, 72 are slidably mounted inside barrel tube 6 and extend inside drive tube 64. The elongated control tubes 70, 72 are also concentric with one another. The entire assembly is concentric. The two control tubes 70, 72 have elongated slots 58 through which a pin 60 passes and rotatably couples the tubes to drive tube 64, yet allows translation as required for pivoting and scissoring the end effector 8.

Figure 4C:
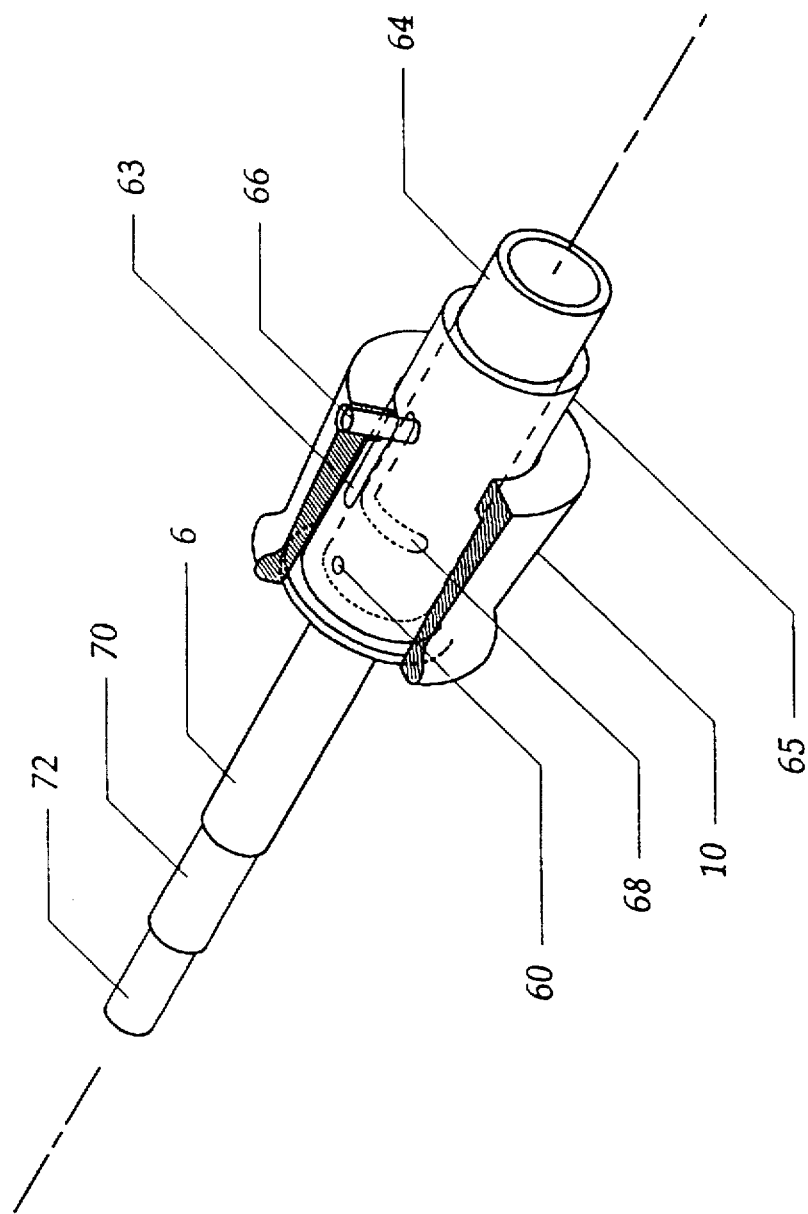
FIG. 4C is an isometric view, partially in section, showing more detail of the engagement mechanism for attaching the end effector assembly.

FIG. 4C shows further detail of how the disconnect knob 10 locks and unlocks relative to the control tubes 70, 72, allowing disconnection of the end effector. In this view, the disconnect knob 10 is shown in the locked position. Knob 10 is slidably mounted on barrel sleeve 65 which is welded or otherwise attached to tubular barrel 6. Barrel sleeve 65 is in turn concentric and rotatably mounted on drive tube 64.

Unlocking of the disconnect is achieved by pushing the knob 10 in the distal direction and rotating the knob ¼ turn in the counterclockwise direction (viewed from the proximal end). As the knob 10 is pushed, pin 66 slides along a straight longitudinal slot 63 in the sleeve 65. Pin 66 also slides along the longitudinal portion of an L-shaped slot 68 in the drive tube 64. When the pin 66 reaches the crook of the L-shaped slot 68 it allows rotation of the knob 10 in the counterclockwise direction. This causes rotation of barrel sleeve 65 and barrel tube 6 relative to control tubes 70, 72 which are coupled to drive tube 64. There is no axial displacement of any pieces except the disconnect knob 10. Locking of the knob 10 is the reverse. It should be noted that the pushing and rotating of the knob 10 is relative to the drive tube 64 which provides the rotation function. When locked, all parts labeled in FIGS. 4A–C rotate together.

Figure 5A:
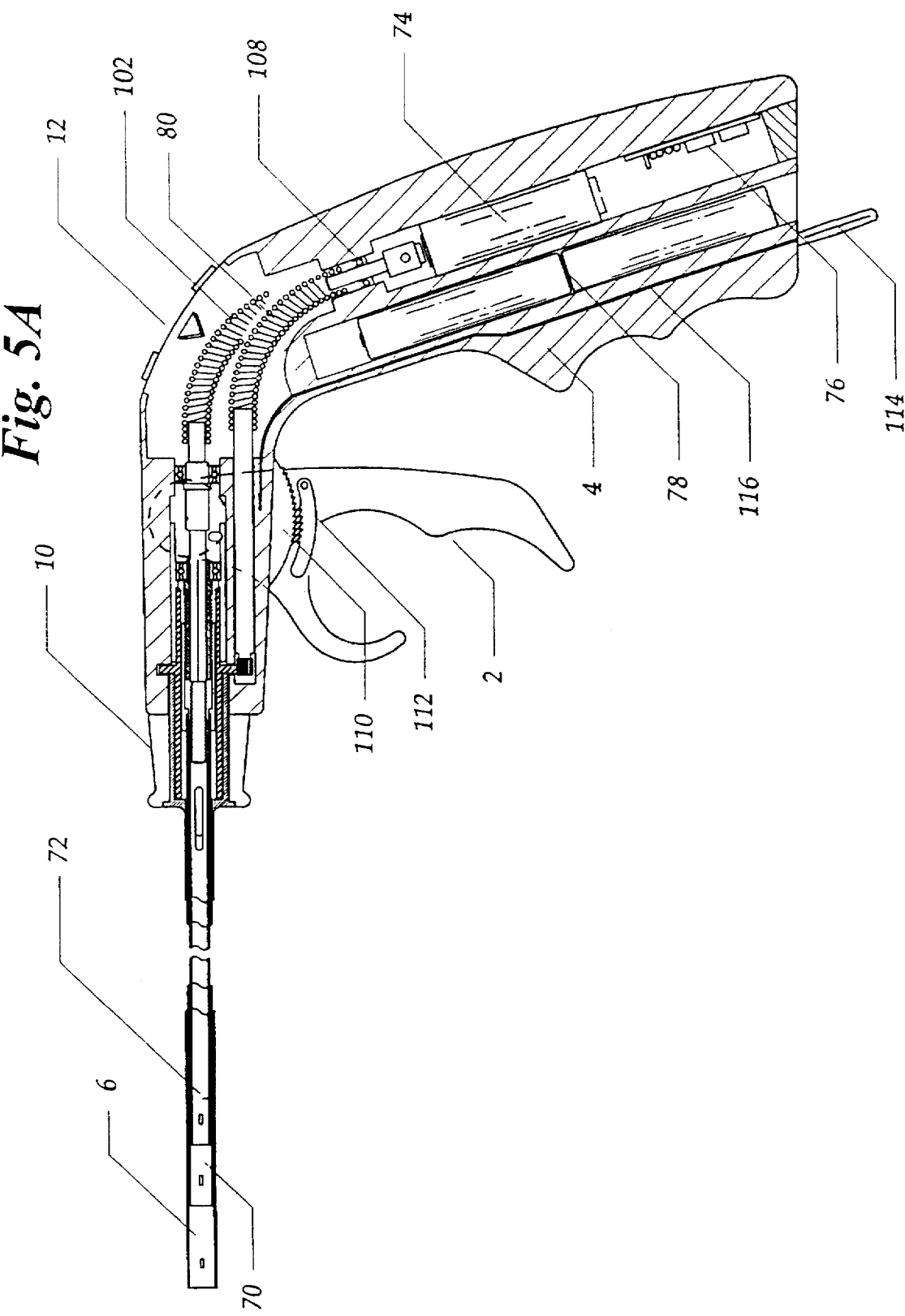
FIG. 5A is an elevational view of the handle of the present invention, partially in section, depicting the motors and actuation mechanisms with portions of the barrel connection and rotation mechanism removed for clarity.

Now turning to FIG. 5A, the handle 4 houses the actuating means or operating mechanism. In this preferred embodiment of the present invention, closing of the end effector is performed manually by retracting finger trigger member 2. The barrel 6, which is an integral part of the disconnect assembly shown in FIG. 4B, protrudes from the distal end of the handle 4, is rotatably connected to the handle 4, and is concentric with the centerline of the pivoting mechanism described hereafter. The two control tubes 70, 72, which in the locked position described above are constrained from rotating relative to the barrel tube 6, are able to slide lengthwise inside the barrel 6. Each control tube 70, 72 is movable axially by its own elongated screw 88, 90 (see FIG. 5B). Both of the screws 88, 90 are driven through a flex coupling 102 by a miniature gear motor (not shown), thereby causing the end effector to be pivoted. A second motor 74 drives a pinion 75 (shown in FIG. 5D) which causes rotation of the disconnect knob 10, barrel tube 6 and control rods 70, 72. The motors are controlled by thumb switch 12 and control electronics 76 (shown in FIG. 5A).

To allow the motors to survive sterilization by immersion in biocide solution or autoclave, the electronic circuit, switches (not shown) and motors 74 (the other not shown) are potted in sealant or sealed in a hermetic compartment (not shown). The motor shafts must pass through a vapor/moisture seal 108 which keeps the electronic components dry. Batteries 78 supply electric power for the motors and electronics. They may be replaceable or rechargeable.

Still referring to FIG. 5A, the handle 4 has also been designed to allow the surgeon to use monopolar electrocautery as desired. A dedicated electrical plug 114 is provided on the bottom of the handle for connecting an electrocautery cord. A conduction path 116 is provided through the non-conductive handle to the tubular barrel 6 and the end effector. The barrel 6 and clevis fork 26 (see FIG. 3) are coated with an electrically insulating material to avoid accidental electric shock while using electrocautery.

Figure 5B:
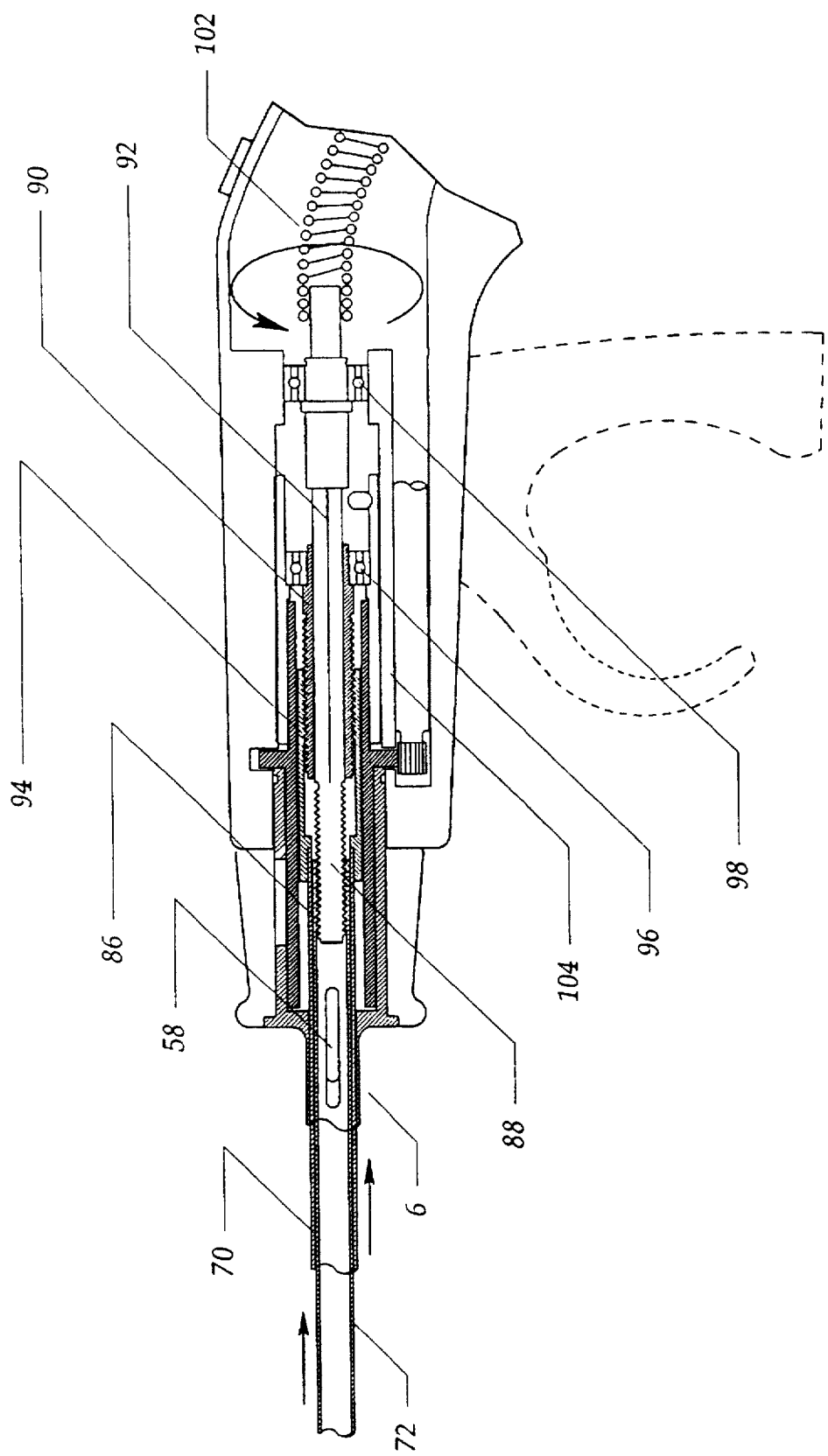
FIG. 5B is similar to that of FIG. 5A and depicts the actuation which causes pivoting movement of the end effector.

FIG. 5B shows more detail of how the end effector 8 pivots. In this preferred embodiment, screw 88 has a hexagonal or spline shape on its proximal section 92 which engages a mating profile on the interior of the sliding screw 90. The mating shapes allow the sliding screw 90 to slide relative to the drive screw 88, yet rotate together. Drive screw 88 is held in axial position by a bearing 98 located on its proximal end. The sliding screw 90 rotates on bearing 96 and is held in axial position by sliding yoke 104. The drive screw 88 is driven through flex coupling 102 by a gear motor (not shown). Each of the two control tubes 70, 72 is internally threaded on its proximal end, screw 88 engaging internal thread 86 on tube 72 and screw 90 engaging internal thread 94 on tube 70. The thread pitch of the two screw/ female thread pairs must be identical in order that both control rods slide in unison; otherwise, the end effector 8 would open or close perceptibly as it is pivoted. However, due to physical space considerations, it is desirable to utilize two different screw diameters. In this embodiment, the drive screw 88 is smaller and is coupled to the inner control tube 72, and the sliding screw 90 together with its control tube 70 slides over the outside.

Thus it can be seen that pushing the "pivot straight" button on the button pad ("Strt" in FIG. 6) actuates the motor (not shown) which turns the screws 88, 90 and thus retracts control tubes 70, 72 in the proximal direction as shown by the arrows. This retracts both racks 32, 34, thus straightening end effector pieces 20, 22 (as shown in FIG. 2B).

The pinching or scissoring movement of the end effector 8 can be seen more clearly in FIG. 5C. When the trigger 2 is pulled, the yoke 104, bearing 96, sliding screw 90 and external control tube 70 slide proximally, pulling in turn control rod 30 (FIG. 3) and rack 32 (FIG. 2A) which pivots end effector blade 22 (FIG. 2A). Despite movement of trigger 2, internal control rod 72 is held stationary in the barrel 6. Therefore, the continued action closes one end effector piece 22 against its neighbor 20, resulting in a shearing or pinching action.

Surgeons frequently require a locking mechanism to keep the instruments pinched on tissue or an object. In this invention, the trigger 2 can be locked in any position by a ratchet 110 and pawl 112 which can be engaged simply by sliding the finger upward in the finger loop. Ratchet 110 is fixed on the underside of the handle 4, and a slot is provided in the trigger 2 to allow clearance for the ratchet 110. A small pawl 112 is attached to the trigger 2 and can be flexed upward to engage the ratchet 110. The tooth profile on both the ratchet 110 and pawl 112 is designed to keep the trigger 2 locked until released. Release is achieved by pulling the trigger again, allowing the pawl 112 to snap downward, disengaging the rack 110, freeing the trigger 2.

Figure 5D:
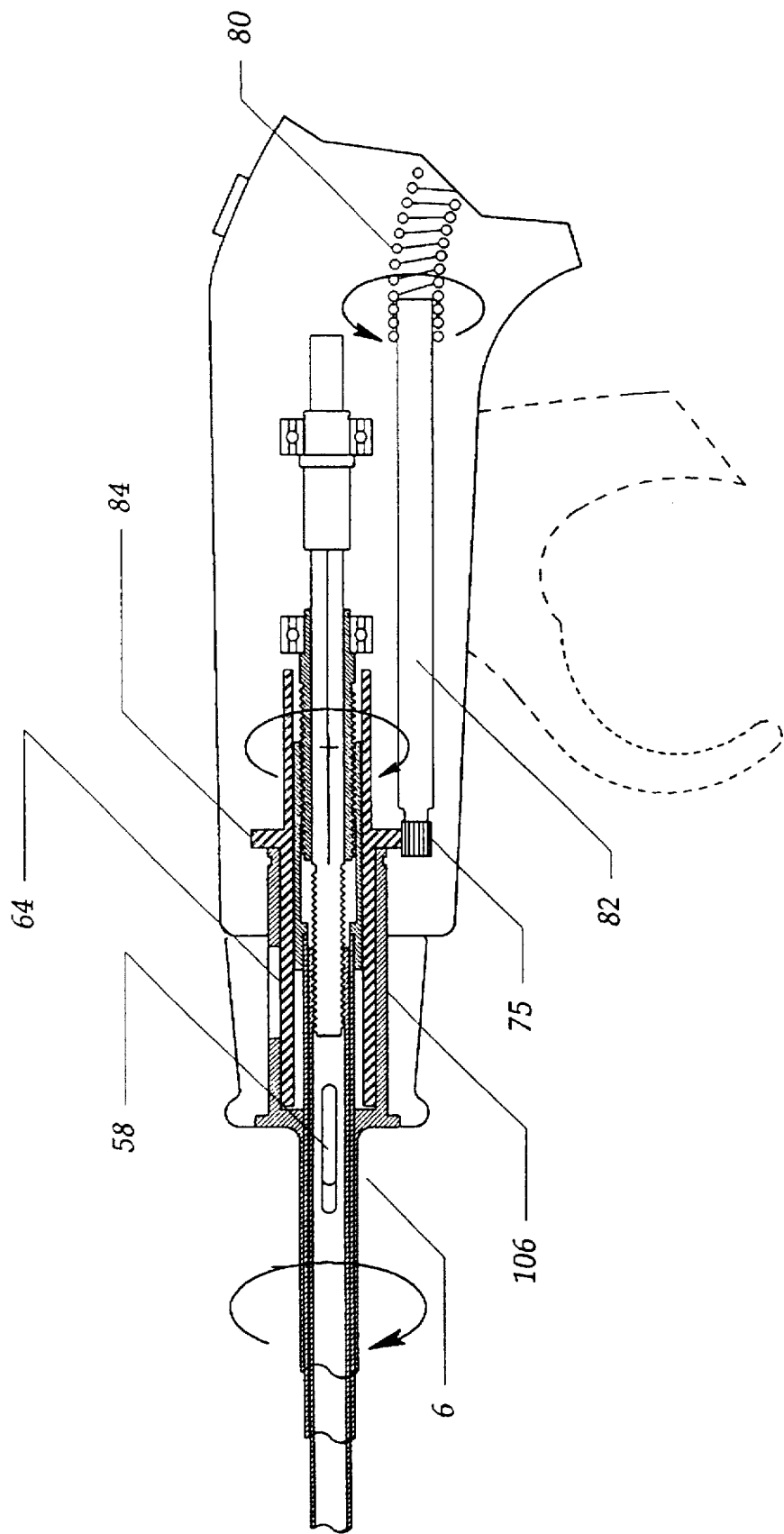
FIG. 5D is a view similar to that of FIG. 5A and depicts the axial rotation of the barrel.

The rotation movement of the end effector 8 is shown in greater detail in FIG. 5D. Rotation of the end effector 8 is accomplished by a separate gear motor 74 (see FIG. 5A) which, through flexible drive 80, turns pinion shaft 82. Pinion 75 engages gear 84 on the drive tube 64. As more clearly seen in FIG. 4B, drive tube 64 is coupled to the disconnect knob 10, tubular barrel 6, control tubes 70, 72 and thus the end effector 8. Thus pressing the "CCW" buttons on the button pad 12 (see FIG. 5A) causes rotation of the whole barrel tube assembly and end effector 8 in the counterclockwise direction, as shown by the arrows. The two motors 74 (see FIG. 5A; one motor hidden from view) are located side by side in the handle 4 and incorporate parallel and independent drive trains 80, 102, one shown in FIG. 5B, the other in FIG. 5D. There are significant advantages to the surgeon to have the rotation feature motor driven. However, rotation of the end effector may alternatively be accomplished manually by incorporating a knob on the distal end of the handle 4 which allows direct rotation of the tubular barrel 6.

Figure 6:
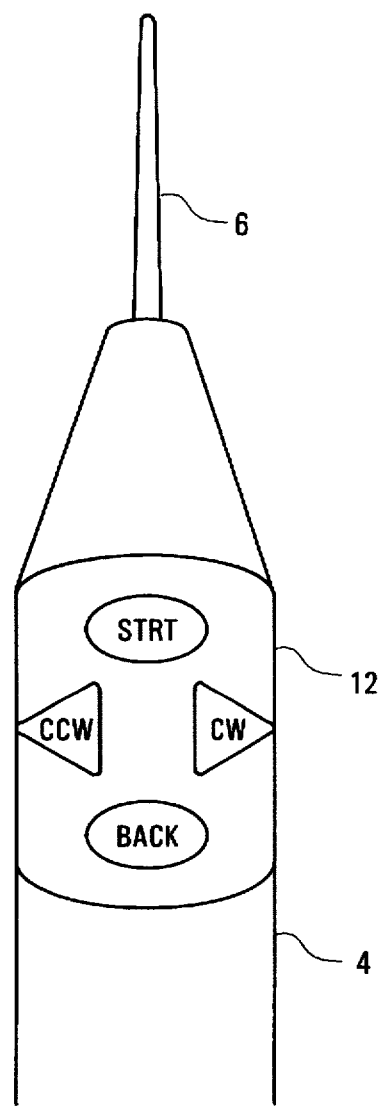
FIG. 6 is a rear elevational view of a portion of the handle.

FIG. 6 shows one method of controlling operation of the instrument; in this case, the control switch 12 is mounted on the handle 4. A small label covering switch 12 shows the effect of pushing each segment of the control switch 12 in each respective direction. The switch 12 may be controlled easily with the thumb of one hand, and has the following effects: (i) pushing the switch 12 label "strt" causes the end effector 8 to pivot to the straight ahead position (shown in FIG. 2B), (ii) pushing the label "back" causes the end effector 8 to pivot backward (shown in FIG. 2C); (iii) pushing the label "CW" causes simultaneous clockwise rotation of knob 10, barrel 6 and end effector 8; and (iv) pushing the label "CCW" causes simultaneous counter-clockwise rotation of knob 10, barrel 6 and end effector 8. Movement in this embodiment is discrete and not proportional, although minor modification of control electronics (see FIG. 7) could enable such proportional control.

Figure 7:
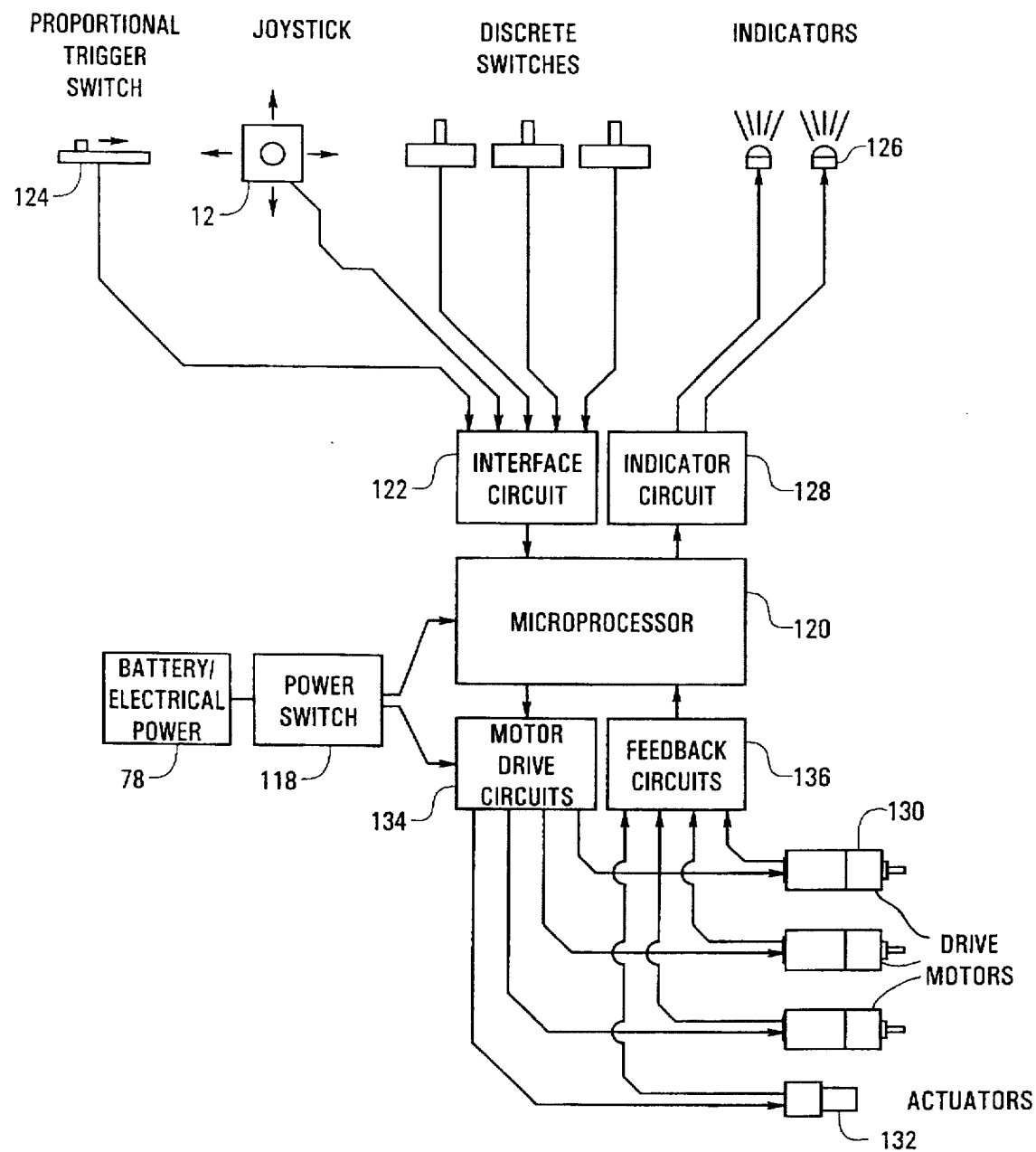
FIG. 7 is a schematic diagram depicting the integration of a microprocessor into the electronic embodiment of the instrument of the present invention.

FIG. 7 is a schematic diagram of a microprocessor controller and associated circuitry for use with the surgical instrument of the present invention. Each of the functional blocks may or may not be a discreet functional circuit. Input into the microprocessor 120 from the operator is through switches, variable resistors, encoders, or other devices (indicated generally at 12, 124). Depending on the type of component used, the microprocessor 120 may require an interface circuit 122. Similarly, the status indicator lamps 126 may also require some external drive circuitry 128. The motors or other actuators 130, 132 cannot be driven directly from the microprocessor 120; each requires a drive circuit 134 to regulate the power supply 78 to them. Feedback from the motors or actuators 130, 132 is provided by encoders or limit switches (not shown), controlled by and conditioned by a feedback circuit 136. In some instances, it may be desirable to avoid feedback control, relying instead on a feed forward system utilizing, for example, stepper motors instead of servo motors. Electrical power may be removed from the device via an electrical switch 118, providing on-off battery connection.

The present invention may incorporate a single board computer with microprocessor functionality equivalent to a Motorola 68HC11 processor with a programming language in internal ROM. The control software may be contained in EEPROM. The 68HC11 processor contains a section of EEPROM which is used to store set points, etc., while the instrument of the present invention is turned off. The single board computer is operationally coupled to a servo drive control module containing motion control ICs (for example, Hewlett-Packard HCTL-1000) which control the multiple drive motors 130. The selected microprocessor itself may be programmed to perform the servo control functions of the separate motion control ICs. Interfaces 122 also may be provided to decode the output of the joystick or switch 12 and proportional switches 124 used by an operator.

Now referring to FIGS. 8–17, the software for the instrument of the present invention is composed of a main loop 390 (FIG. 8B) which executes continuously while the instrument is switched on, and several secondary loops (FIGS. 9–17) which control special functions such as reciprocating, cutting or vibration and the like. One primary purpose of the main loop 390 is to query the joystick and other control switches to determine whether an operation is desired. If so, the appropriate subroutine is called. The main loop 390 runs every 20 milliseconds while the instrument is on and may be adapted to check continuously system operating parameters and update the displays, represented in FIGS. 8B and 17, respectively. The only way to exit the main loop 390 is to remove power from the instrument.

Motor movement is accomplished by the motor control chips which are run in the positional error mode. Relative and absolute positions are always maintained to assure repeatable movement and an absolute zero reference. The absolute positions are established during the initialization routines (FIG. 9), wherein motors are driven from limit to limit to establish an absolute zero reference point. Each motor movement is measured relative to a target position for that encoder, the position calculated by the microprocessor 120 (FIG. 7). The speed is multiplied by a gain factor used to allow a user to control distance sensitivity. If a position error ever exceeds an error limit, which is determined by motor limits during initialization (FIG. 9), then the main control loop 390 infers a component failure, declares an error and lights the appropriate lamp. Special functions such as reciprocating, cutting, vibration, autozero and barrel disengagement are handled in separate routines (FIGS. 12–16).

The handling of switch closure and joystick movement is straightforward. Because the movement routines are separate and distinct, the logic for each motor move is separate from another. However, because the main loop 390 executes so rapidly, the motion control ICs will accept destination positions and rates, and because the motors have mechanical inertia, the resulting motor movement is functionally concurrent. This allows simultaneous movement in all three axes. Other operator-changeable functions such as speed, force, and joystick sensitivity may be programmed by a suitable set of soft keys or dedicated buttons. Information may be displayed through the indicator lights or a display such as an LCD.

Figure 8:
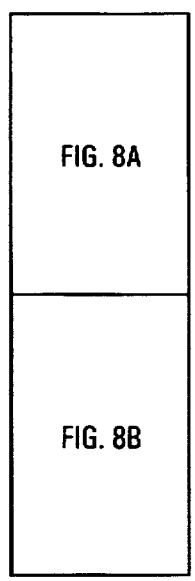
FIGS. 8–17 are flow diagrams depicting the operating of the microprocessor-controlled embodiment of the present invention.
Figure 8A:
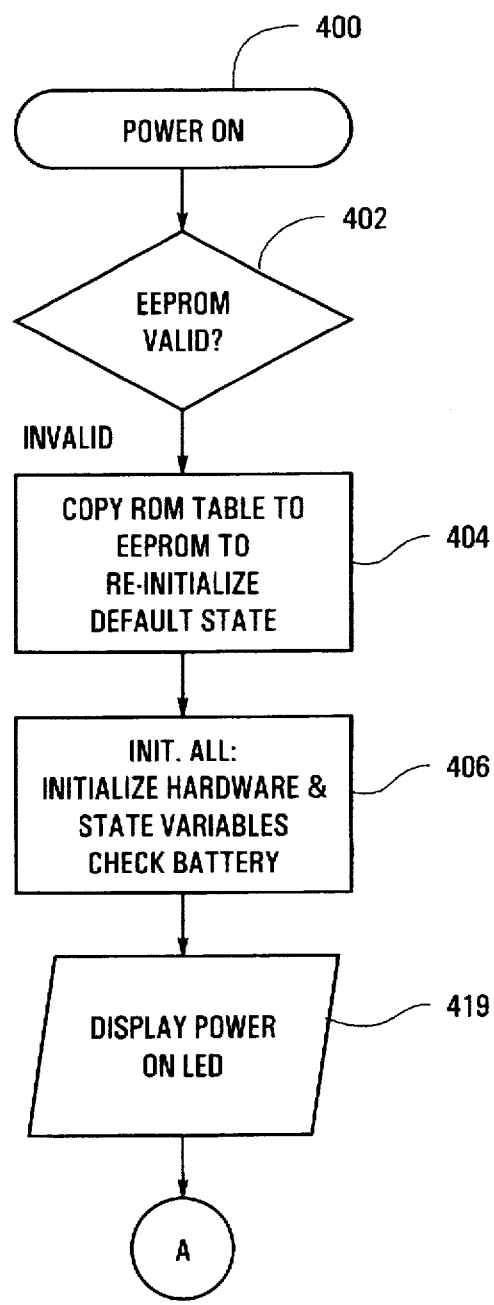
Figure 9:
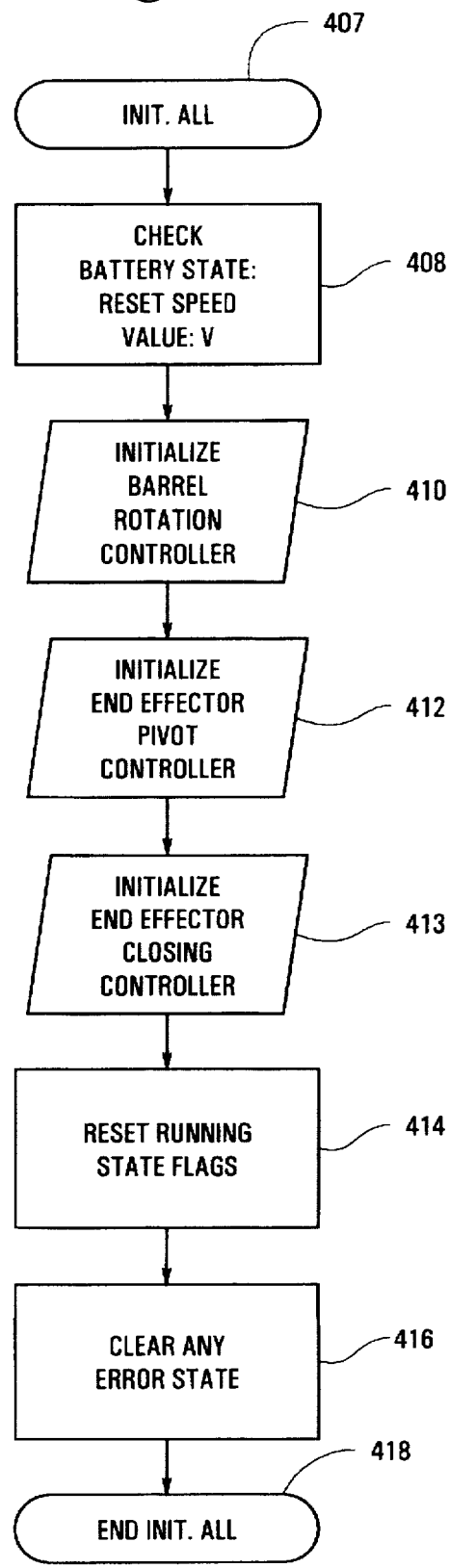

Operation of the instrument of the present invention is broadly depicted by the flow diagram of the main program loop for the microprocessor depicted in FIG. 8A and 8B. Power is provided to the instrument at block 400. The program proceeds through the EEPROM block 402 and re-initializes at block 404 if there is a default state. Initializing the hardware and stating the variables, as well as checking the battery occurs next at block 406. This operation is set forth in more detail in FIG. 9, beginning with initialize-all block 407 and proceeding to the check battery block 408, the barrel rotation controller 410, pivot controller 412, and end effector closing controller 413. The running state flags are reset at block 414, and any error is cleared at block 416. Initializing ends at block 418, at which point the program flows to the display power on block 419.

Figure 17:
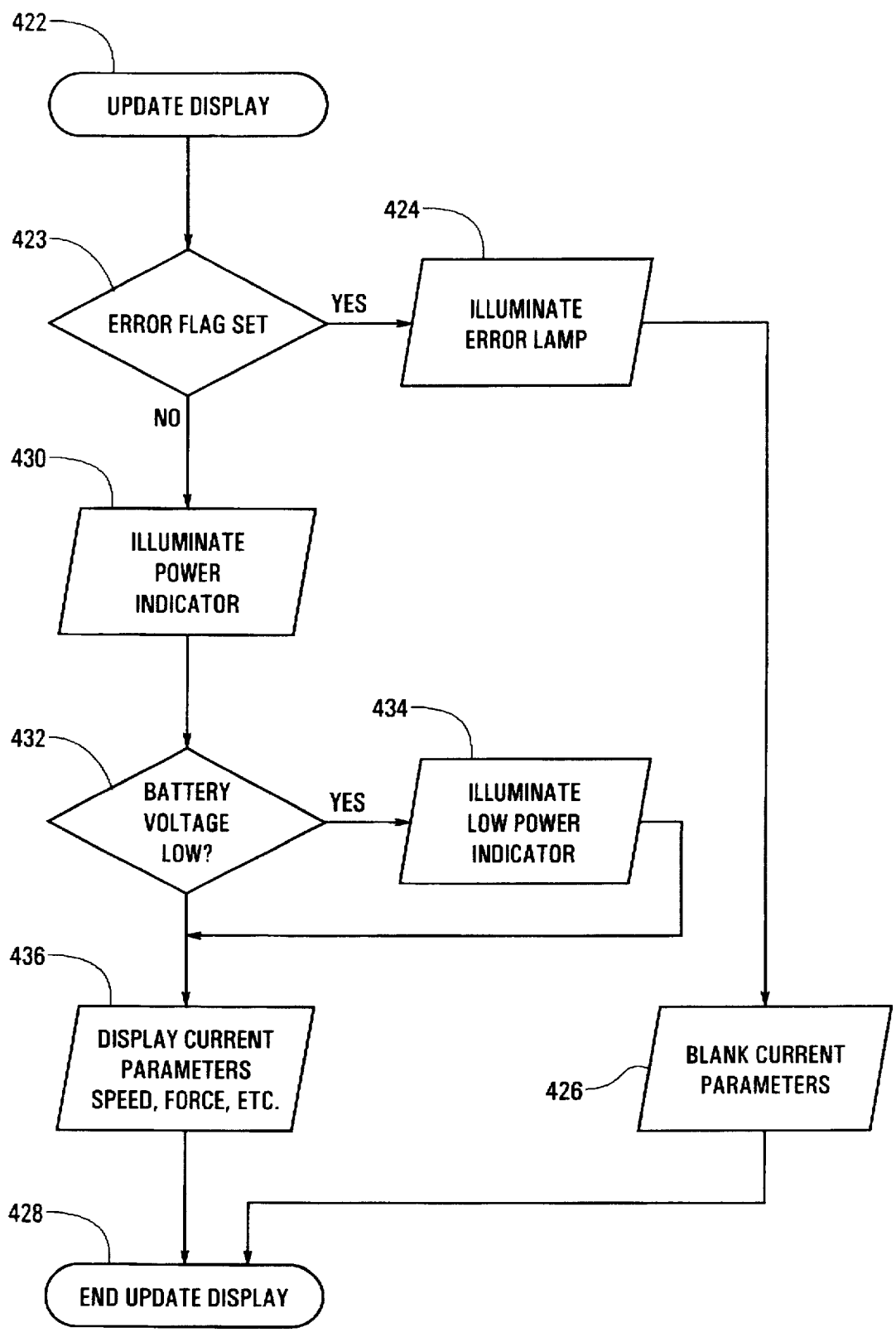

Referring now to FIG. 8B, after error query block 420, at block 421 the displays are updated, which is shown in more detail in FIG. 17, beginning at update display block 422. Initially, the error flag set query is made at block 423 and, if the answer is yes, the error lamp is illuminated as represented at block 424, current parameters are blanked, block 426, and the update display ends at block 428. If there is no error detected at block 423, the power indicators are illuminated, block 430, and a battery voltage query is made, block 432. If voltage is low, the low power indicator is lighted at block 434 and the flow proceeds to display current parameters (including operational parameters such as speed, force, etc.), block 436. At that point, the end display update program is reached at block 428.

Figure 10:
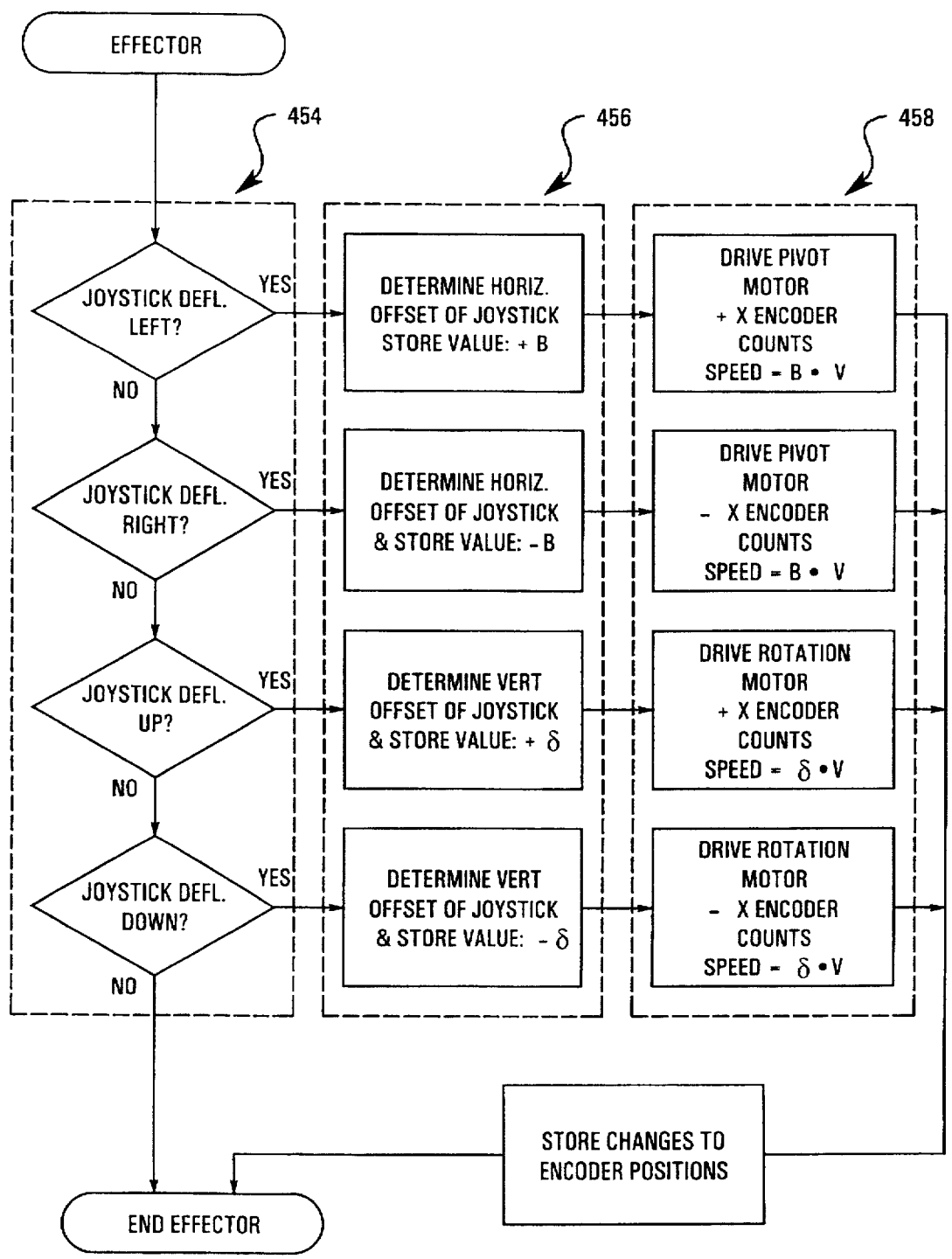

With further reference to FIG. 8B, if no errors are detected, use of the instrument may proceed to a specific inputs by the operator and queries by the program, such as the joystick query and movement blocks 450, 452, respectively. Referring to FIG. 10, the program flow controlling end effector movement is set forth in more detail as a series of queries and comparisons indicated generally at blocks 454, 456, respectively, and input operational commands indicated generally at block 458.

Figure 11:
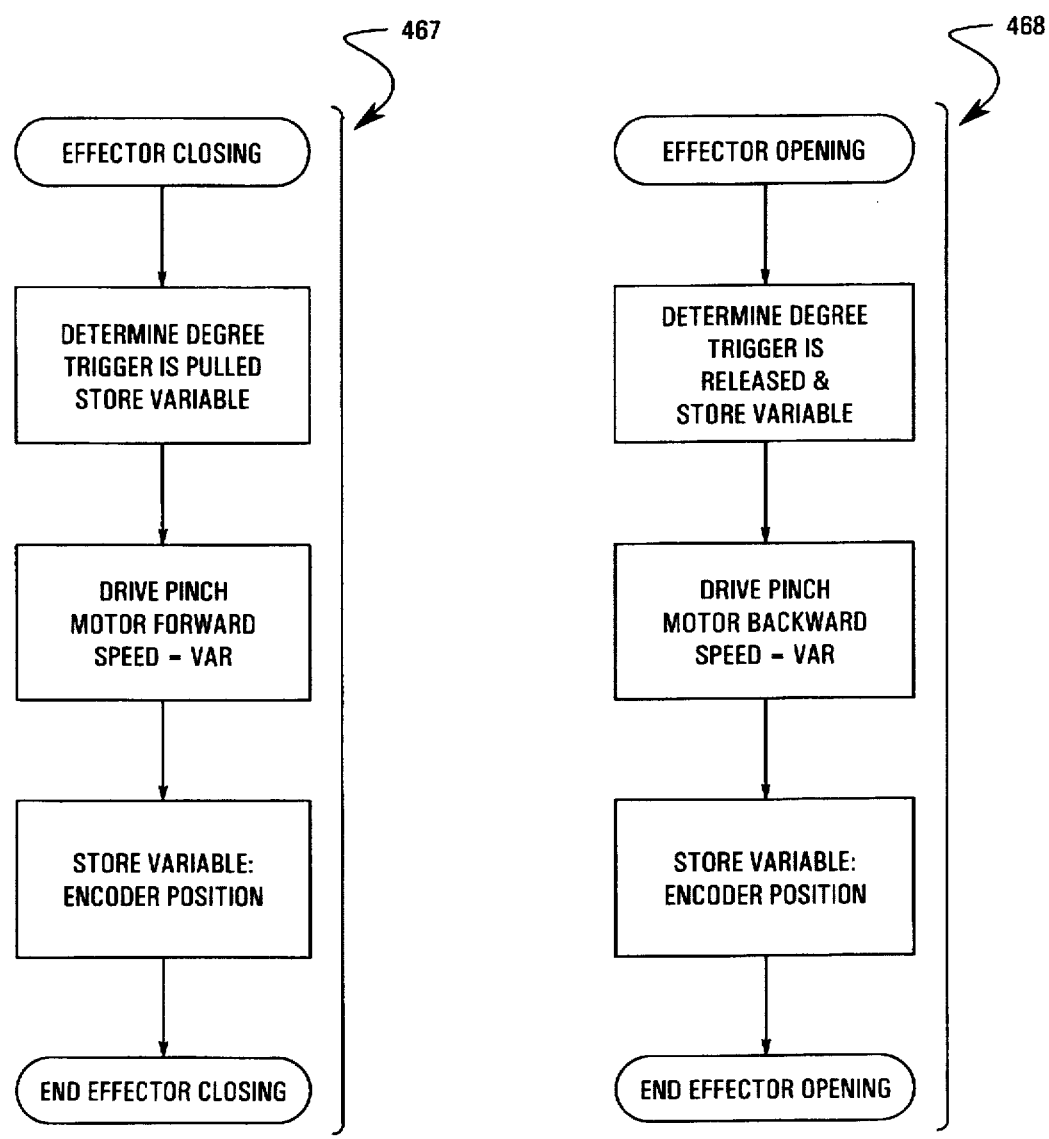

Similarly, the trigger switch 124 (FIG. 7) is monitored at the trigger query blocks 460, 462, (shown in Fig. 8B) resulting in end effector closure function blocks 464, 465 and 466. FIG. 11 depicts the end effector closing and opening sequence in exploded views at blocks 467 and 468, respectively.

Figure 12:
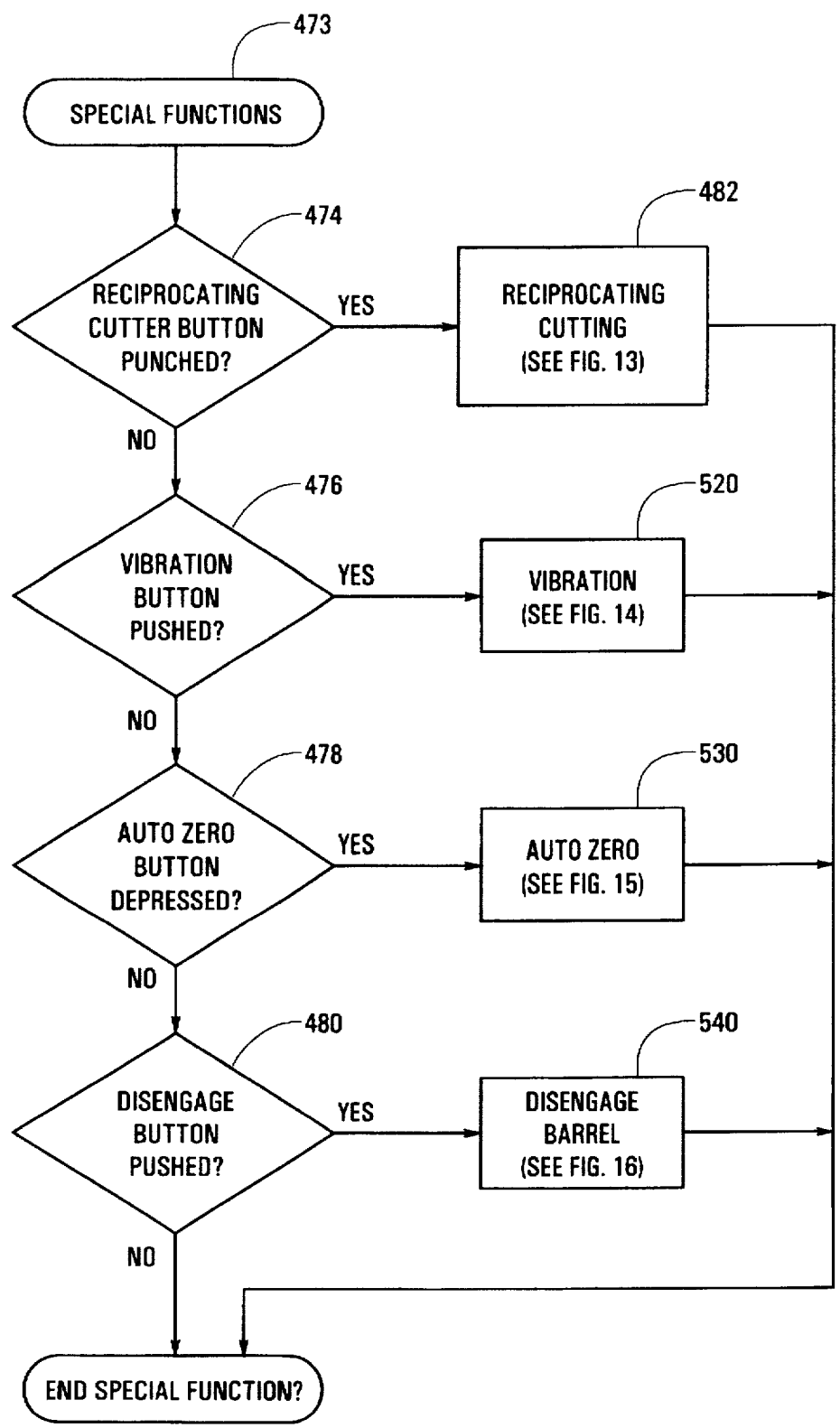

FIG. 8B reflects that the program includes a special function query, block 470, which, if a special function is required and actuated, directs the flow to block 472, set forth in further detail in FIG. 12. Block 473 begins the special functions flow then proceeds to query each of the special functions including reciprocating cutting, block 474, vibration, block 476, autozero, block 478, or the disengage function, block 480. With respect to the reciprocating query, if the answer is positive, flow proceeds to operational reciprocating cutting block 482, shown in more detail in FIG. 13.

Figure 13:
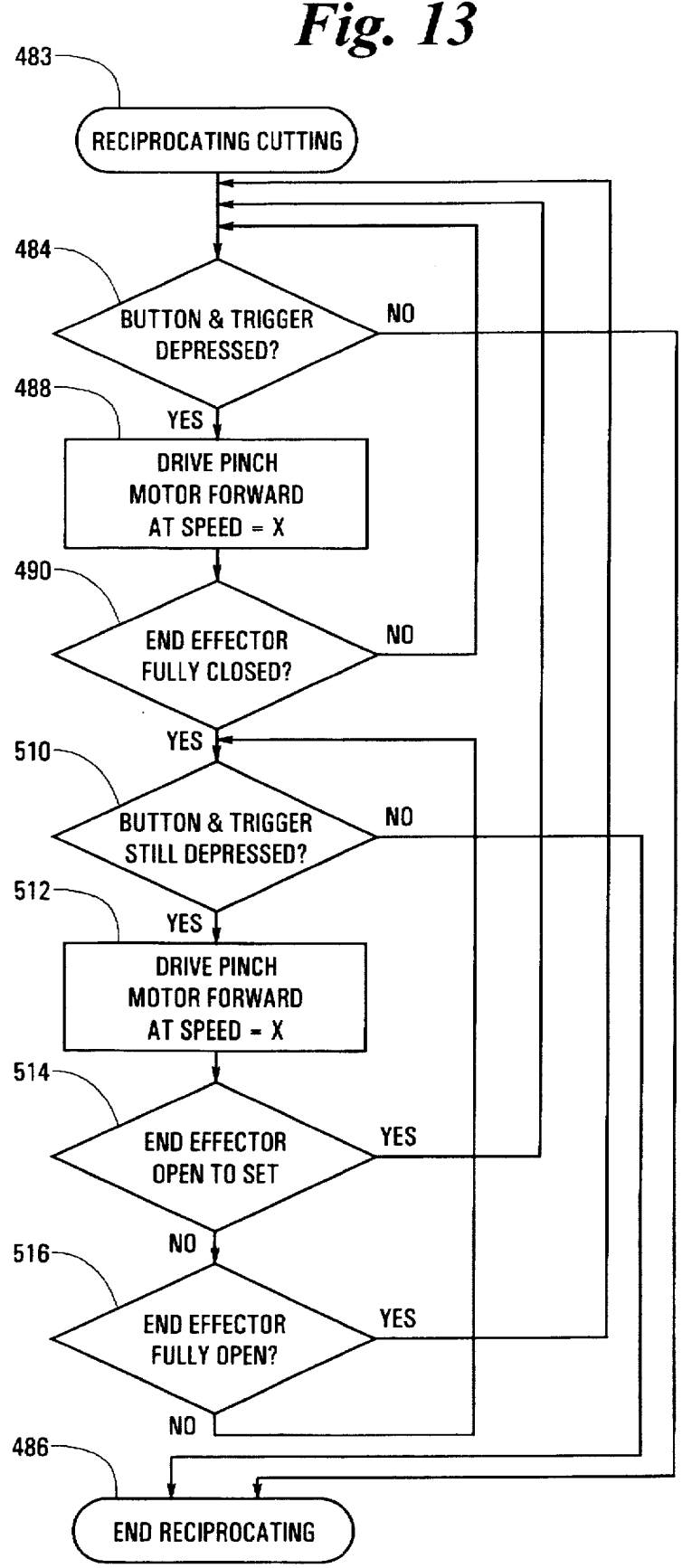

Referring to FIG. 13, the reciprocating cutting flow begins at block 483 and first queries whether the function has been requested at block 484. If the answer is no, the flow proceeds to end reciprocating, block 486. If the answer is yes, the motor is driven fully forward, block 488. The flow then proceeds to query whether the end effector is fully closed, block 490. If the answer is no, the program returns to the beginning, and if the answer is yes, a query is made as to whether the request button is still depressed, block 510. A negative response directs the flow to end reciprocating, block 486. If the answer is yes, the motor is operated, block 512, and the end effector is queried, block 514. If the answer is yes, the program returns to the beginning and, if the answer is no, a query is made as to whether the end effector is fully opened, block 516. If the answer is no, the program returns to the start point until the fully open state is reached.

Figure 14:
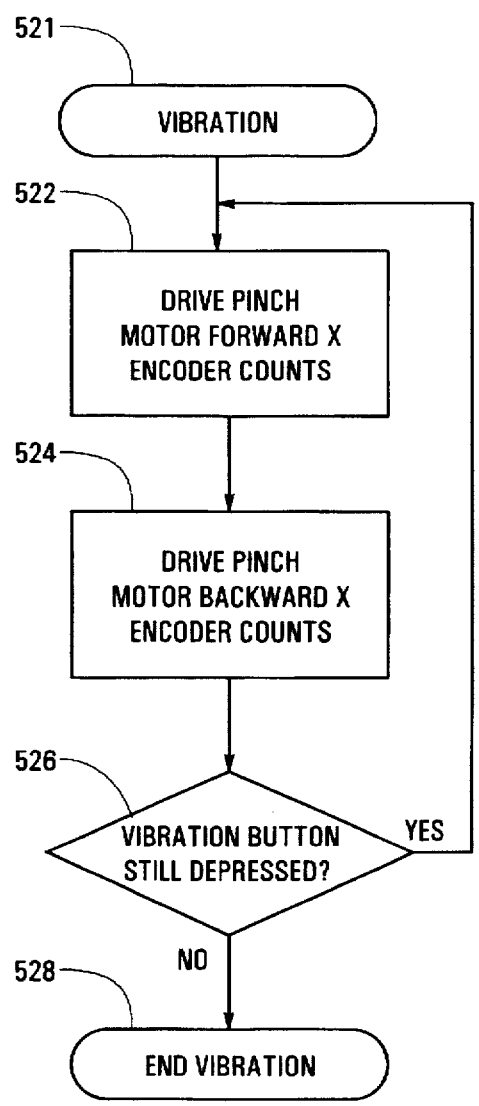
Figure 15:
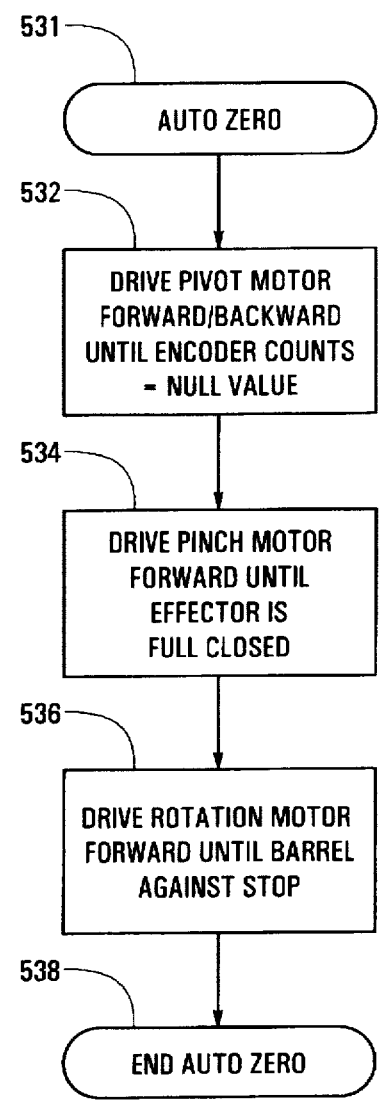
Figure 16:
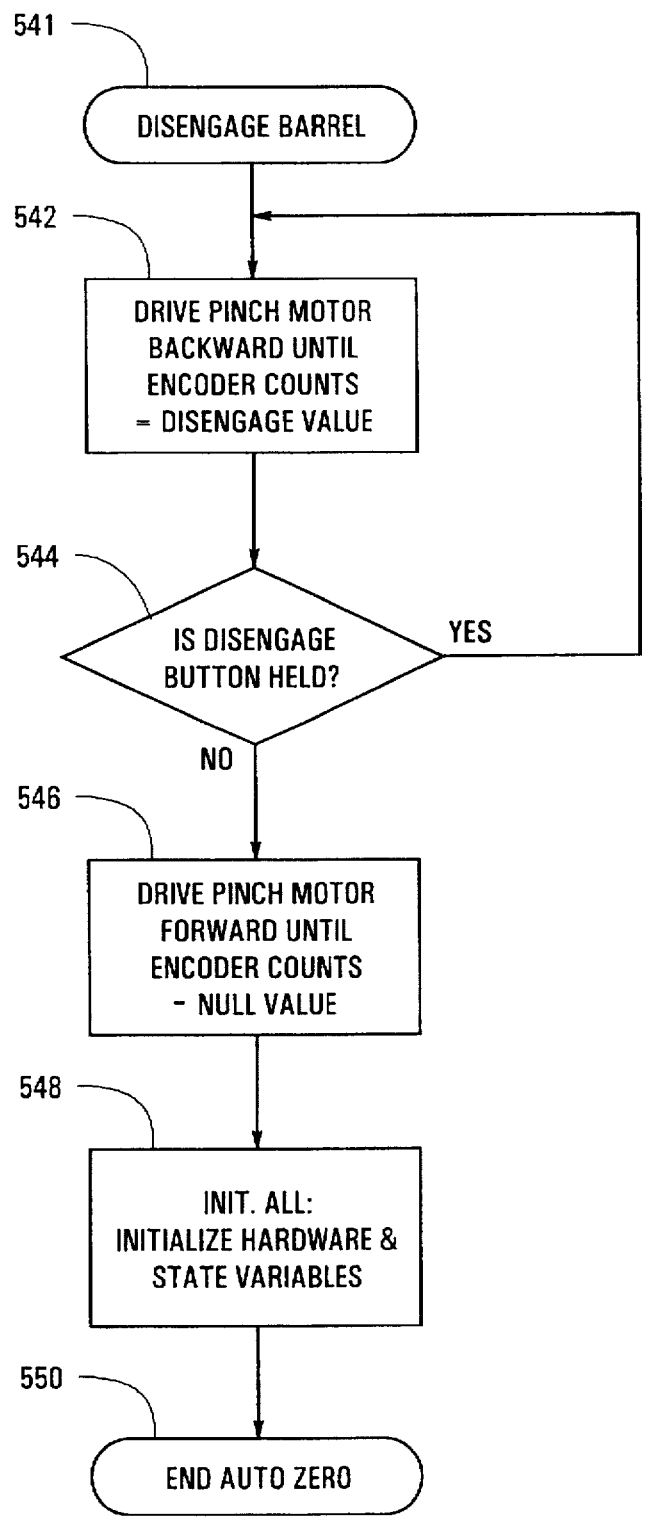

Referring back to FIG. 12, the vibration query at block 476 leads to the vibration function, block 520, shown in further detail in FIG. 14. Upon actuation of the vibration request, block 521, the flow proceeds to drive the pinch motor, either forward, block 522, or backward, block 524. The program then queries whether the operating request button is still depressed, block 526; if the answer is yes, flow returns to the start, and if no, the vibration flow ends, block 528.

Again referring back to FIG. 12, the special functions include the autozero query, block 478. If answered positively, the flow proceeds to autozero function, block 530, set forth in further detail in FIG. 15. Flow at block 531 and, if actuated, the program drives the pivot motor forward/backward until a null value is reached, block 532. Similarly, the pinch motor and rotational motor are driven until null values are reached respectively, blocks 534, 536, and autozero ends, block 538.

Returning to FIG. 12, another query in the special function begins at the disengaged query block 480. If the answer is yes, the flow proceeds to block 540, to disengage the barrel as set forth in FIG. 16. This function flow begins at block 541. Next, the pinch motor is operated to equal the disengage value, block 542. At that point, the program queries whether the disengage button is still depressed, block 544, and if the answer is yes, the program returns to drive block 542. If the answer is no, the pinch motor is driven forward until a null value is reached, block 546, and the program flows to an initial all block 548 wherein the hardware is re-initialized and variables stated, reaching the end of the autozero program, block 550. The main program flow (FIG. 8B) also includes a periodic check system function, block 560.

Figure 18:
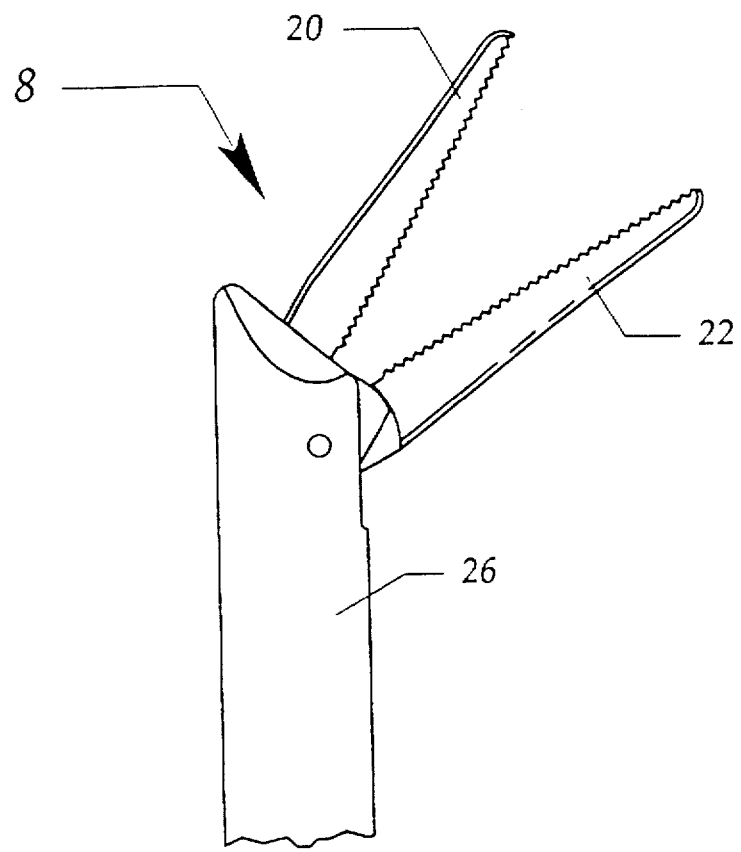
FIG. 18 is an elevational view substantially similar to that of FIG. 2, but depicting an end effector with dissection jaws.
Figure 19:
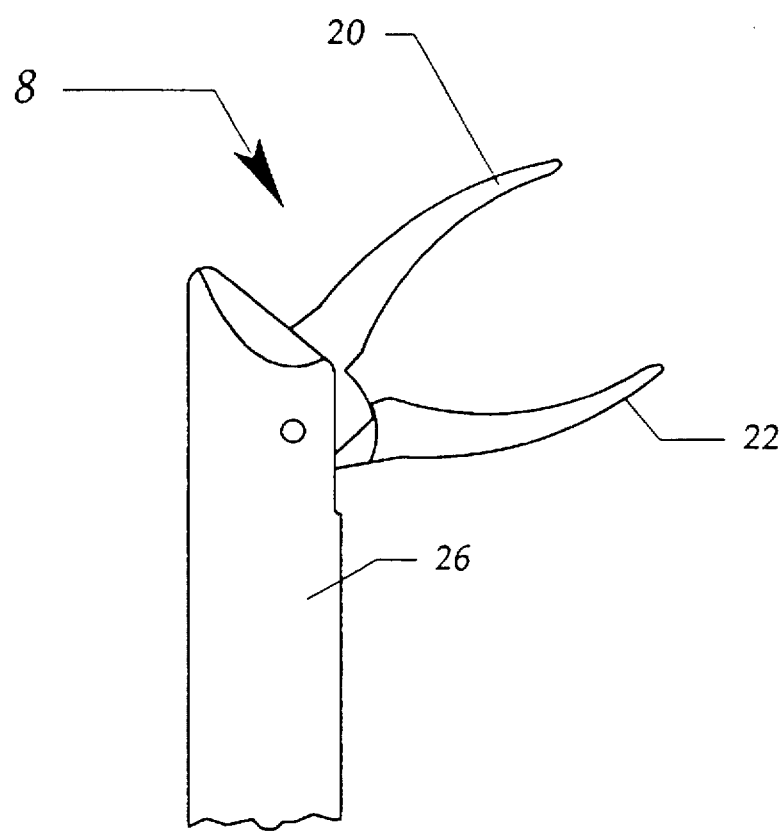
FIG. 19 is similar to FIG. 18, but depicting duckbill grasper jaws.

FIGS. 18 and 19 depict alternative embodiments of the present invention wherein the end effector 8, particularly the jaws or end effector pieces 20, 22 thereof, have a different shape. FIG. 18 shows a dissector end effector and FIG. 19 shows an traumatic grasper. These are representative of the various kinds of end effector pieces which may be attached to the end effector, and their operational aspects are substantially similar to the end effector depicted in FIG. 2A.

Figure 20A:
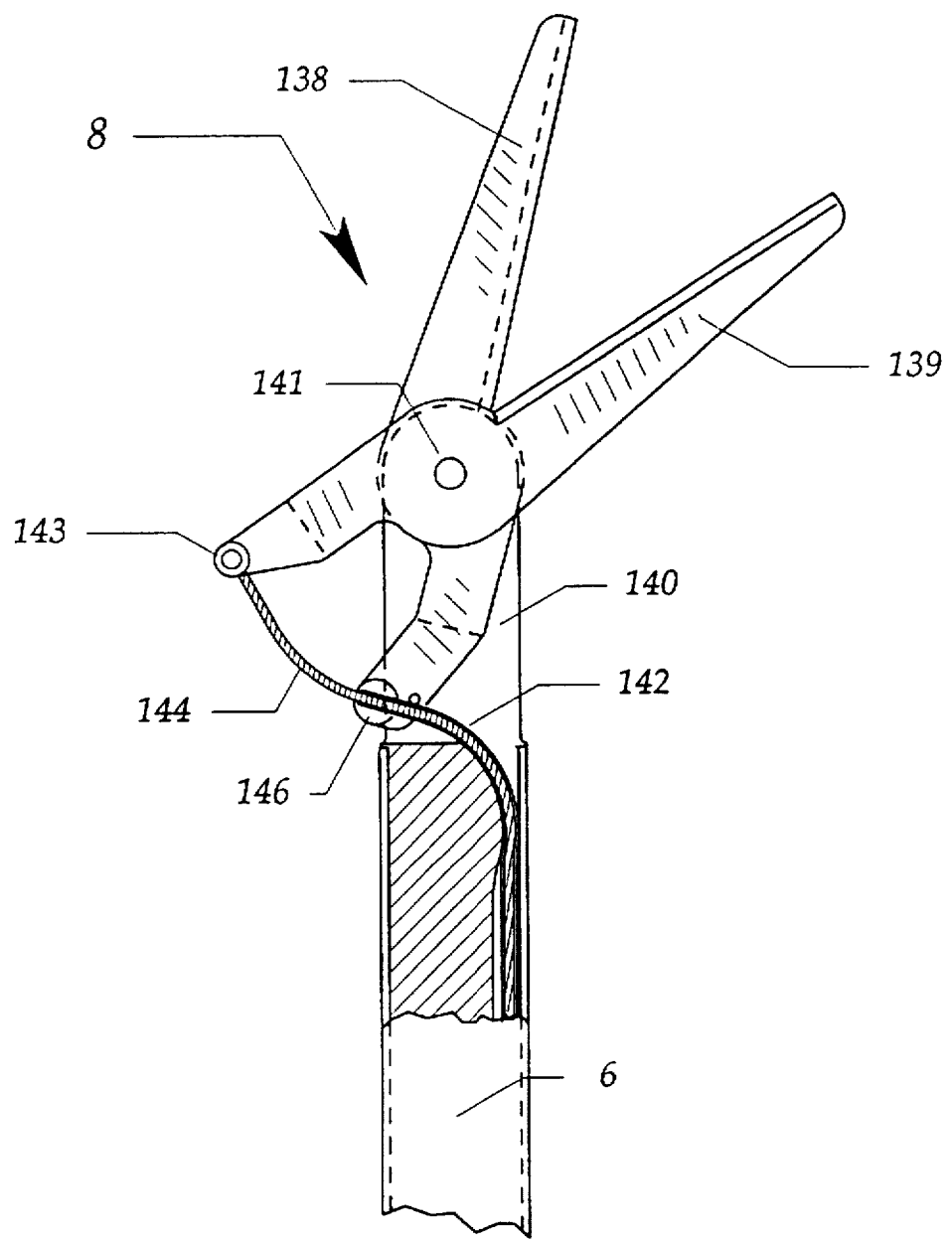
FIGS. 20A–C are elevational views, partially in section, depicting an embodiment of a control cable design of the end effector assembly utilizing solid, flexible tubing and a wire core as the control cable.
Figure 20B:
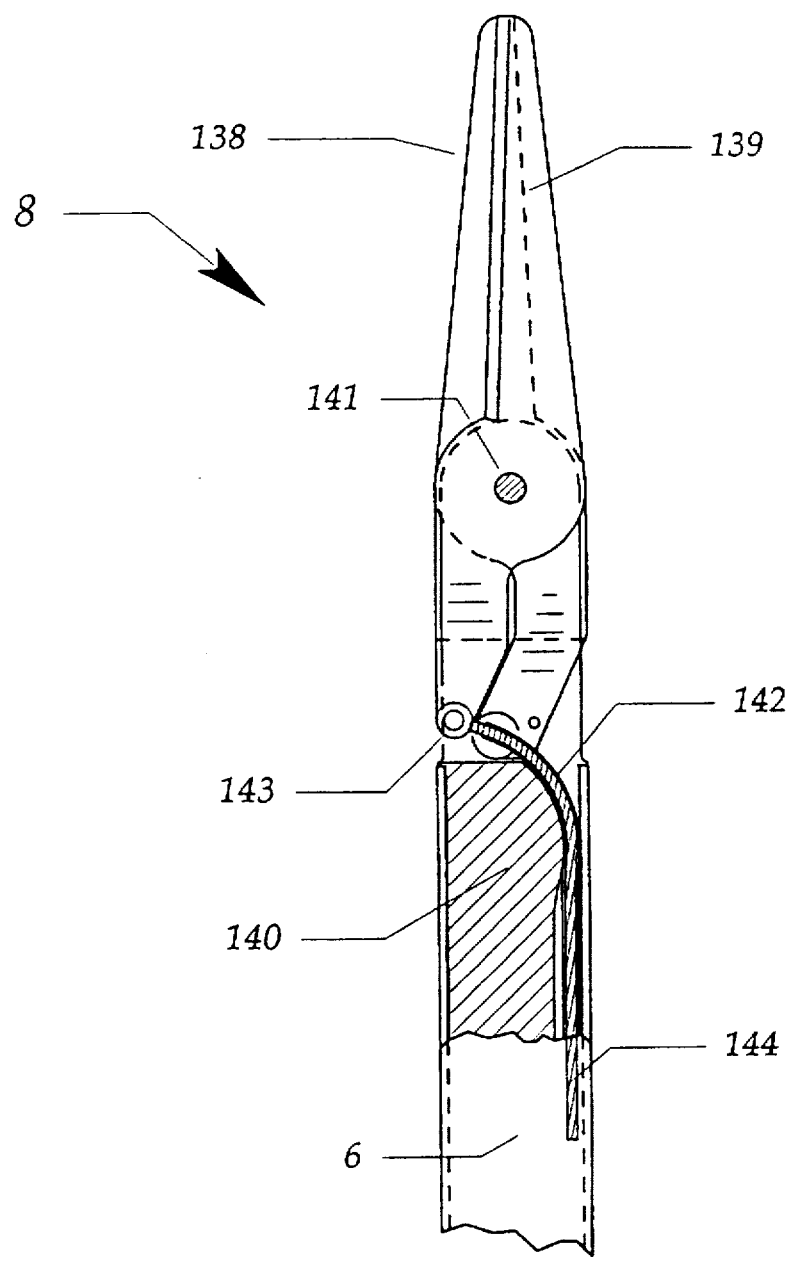
Figure 20C:
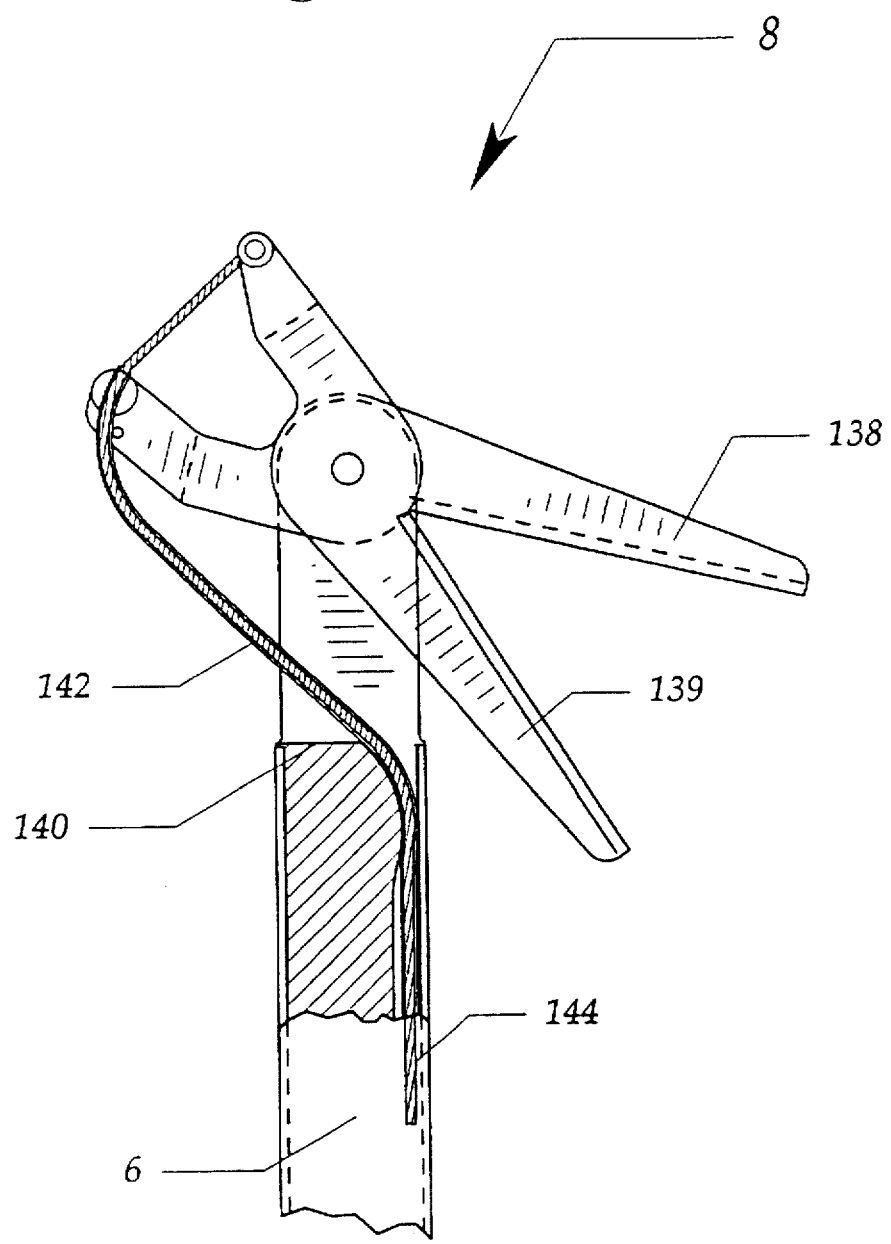

FIGS. 20A–C illustrate another embodiment of the end effector mechanism utilizing a control cable design. Two cutter end effector pieces 138, 139 are mounted pivotally in a fork 140 by a pivot pin 141. One elongated member, a super-elastic metal tube (e.g., drawn nickel-titanium), or sheath, 142 is attached to the proximal end of the end effector piece 138 via pivot 146. The sheath 142 depicted is a drawn tube, but a wound-wire or a suitable functional equivalent will work as well. The sheath 142 functions as a tension and compression member. A slot is formed within the clevis fork 140 so as to confine and guide the sheath 142; the slot is configured so as to define a radius which curves the tube approximately normal to the blade 138. Inside the sheath 142 is another elongated member which is a small diameter wire core 144 which is free to slide longitudinally within the sheath 142. The wire 144 is attached to the end effector piece 139 via pivot 143 and functions as a tension and compression member such that extension or retraction of the wire 144 causes opening and closing of the end effector pieces 138, 139 relative to each other as depicted in FIGS. 20A and B. Pivoting of the end effector pieces 138, 139 in unison while open or closed is accomplished by pushing the sheath 142 and wire 144 together in the distal direction, i.e., toward the end effector 8. This pushing causes the sheath and wire to extend or "snake" laterally relative to the end effector 8 as depicted in FIGS. 20A and C. Once positioned at an angle, up to and exceeding 90 degrees relative to the barrel 6 as depicted in FIG. 20C, opening and closing the end effector pieces 138, 139 is accomplished by pushing or pulling the wire core 144 relative to the sheath 142. Pulling the external sheath 142 would cause the end effector pieces 138, 139 to resume a straight-ahead position with respect to the barrel 6 of the instrument as depicted in FIG. 20B.

Still referring to FIG. 20A, the point of attachment of the sheath 142 and the wire core 144 to the end effector pieces 138, 139 may be a single point as shown or may take the shape of elongated slots with the point of cable connection being slidable within the slots in the proximal ends of the end effector pieces (not shown). The slots and the end effector pieces may be straight or curved in order to obtain a direct and fair lead of the sheath core 144, thereby minimizing bending and friction of the core 144 in its sheath 142. Additionally, the slots may be angled or oriented to provide increased leverage or mechanical advantage for the core 144 upon either opening or retraction.

A further simplification of the invention, shown in FIGS. 20A–C, is rigid attachment of the control cable core 144 to end effector piece 139 and of the sheath 142 to end effector piece 138. Elimination of the pivots reduces the complexity and number of parts. The wire core 144 may be fabricated as drawn metal wire, stranded wire or super-elastic alloy such as nickel-titanium. Suitable composite materials may be used as well. Similarly, the flexible sheath 142 of FIGS. 20A–C may be formed of a polymeric material or a super-elastic metallic alloy.

Figure 22:
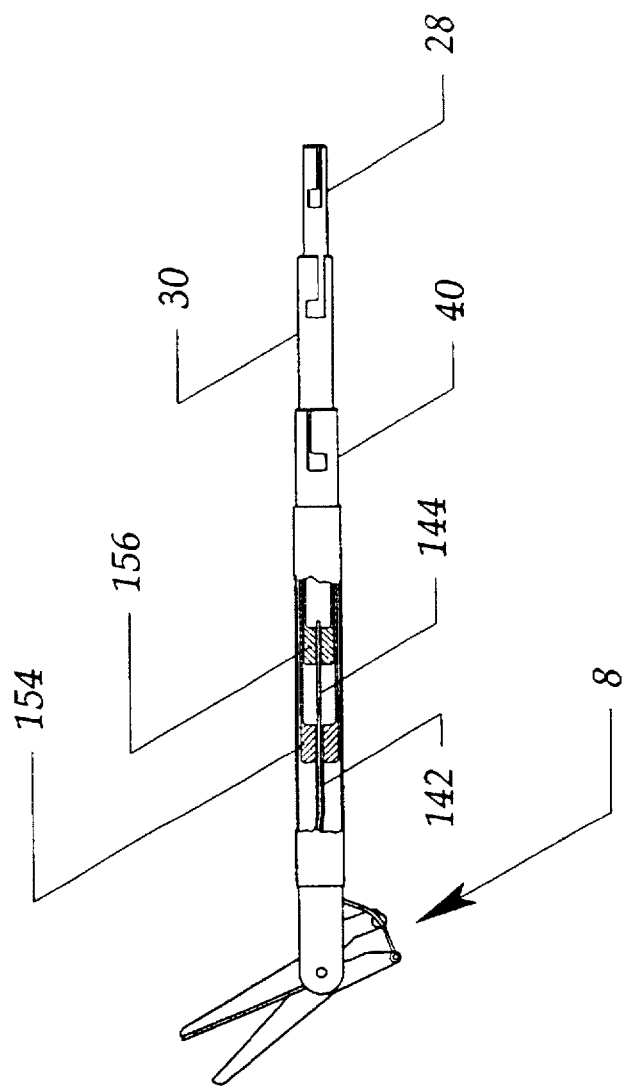
FIG. 22 is similar to that of FIG. 3, partially in section, and shows the connection between the control cable sheath and core to their respective control rods.

FIG. 21 shows an alternate embodiment of a controlcable technique for actuating the end effector 8. A flexible helically wound wire sheath 148 is used in place of the drawn nickel-titanium metal tube depicted in FIGS. 20A–C. A further refinement of this invention is the utilization of a slot, the bottom of which is curved with a defined radius in which the control cable sheath slides longitudinally. Now referring to FIG. 22, details of the interconnection of the wire core 144 and sheath 142 to the control rods 28 and 30 are illustrated. The proximal end of wire core 144 is attached to control rod 28 at junction 156. Similarly, the proximal end of sheath 142 is connected to control rod 30 at junction 154.

Figure 23:
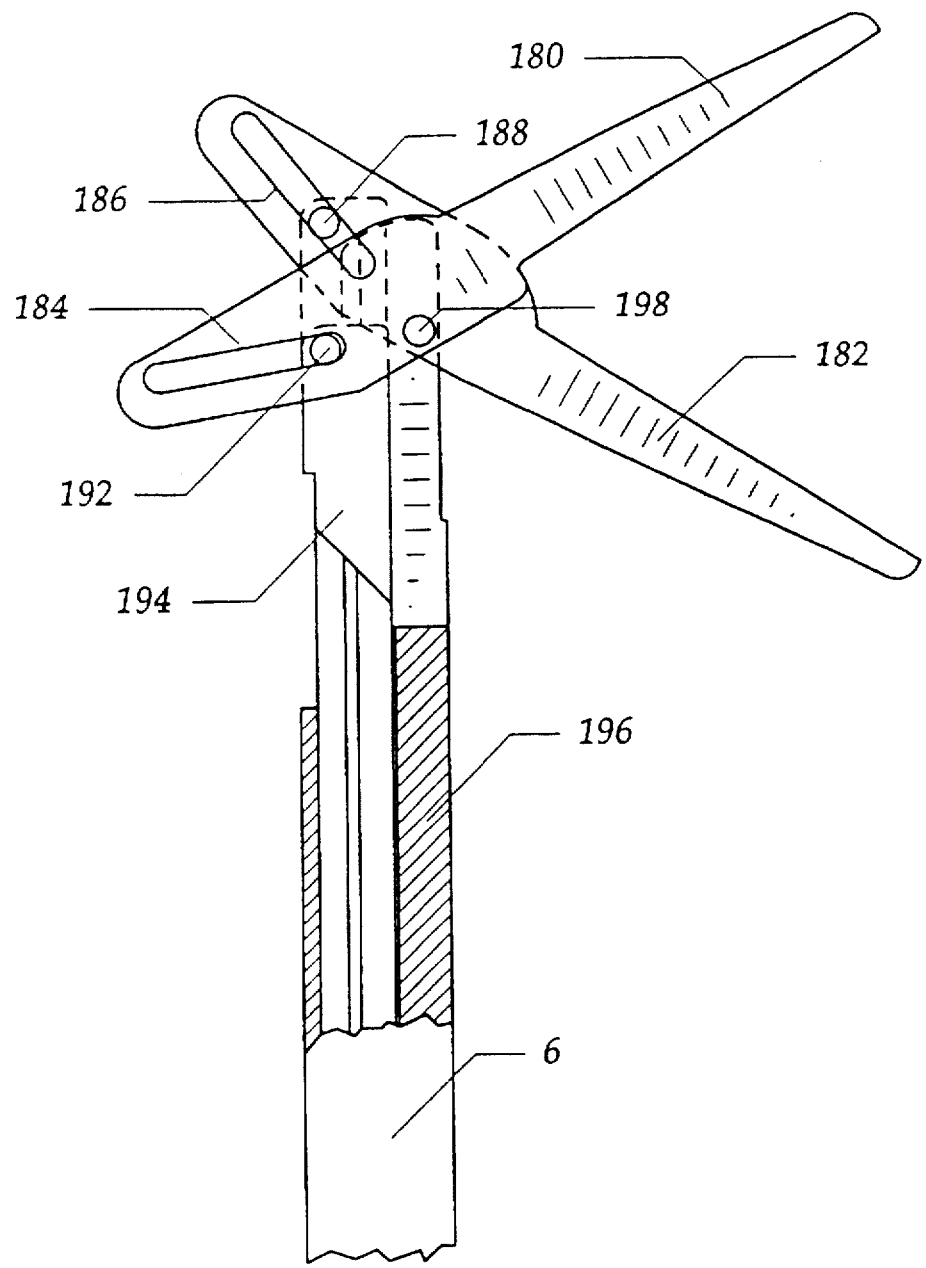
FIG. 23 is an elevational view, partially in section, of another embodiment of the present invention wherein the end effector assembly incorporates a pair of longitudinal sliding operational linkages.

FIG. 23 depicts yet another embodiment of the end effector. As in the previous descriptions, two end effector pieces 180, 182 are attached to clevis fork 196 by way of a transverse pin 198 around which the end effector pieces pivot freely. Each end effector piece has a "tail" protruding in the proximal direction which acts as a lever for pivoting the end effector pieces. Each proximal portion of the end effector pieces 180, 182 has an elongated slot 184, 186 each engaging one of two clevis pins 192, 188 attached to the distal end of two elongated control rods 190, 194 (190 shown in FIG. 24B). The two control rod geometries are mirror images of one another. Referring back to FIG. 23, moving control rod 194 in the proximal direction causes pin 192 to slide down slot 184, causing end effector piece 180 to rotate counterclockwise. Pivoting the end effector pair back is accomplished by pushing both control rods 190 (see FIG. 24B), 194 in the distal direction. "Snipping" action is achieved by pushing rod 194 while pulling on the opposite rod 190. Pushing the rods to the extreme in the distal direction causes the pins 188, 192 to progress up the slots toward the pivot pin, then down the slots away from the pin, causing the end effector to pivot back more than 120° from straight.

The end effector in the closed and straight position is shown in FIG. 24A. FIG. 24B is an end view of the barrel from the distal end of the instrument and depicts the end effector pieces 180, 182 opened slightly with respect to each other and pivoted about 20° with respect to the barrel. An important feature of this invention is the control rods 190 and 194 which interlock with the tubular barrel 6 and fork 196, allowing longitudinal sliding yet resisting twisting which results from the off-center load imposed by the pins 192, 188 (shown in FIG. 23). An advantage of this embodiment is that because the control rods 190, 194 form a large part of the tubular cross section, they can be strong in both bending and stiff in axial loading. The result is that the mechanical linkages are very robust and resistant to flexing or springiness. Although movement of the rods 190, 194 and end effector pieces 180, 182 is quite non-linear with respect to angular position, this non-linearity is easily overcome by correcting linkages in the handle.

Figure 25:
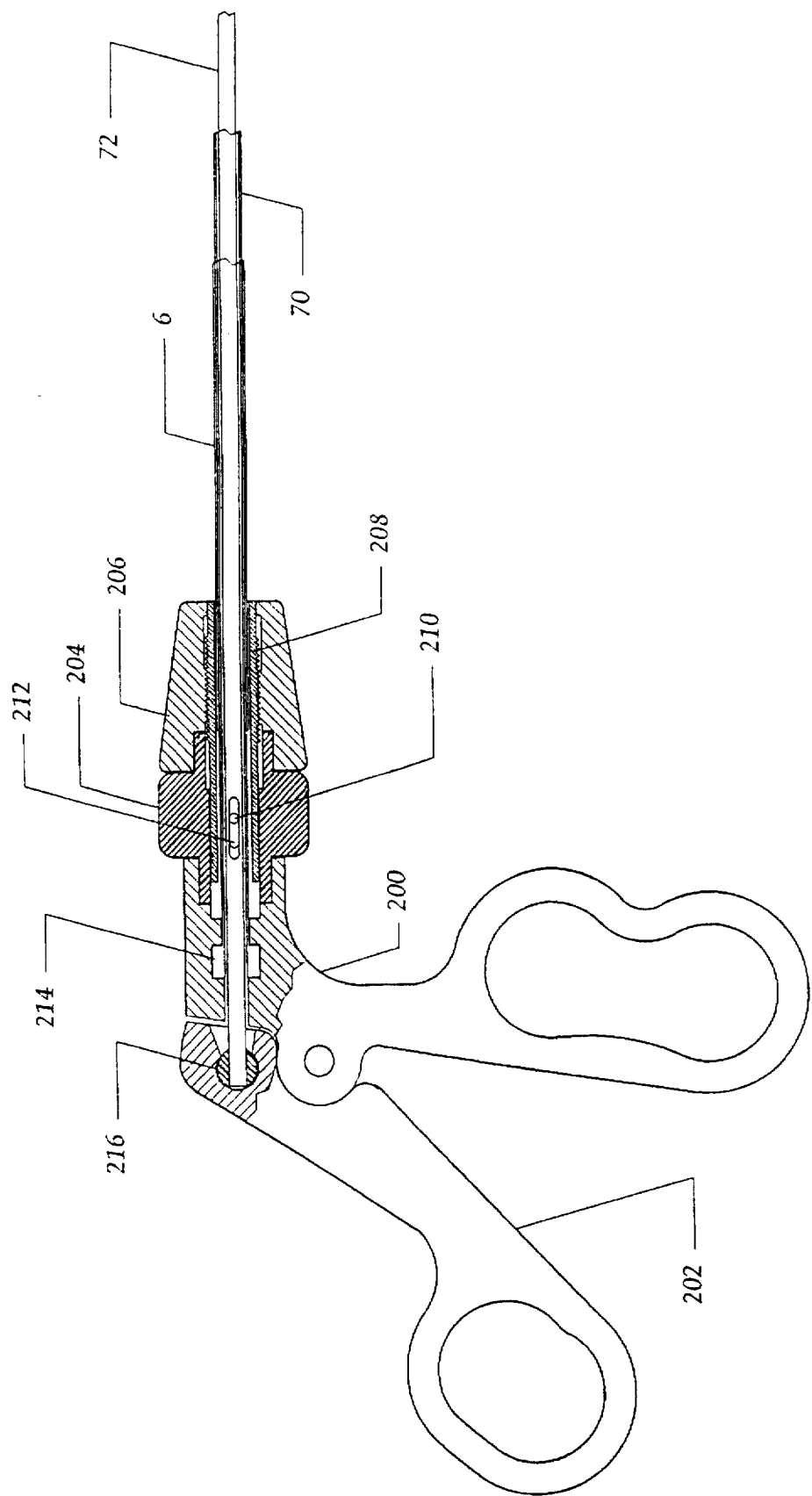
FIG. 25 is an elevational view, partially in section, of a manually operated handle for use with the present invention.

FIG. 25 shows a simplified, entirely manually operated handle of the present invention. This handle, along with the barrel 6 and control members 70, 72 attached thereto, is removably attached to the end effector assembly 9 shown in FIG. 3. For clarity in illustration, the disconnect mechanism shown in FIGS. 4A–C has been removed, and is not shown. This embodiment of the invention is a simplification because instead of relying on synchronized movement of the control rods 70, 72, it holds the control rods 70, 72 fixed and pivots the end effector pieces by translating the barrel tube and clevis fork instead.

Referring to FIG. 25, handle 200 is held by fingers such that the thumb can pivot lever 202. Closing lever 202 pulls clevis pin 216 in the distal direction. External control tube 70 is rotatably mounted in the handle, held captive by collar 214 such that it can not slide axially. Inner control tube 72 is rotatably attached to clevis pin 216 such that closing lever 202 draws tube 72 back relative to control tube 70, thereby closing end effector 8 shown in FIG. 2. Opening is the reverse, pushing on the control tube 72 instead of pulling. Pivoting is accomplished by twisting knob 206, thereby screwing threaded section of screw 208 in the distal direction. Screw 208 is attached to barrel tube 6. Moving the barrel tube 6 in the distal direction causes the clevis fork 26 (in FIG. 2A) to advance relative to the two control rods 70, 72 which are fixed, and thus results in the pivoting of the end effector. Screw 208 is prevented from rotating by pin 210. Rotation of the end effector 8 is achieved by twisting rotation knob 204. Pin 210 transects knob 204, control tubes 70, 72 and screw 208. Slot 212 through control rod 72 and screw 208 allows these elements to slide relative to handle 200 and knob 204. Control tube 70 has a simple hole for the pin 210 since it rotates with knob 204 but does not move axially. Thus, when rotation knob 204 is turned, the whole assembly (consisting of barrel tube 6, control tubes 70, 72, screw 208, pivot knob 206, and pin 210) rotates together. A friction device (not shown) between the handle 200 and rotate knob 204 is included to allow the user to twist pivot knob 206 without inadvertently turning rotate knob 204 and rotating the end effector 8.

FIGS. 26A–C depict an alternative embodiment comprising an entirely manually operated handle using a rack and pinion mechanism configured as a linear differential. It also can be used with a detachable end effector assembly 9 (e.g., FIG. 3), although the detachment mechanism is not shown in FIGS. 26A–C. Referring to FIG. 26A, the tubular barrel 6 is connected directly to a rotatable knob 254 on the distal end of the handle 4. The inner control tube 72 is coupled to the pinion yoke 250 to which pinion 240 is attached. The outer control tube 70 is connected to a second pinion yoke 256 to which pinion 242 is attached. Both pinions 240, 242 are identical and are free to rotate. Rigidly fixed in the handle is a rack 244 which engages the pinion 242. On the opposite side of pinion 242, and also engaging it is a second rack 248 which is slidable in the handle and is moved with a slide lever 252. The second pinion 240 also engages the slidable rack 248, and on the opposite side of this pinion is a third rack 258 which is attached to the trigger 2 and is also slidable with respect to the handle. In FIG. 26A, racks 244, 258 are shown end to end, but they could be placed side by side if shortening the handle is desirable.

FIG. 26B shows the function of pivoting the end effector. Sliding button 252 back in proximal direction as shown by the arrow causes pinions 240 and 242 to roll proximally, exactly the same amount, but half the distance the slide moves. This motion pulls control tubes 70, 72 back, causing the end effector to pivot back proportionally.

FIG. 26C shows the effect of pulling the trigger and thereby closing the jaws. In this case, moving the trigger back causes the rack 258 attached to the trigger to slide, moving pinion 240 attached to control tube 72 in the proximal direction. However, pinion 242 remains stationary because neither rack 248, nor rack 244 move. Thus control tube 70 stays stationary while control tube 72 moves in the proximal direction. The net result is closing of the end effector 8 as shown in FIG. 2A.

Referring back to FIG. 26A, rotation of knob 254 causes rotation of the entire end effector. In this way, the entire functionality of the instrument is manually controlled. The manual instrument potentially offers lower manufacturing costs and a similar degree of functionality and tactile feel to the user.

In the following, and in general reference to FIGS. 27–30, still another alternative embodiment of the entire surgical instrument will be described. This alternate instrument design includes an end effector 8, a barrel 6 and a handle 4, each of which will be described in detail below.

Figure 27A:
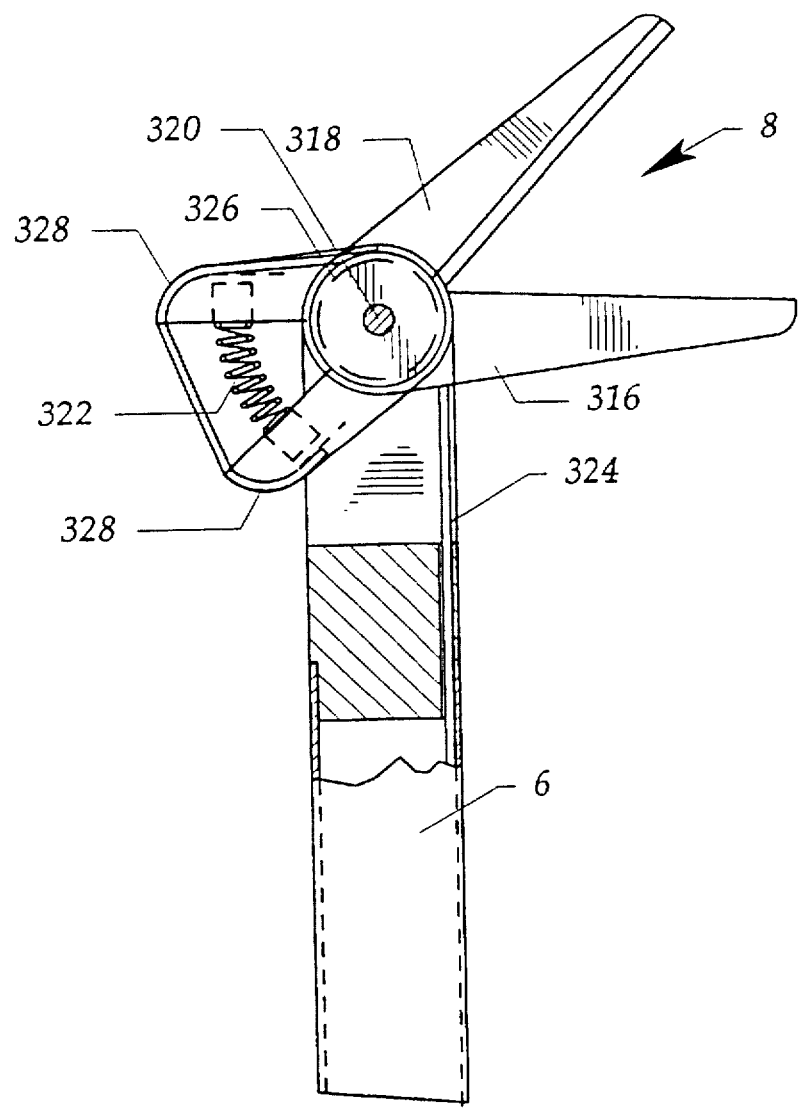
FIG. 27A is an elevational view of another embodiment of an end effector assembly of the present invention.

FIGS. 27A–C show enlarged views of the scissor-like end effector 8 of the alternate instrument design. In FIG. 27A the scissor end effector 8 is open and rotated 45° relative to the barrel 6. The scissor-like working end effector tip 8 comprises two end effector pieces (blades) 316, 318 pivotally attached to the barrel tube 6 by a pin 320. The end effector pieces 316, 318, as a pair, are rotatable 360° around the pin 320, and each end effector piece 316, 318 is rotatable 45° relative to the other end effector piece from a fully closed position (FIG. 27C) to a fully open position (FIG. 27A). The end effector pieces 316, 318, as shown in FIG. 27B, are parallel to one another, each having an adjacent flat face, which, when the tip 8 is closed, creates a shearing edge. FIG. 27B is a cross-sectional view of the scissorlike end effector 8 wherein the end effector pieces 316, 318 are closed and aligned with the longitudinal axis of the barrel tube 6. The two end effector pieces 316, 318 are biased toward the open position by a compression spring 322 (or torsion springs, not depicted). Two substantially identical control cords 324, 330 (only 324 is shown for clarity) are provided for closing the end effector pieces 316, 318 relative to one another and for pivoting the end effector pieces 316, 318 relative to the tubular barrel 6. The control cord 324 extends along the longitudinal axis of the barrel 6, over a pulley 326, which is free to rotate independently around pin 320, and along the back of the butt or proximal end 328 of the end effector pieces 316, 318. A polished radius is machined in the proximal end 328 of both end effector pieces 316, 318, for receiving the cord 324, which then spans the distance to the opposite end effector piece 318 where it wraps around a similar radius to the back of end effector piece 316, where it is attached. The second cord 330 (shown in FIGS. 28A–D) is similarly disposed, but, at the end effector, in a direction opposite to cord 324. Thus, cord 330 extends along the longitudinal axis of barrel tube 6 over a second pulley (not shown, but identical to pulley 326), which is free to rotate independently around pin 320, and along the back of the proximal end of the end effector piece 318. Cord 330 is received by a polished radius machined in the proximal end of end effector piece 318, spans the distance to the opposite end effector piece 316, where it wraps around a radius, is terminated and fixed in place.

FIGS. 28A–D depict the 3-dimensional movement available at the working end effector scissor-like tip 8. Each of the two cords 324, 330 extends parallel to the axis of the barrel 6 (line A) and is attached to one of two nuts 332, 334. The nuts 332, 334 are constrained by appropriate means, such as a key or spline, to prevent them from rotating in the barrel tube 6, but to allow their axial movement generally along the axis of the barrel 6. Each cord 324, 330 is attached to its respective nut 332, 334. Thus, cord 330 is directly connected to nut 334, and cord 324 passes through a hole in nut 334 and is connected to nut 332. A shaft 336 extends generally coaxially relative to barrel tube 6 and is threaded at its distal end. It is threaded with a standard (right hand) thread along a length 338 which exceeds the total desired travel of the cords 324, 330 as the end effector 8 is rotated from one extreme to the other. Equal lengths 338 and 340 of the shaft 336 are threaded in opposite directions. Rotation of shaft 336 in one direction causes nuts 332, 334 to advance together, and rotation in the other, opposite direction causes nuts 332, 334 to drive apart.

FIG. 28B shows the result of retracting the shaft 336 in the proximal direction, thereby pulling nuts 332, 334 and, therefore, cords 324, 330 simultaneously. The end effector pieces 316, 318 close relative to one another, but without rotation relative to the barrel tube 6. This is an important aspect of the invention because it allows the user to maintain the working end effector tip 8 at a constant angle relative to the axis of the tubular barrel 6, while still achieving activation of the end effector 8. When both end effector pieces 316, 318 are closed and straight, as shown in FIG. 28B, the profile of the entire device is within the profile required for passage through a relatively small laparoscopic surgical port or to access a tight area.

Figure 28C:
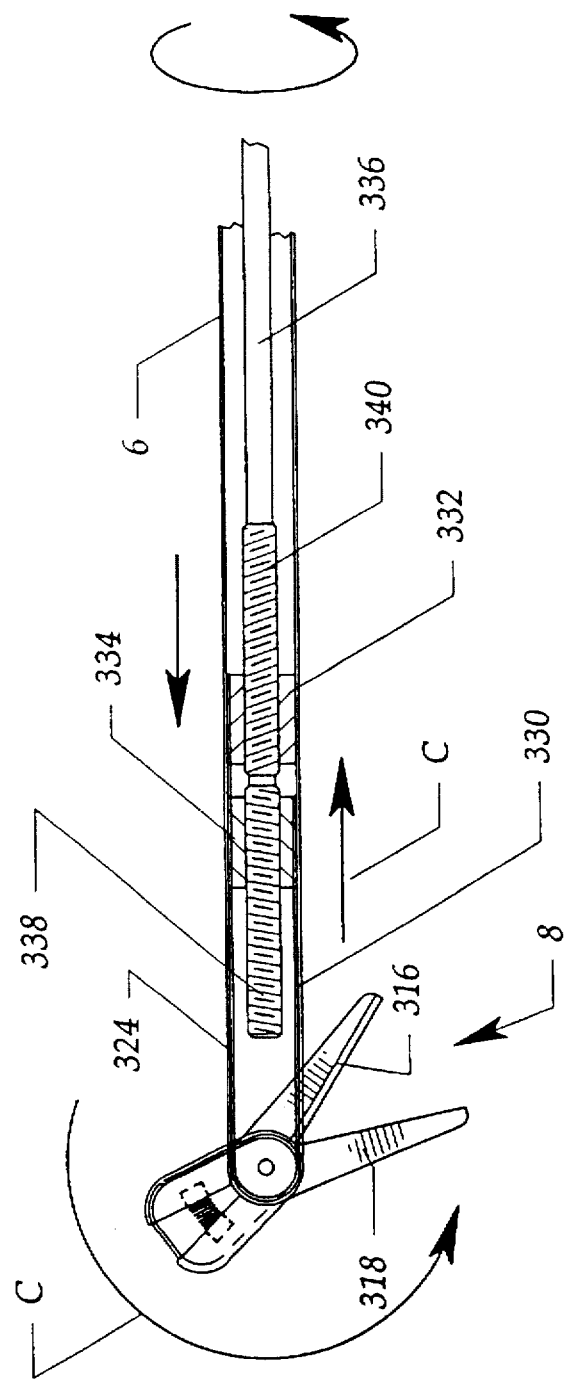
FIG. 28C is a view similar to that of FIG. 28A and depicts the pivoting of the end effector by rotation of the control linkage.

FIG. 28C shows the pivoting action (arrow C) of the end effector 8 as a result of rotation of shaft 336 inside the barrel tube 6. Rotating shaft 336 relative to barrel tube 6 causes nuts 332, 334 to drive together, pulling on cord 330 while releasing cord 324 exactly the same amount. This results in pivoting the end effector 8 in the plane of the axis of the barrel tube 6. It can also be seen that the pivoting of the end effector 8 is independent of the degree of closure of end effector pieces 316, 318. That is, the pivoting of end effector pieces 316, 318 is independent of how far shaft 336 is retracted in the proximal direction. This is useful because it allows a surgeon to control both closing and pivoting of end effector pieces 316, 318 independently, which allows the surgeon to selectively separate or cut tissue.

Figure 28D:
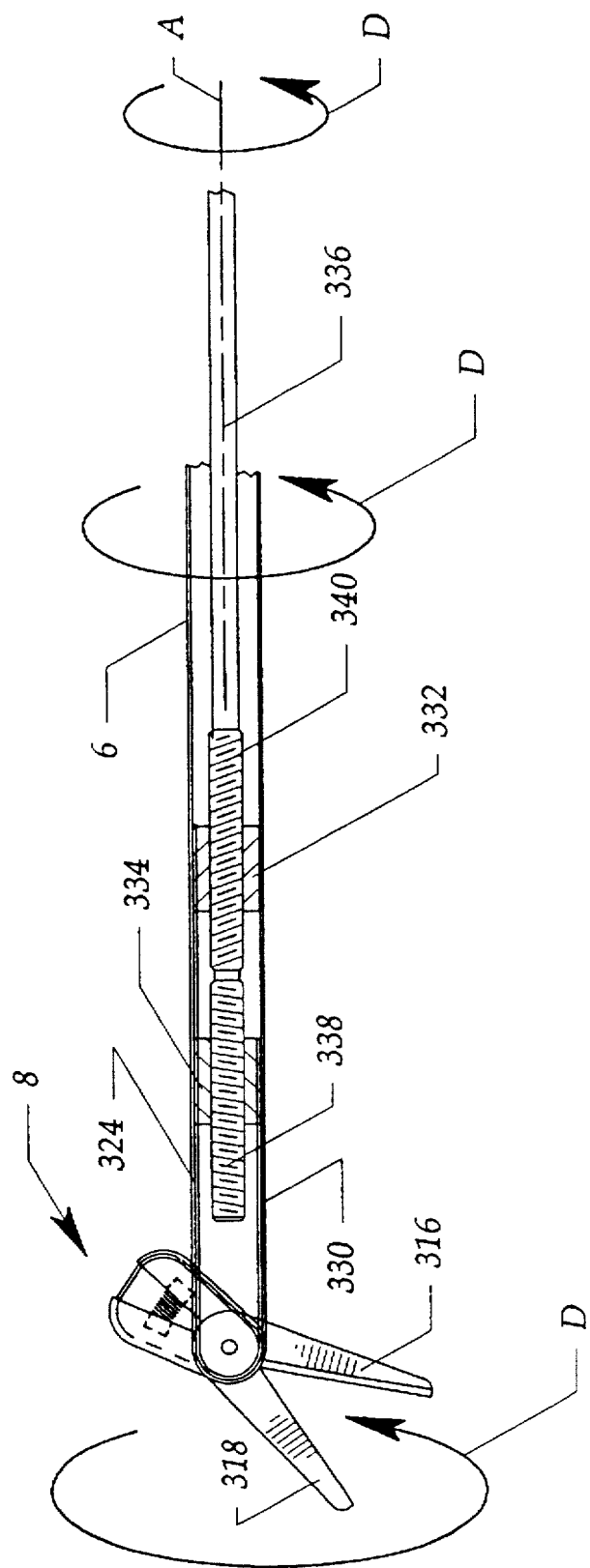
FIG. 28D is a view similar to that of FIG. 28A and depicts the rotation of the end effector and barrel.

FIG. 28D shows the rotational action of the end effector 8 as a result of simultaneously rotating both the shaft 336 and barrel 6 (arrows D). When both shaft 336 and barrel 6 are rotated in the same direction at the same rate, the nuts 332, 334 do not advance relative to the barrel 6 and no pivoting of the end effector 8 occurs. The net result is the simultaneous rotation of the barrel 6 and end effector 8 (arrow D). It can also be seen that closing of the end effector pieces 316, 318 is independent of the degree of rotation of the barrel 6 and end effector 8. This mechanism also has the advantage that the system has no orientation preference and the control cords 324, 330 cannot tangle or cross. This advantage is significant for interchangeable end effectors (including the detachable barrel 6 and selected end effector 8), because reattachment (i.e., plugging a selected end effector assembly 9 into the barrel or barrel 6 into the handle 4) does not require special orientation or locating of engagement structure.

Figure 29A:
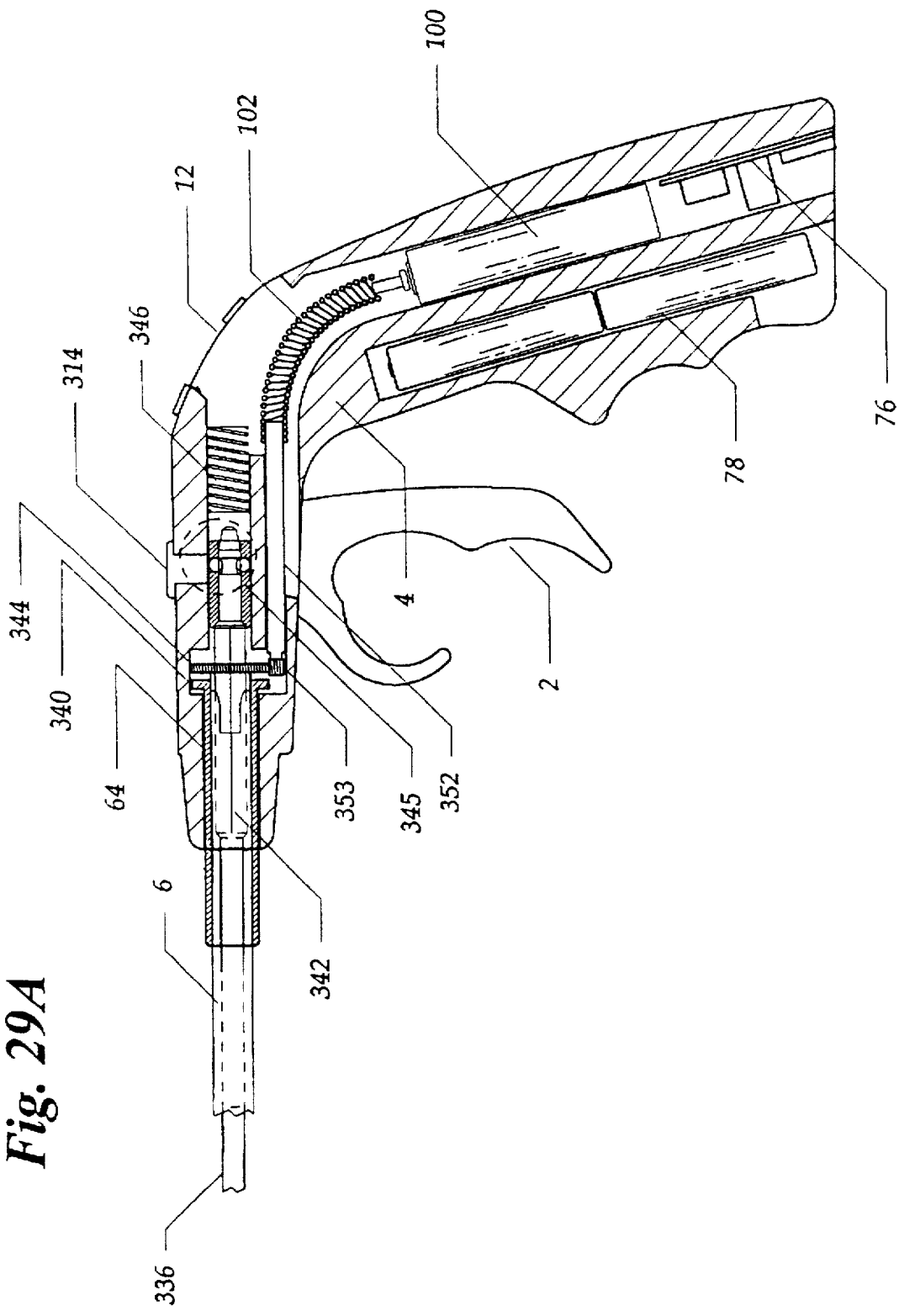
FIG. 29A is an elevational view, partially in section, depicting another embodiment of the handle for use with the present invention, with the barrel rotation mechanism removed for clarity.

Referring to FIG. 29A, details of the internal configuration of a handle 4 for use with the alternate design of FIGS. 27–28 are illustrated. Closing of the end effector is performed manually by retraction of a finger trigger 2. The barrel tube 6, which may be an integral part of an end effector assembly, is inserted into a receiving hole in handle 4, and is restrained. The proximal end of barrel tube 6 is forked, or fitted with an appropriate connection mechanism, such as a spline, resulting in positive torsional engagement with drive tube 64. Drive tube 64 provides for positive rotational driving of the tubular barrel 6 around its longitudinal axis. The proximal end 342 of shaft 336 is adapted (e.g., square or splined) to engage with gear 344, but slides through tube 64 to allow positive rotational driving of shaft 336, independently of drive tube 64 and the barrel 6. The shaft 336 is biased in the distal direction relative to the barrel 6. The shaft 336 extends through a collar 345 and is positively connected with it, whereby pulling of collar 345 in the proximal direction moves the shaft 336 in the like direction. The collar 345 is biased in the distal direction by a spring 346 and is connected to trigger 2 by a fork assembly (not shown) which allows free rotation of the shaft 336 and spline 342, but also enables the retraction of shaft 336. Pulling the trigger 2 causes closing of the end effector pieces 316, 318 (see FIG. 27A), and the amount of closure is directly proportional to the travel of the trigger 2.

Figure 29B:
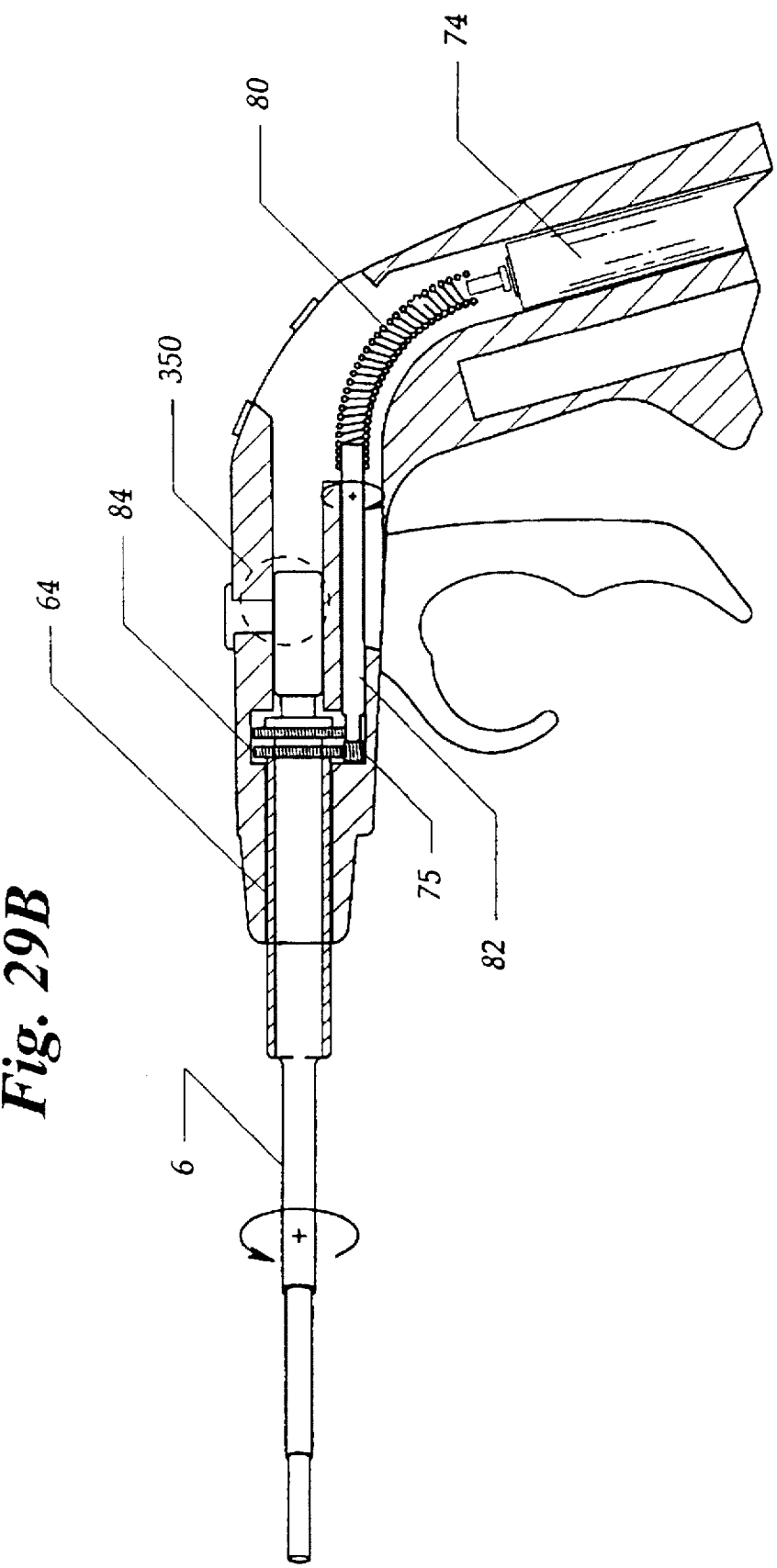
FIG. 29B is an elevational view similar to FIG. 29A showing the actuation which results in rotation of the end effector.

FIG. 29B is similar to FIG. 5D showing rotation of the end effector. Gear 84 meshes with pinion 75 on a separate shaft 82, driven through its own flex drive 80 and gear motor 74. In this way, gear motor 74 rotates the tubular barrel 6 of the end effector directly.

Referring to FIG. 29A, pivoting action is illustrated. Gear 344 meshes with the pinion 353 on shaft 352, driven through gearbox and motor 100. The two discrete motor and gear assemblies allow direct control of each independent axis of movement of the end effector 8. The two are mounted side-by-side in the handle. The motors 74, 100 (see also FIG. 29B) are controlled by a multi-positional joystick-type or push-button control switch 12 mounted on the handle 4 within comfortable reach of a user's thumb. Power for the motors 74, 100 is supplied by an integral, rechargeable or removable battery 78 (shown in FIG. 29A). Position of the end effector is controlled by microprocessor-based control electronics 76 (also shown in FIG. 29A), whose function and operation is described hereinabove in reference to FIGS. 7–17.

Figure 30A:
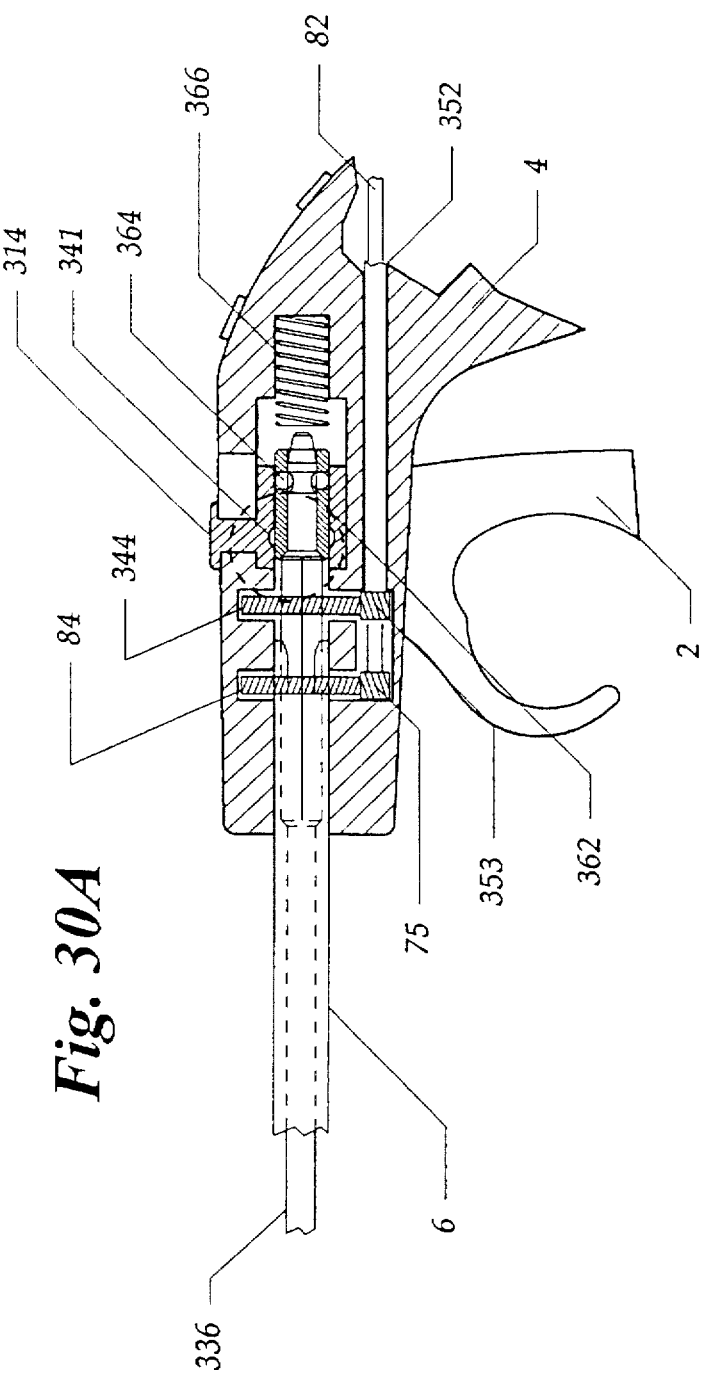
FIG. 30A is a fragmentary sectional view of a modified handle embodiment showing a coupling mechanism for attaching the end effector and barrel to the handle.
Figure 30B:
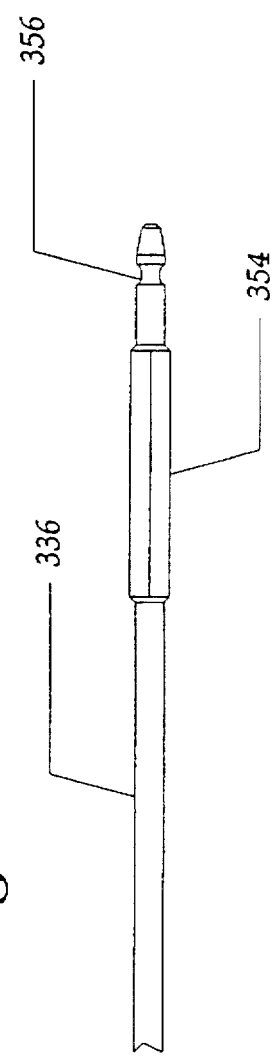
FIG. 30B is an elevational view of a portion of the control linkage of the present invention.

Referring to FIGS. 30A and B, the mechanism for attaching and detaching the barrel 6 from the handle 4 is depicted for the alternate instrument design. Specifically, in FIG. 30A the shaft 336 is retained in a generally cylindrical locking collar 362 slidably mounted in the handle 4. The collar 362 contains, operably and slidably, a spring 366, a set of detent balls 364 captured in holes in the collar and a trigger pin (not shown). The shaft 336 and barrel 6 are held in the handle 4 by the balls 364 which releasably engage in a detent ring 356 adjacent to the proximal end of the shaft 336 (see FIG. 30B, depicting details of the shaft 336, including the splined or square portion thereof), thereby locking the shaft 336 to the collar 362 axially, while allowing the shaft 336 to rotate. Referring back to FIG. 30A, moving the trigger 2 in the proximal direction retracts collar 362 and shaft 336, thereby opening and closing the end-effector tip 8.

Still referring to FIG. 30A, sliding the button 314 in the proximal direction slides a dog attached to the button 314 allows the barrel tube 6 and shaft 336 to be removed from handle 4 by sliding a set of detents 341 into such a position to allow balls 364 to move radially outward disengaging detent ring 356 from locking collar 362. In this manner, multiple tip assemblies (including the barrel 6 and a selected end effector) may be used with a single handle 4 and be safely and operably secured to the handle 4.

Figure 31A:
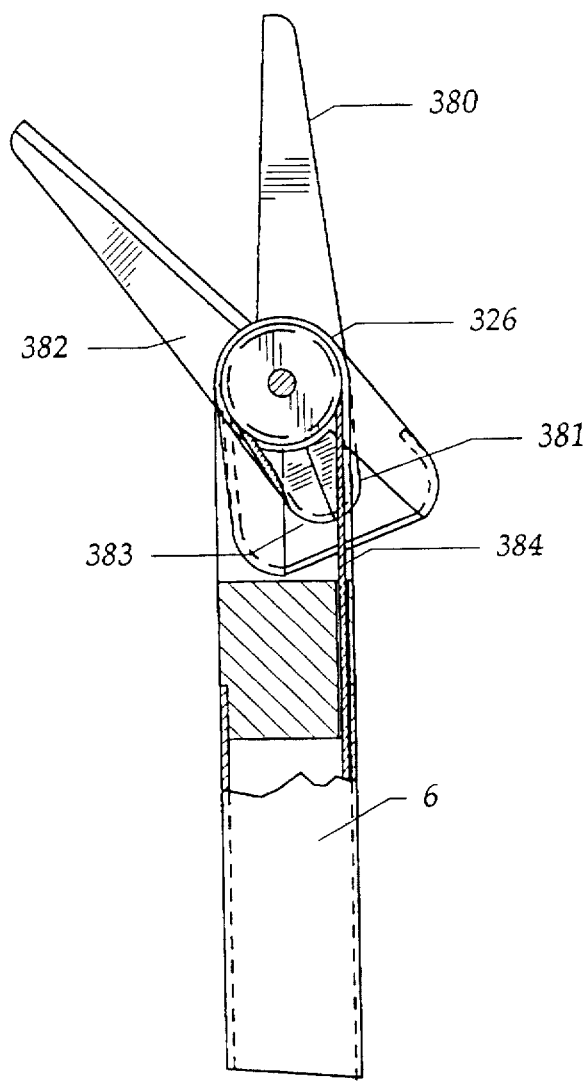
FIG. 31A is an elevational view of the distal end of an alternate form of the end effector assembly of the present invention with parts broken away for clarity.
Figure 31B:
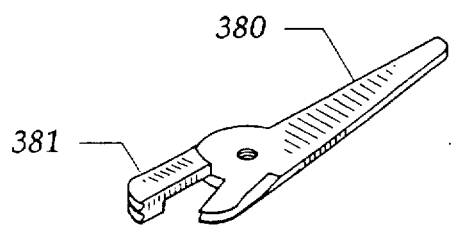
FIG. 31B is a perspective view of one jaw depicted in FIG. 31A.
Figure 31C:
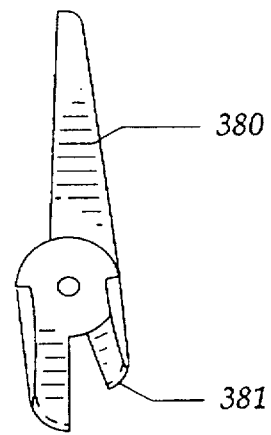
FIG. 31C is an elevational view of the jaw also depicted in FIG. 31B.

FIGS. 31A–C and 32A–B show alternative embodiments of the scissor-like end effector tip 8 depicted in FIGS. 27A–C. FIG. 31A shows an end effector similar to that shown in FIG. 27A, wherein two end effector pieces 380, 382 are operated or closed by a pair of cords (not shown) in a manner identical to that described above with reference to FIG. 27A. The principal difference in the two designs is that, as shown in FIG. 31A, another pair of cords 384, 386 (only cord 384 is shown) is used to open the end effector pieces 380, 382 instead of relying on a spring 322 to urge them apart, i.e., open, and end effector pieces 380, 382 have levers 381, 383. Cord 384 extends axially down barrel tube 6, wraps around pulley 326, extends along the backside of the lever on end effector piece 382 and connects to the lever on end effector piece 380. Pulling on cord 384 pulls the levers together, opening the end effector pieces 380, 382. One advantage is that the cords 384, 386 (not shown) enable positive opening of the end effector pieces 380, 382, whereby opening may be accomplished with greater force than is possible with the spring alone.

Figure 32A:
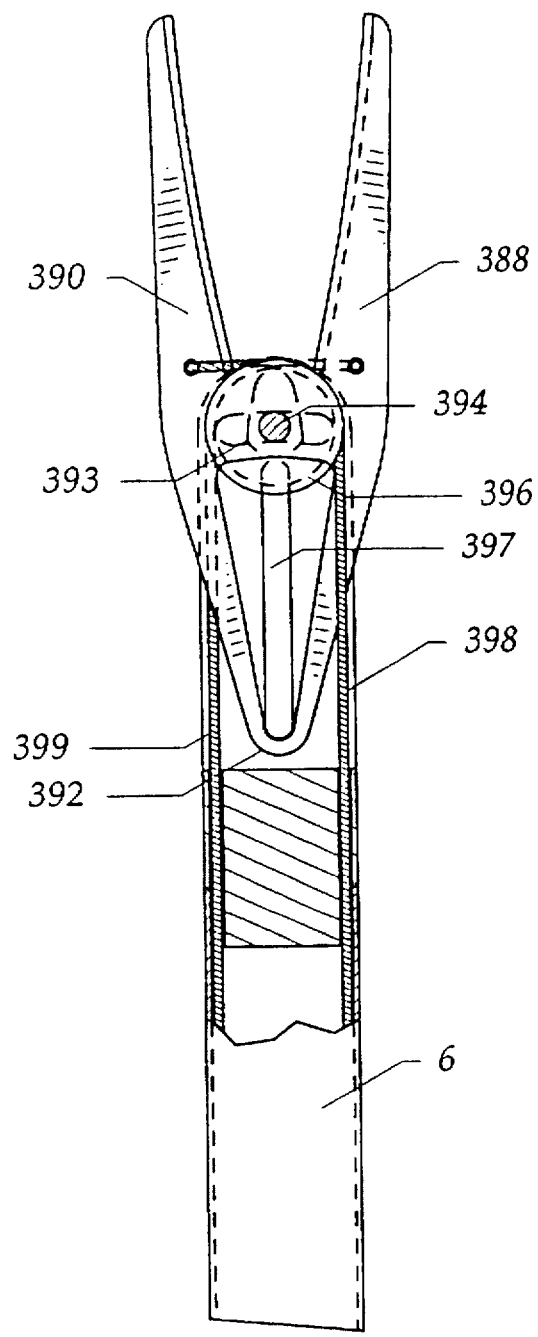
FIG. 32A is an elevational view of the end effector assembly of another form of the invention, partially in section, and with parts broken away for clarity.
Figure 32B:
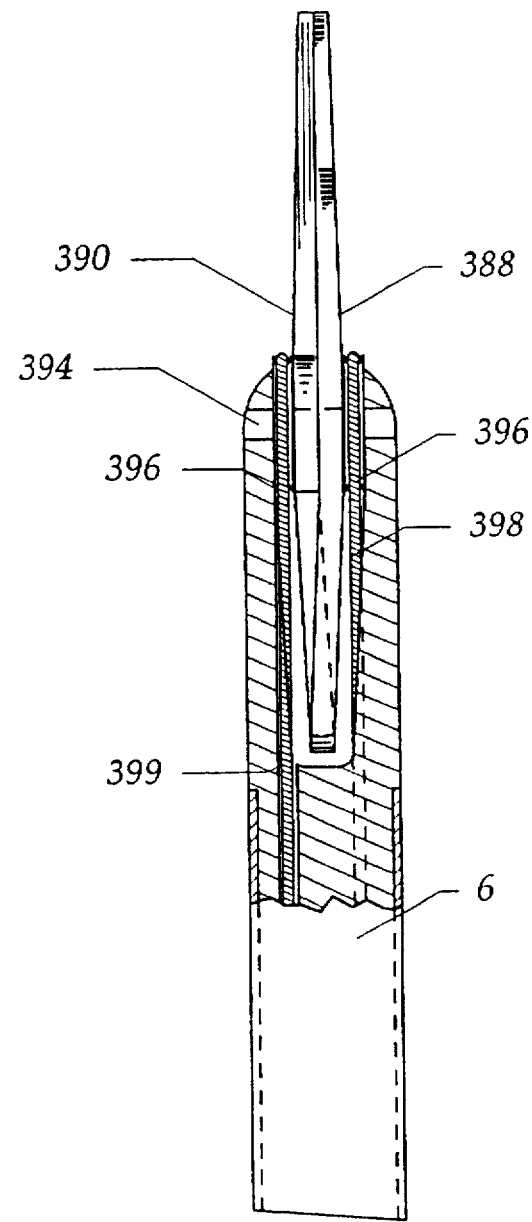
FIG. 32B is an elevational side view of the distal end of the form of the invention shown in FIG. 32A, partially in section, and with parts broken away for clarity.
Figure 32C:
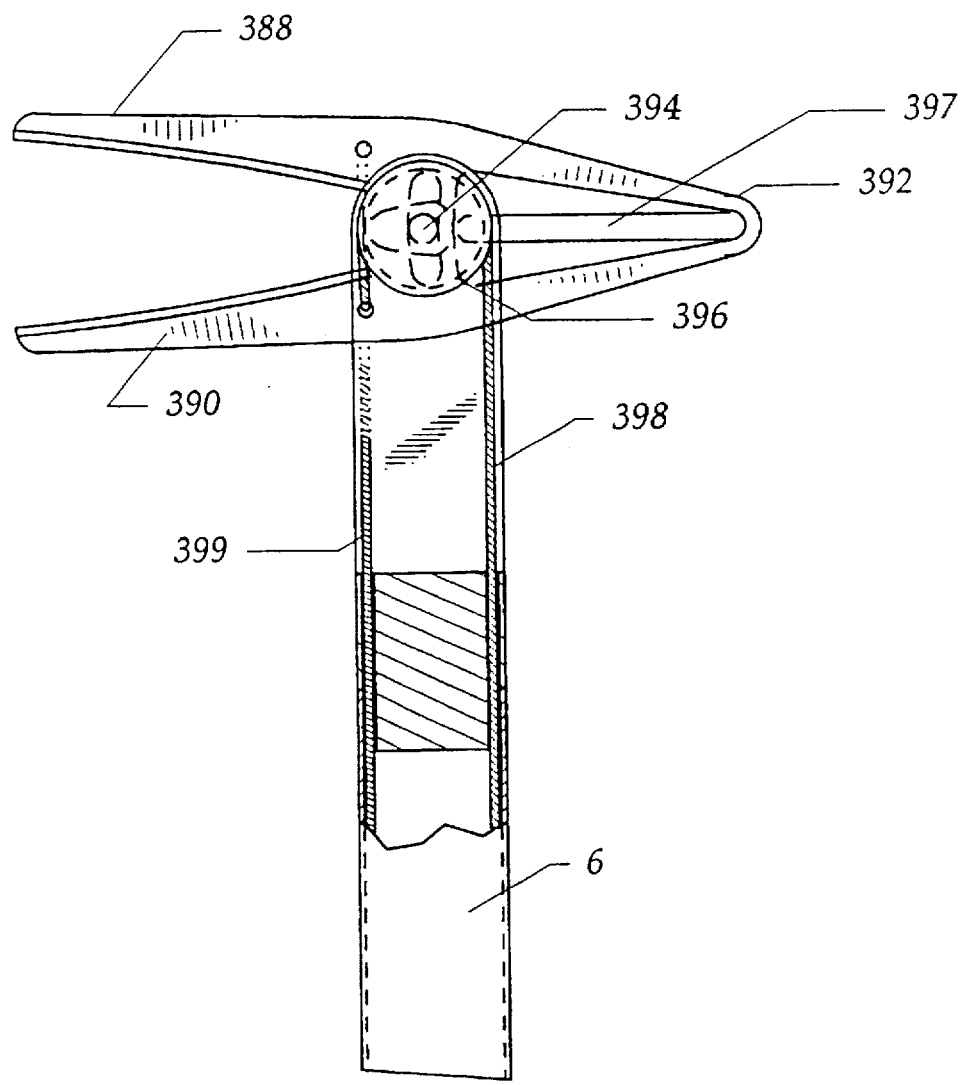
FIG. 32C is a view similar to that of FIG. 32A, depicting the pivoting movement of the end effector.

FIGS. 32A–C shows an alternative scissor-like tip embodiment which offers the advantages similar to those provided by the scissor-like design shown in FIG. 27A–C, however with fewer parts. FIG. 32A shows two end effector pieces 388, 390 which are ground to shear against one another. They are biased into the open position (FIG. 32A) by an integral spring 392 which connects the end effector pieces 388, 390 together. Each of the end effector pieces 388, 390 has a curved slot 393 through which pin 394 passes. The end effector pieces or jaws 388, 390 are located by pulley 396 and its "tail" 397 which protrudes in the proximal direction into the bend of the spring 392. The pulley 396 and "tail" 397 rotate together around pin 394 fixed in the end of the tubular barrel 6. This rotation causes pivoting of the end effector piece assembly around pin 394. Cord 398 wraps around the pulley 396 on one side of the pair of end effector pieces 388, 390 and attaches to end effector piece 388 on the opposite side. Similarly, another cord 399 runs in the opposite direction around the other pulley (396 in FIG. 32B) and attaches to the opposite end effector piece 390. Just as illustrated in FIG. 27, pulling on one cord while releasing the other causes rotation of the end effector pieces 388, 390 in that direction. FIG. 32C shows the end effector pieces 388, 390 rotated 90° (cord 399, the far cord, is hidden where it attaches to end effector piece 388). Pulling on both cords 398, 399 simultaneously causes closure of the end effector pieces 388, 390 and generates a cutting or shearing action. The advantage of this design is that the spring 392 biasing the end effector pieces 388, 390 open is an integral part of the end effector pieces 388, 390 and, thus, there are only two moving parts (excluding the cords 398, 399) in this embodiment of the end effector.

Another variation of the present handle and operating mechanism embodiment of the present invention includes a third servo motor which automatically opens and closes the end effector tip 8, as well as providing automatic powered functioning such as vibration. In this embodiment, each of the two racks 32, 34 of the end effector 8 (see FIGS. 2A–E) might be attached respectively to each of the two nuts 332, 334 (shown in FIG. 28A–D). The additional servo motor would twist the threaded shaft 336 causing opening and closing of the end effector pieces. The existing motor for pivoting would slide the entire shaft 336, moving both racks together, causing pivoting of the end effector. Each of the motors would be controlled by the microprocessor 120 described above.

Referring back to FIG. 30A, the third motor, gearbox, and gearing mechanism engage the collar 362 which is threaded on its outer, generally cylindrical surface and meshes with a complementary threaded gear (not shown). The gear is driven by a pinion operably coupled to an augmented motor and gearbox drive assembly. Driving the gear in one direction, causes the retraction of the collar 362 and shaft 336, closing the end effector tip 8. Driving the gear in the opposite direction moves the collar 362 in the distal direction, pushing the shaft 336 and opening the end effector pieces.

A variable position switch provides for continuous control of the motor. Although the trigger 2 is substantially the same as that depicted in FIG. 29A, in this embodiment it is basically a proportional switch biased in the distal direction. One position, a fully released or open position, corresponds to a control signal sent to the microprocessor to move the motor until the end effector tip 8 is fully open and held open. Another position, fully closed, the trigger's proximal position, provides a signal to the microprocessor to operate the motor to close the end effector 8 and hold it closed. Intermediate positions map trigger positions to correspond to end effector positions. Additionally, the trigger may be adapted to be movable vertically to provide a "lock-out" feature, immobilizing the end effector 8 in any position.

The operational options and parameters of the instrument of the present invention are increased by incorporating the electrical motors and control devices described above. Controlling the additional motors and the additional functions provided by the motors, such as vibration or oscillation of the end effector tip, is facilitated by using a microprocessor 120. This is particularly true when it is desired to include electronically controlled reciprocating movement of the end effector, vibration of the end effector tip, or another complex movement or motion involving coordinated actuation. Additionally, force feedback control in one or more directions or dimensions may be a desired attribute. For example, the harder the user pushes on the control button or trigger, the greater force with which the end effector tip closes and opens. Similarly, the harder the user pushes on a switch, the more rapidly the end effector closes or opens. Because of its flexibility, and dedicated control functionality, a microprocessor is particularly well-suited to achieve control of the servo motors for applications such as these. In any of the embodiments disclosed herein, microprocessor 120 may be used to monitor both voltage and current through the drive motors, as well as monitoring and regulating speeds, motor temperatures, and battery charge states.

The instrument of the present invention is designed for endoscopic, particularly laparoscopic, use. However, there are many other applications for this invention. For example, the interchangeable tips and operating linkages of the present invention may be incorporated into surgical instruments such as needle holders, staplers, lasers, atherectomy devices, or endoscopes. An electro-cautery feature has been added to the preferred embodiment of the present invention. Additionally, a chip camera could be added to the end effector tip, particularly for the placement of stints and stint graft combinations.

While specific embodiments of the present invention have been disclosed and described, it will be understood by those skilled in the art that various changes in form and detail may be made without departing from the spirit and scope of the invention.

What is claimed is:

1. A surgical instrument for use in endoscopy comprising:
 a tubular member comprising a proximal portion and a distal portion, the two portions having coupling means for attaching and detaching the distal portion to and from the proximal portion;
 an end effector comprising a first piece and a second piece, each piece being pivotally attached directly to a distal end of the distal portion of the tubular member;
 linkage extending through the tubular member, the linkage comprising a first elongated member and a second elongated member, each elongated member comprising a proximal section and a distal section, each of the distal sections being operably coupled at their distal end to one of the end effector pieces, each of the elongated member sections having mating means for attaching and detaching the respective distal section to and from its respective proximal section, the tubular member coupling means and elongated member mating means thereby allowing for detachment and replacement of an assembly comprising the end effector from and to the remainder of the surgical instrument; and
 a handle attached to the proximal end of the proximal portion of the tubular member, the handle comprising:
  a first control means for causing translational movement of the first elongated member relative to the second elongated member, thereby causing the end effector piece coupled to the first elongated member to pivot relative to the other end effector piece; and a second control means independent of the first control means, the second control means for causing relative translational movement between the tubular member and both the first and second elongated members without significant relative translational movement between the first and second elongated members, thereby causing the first and second end effector pieces to pivot simultaneously in the same direction.

2. The surgical instrument of claim 1, wherein:

the distal section of the first elongated member has a first rack disposed at its distal end;

the distal section of the second elongated member has a second rack disposed at its distal end;

the first end effector piece has a first gear matable with the first rack; and the second end effector piece has a second gear matable with the second rack.

3. The surgical instrument of claim 2, wherein:

the simultaneous pivoting of the two end effector pieces away from the longitudinal axis of the tubular member is accomplished by moving the first and second control members simultaneously in the distal direction;

the simultaneous pivoting of the two end effector pieces toward the longitudinal axis of the tubular member is accomplished by moving the first and second elongated members simultaneously in the proximal direction; and the pivoting of one end effector piece relative to the other end effector piece is accomplished by moving the first elongated member relative to the second elongated member.

4. The surgical instrument of claim 1 wherein:

the first and second elongated members are concentric with one another and are concentric with, and internal to, the tubular member;

the tubular member coupling means comprises a twistlock fitting lockable and unlockable upon the rotation of the proximal portion of the tubular member relative to the distal portion of the tubular member; and each of the elongated member mating means comprises a twistlock fitting lockable and unlockable upon the rotation of the respective proximal section relative to the respective distal section.

5. The surgical instrument of claim 4 wherein:

the coupling of the proximal and distal portions of the tubular member is achieved by rotating, in a given direction, the proximal portion relative to the distal portion; and the mating of the elongated member proximal sections with their respective distal sections is achieved by rotating, in the opposite direction of the given direction, each of the proximal sections relative to their respective distal sections.

6. The surgical instrument of claim 5 wherein:

the proximal portion of the tubular member can be rotated independent of the proximal sections of the first and second elongated members; and each of the elongated member distal sections is constrained to rotate with the distal portion of the tubular member, such that when the tubular member proximal portion is rotated so as to couple the proximal and distal portions of the tubular member with one another, continued rotation of the tubular member proximal portion induces the rotation of each of the elongated member distal sections and thus allows each of the elongated member distal sections to be mated with its respective proximal section.

7. The surgical instrument of claim 6 wherein the handle further comprises:

means for rotating the proximal portion of the tubular member; and means for restraining the rotation of the proximal sections of each elongated member while the proximal portion of the tubular member is being rotated.

8. The surgical instrument of claim 4 wherein each of all twistlock fittings are of bayonet-type design.

9. The surgical instrument of claim 8 wherein the slots of the bayonet fittings are tapered to facilitate connection and to minimize looseness in the connection.

10. The surgical instrument of claim 1, wherein the end effector is a scissors.

11. The surgical instrument of claim 1, wherein the end effector is a grasper.

12. The surgical instrument according to claim 1 wherein:

the first and second elongated members each have on a proximal end of their proximal sections a threaded portion; and the handle further comprises:

a first screw rotatably mounted in the handle, the first screw for receiving the threaded portion of the first elongated member; and a second screw operably coupled to the first screw for rotational movement therewith and movable axially by movement of the first control means.

13. The surgical instrument of claim 12 wherein the first and second control means are actuated by hand.

14. The surgical instrument of claim 1 wherein:

the first control means comprises a trigger;

the second control means comprises a slide operator; and the handle further comprises a third control means operably connected to the tubular member, the third control means for rotating the tubular member and attached end effector and comprising a rotatable knob, the rotation of the tubular member and end effector being about the axis of the tubular member and relative to the handle.

15. The surgical instrument of claim 1 wherein:

the first control means comprises a trigger;

the handle further comprises a third control means operably connected to the tubular member, the third control means for rotating the tubular member and attached end effector about the longitudinal axis of the tubular member and relative to the handle; and the second and third control means comprise a touchsensitive switch operator for controlling the rotation and the simultaneous pivoting of both pieces of the end effector.

16. The surgical instrument of claim 15 wherein the rotation and the simultaneous pivoting of both pieces of the end effector are motor-driven.

17. The surgical instrument of claim 15 wherein the second and third control means include a microprocessor.

18. The surgical instrument of claim 17 wherein the microprocessor is part of an electrical circuit including drive motors connected to and controlled by the microprocessor.

19. The surgical instrument of claim 18 wherein the first and second control means uses stored electrical energy in the form of a battery.

20. The surgical instrument of claim 1 further comprising an electrocautery cord so as to provide a conduction path through the handle and the tubular member to the end effector.

21. The surgical instrument of claim 1 wherein the handle further comprises a rack and pinion mechanism provided for translating the elongated members within the tubular member.

22. The surgical instrument of claim 21 wherein the rack and pinion mechanism comprises:

a pinion attached to the proximal end of each elongated member;

a first rack fixed in the handle and engaging the pinion of one of the elongated members;

a second rack movable relative to the first rack and engaging the pinions of both elongated members; and a third rack movable relative to the first rack and engaging the pinion of the elongated member not engaged by the first rack.

23. The surgical instrument of claim 22 wherein:

the second control means moves the second rack, thereby translating both elongated members and pivoting both end effector pieces simultaneously in the same direction; and the first control means moves the third rack, thereby translating one elongated member relative to the other resulting in the pivoting of one end effector piece relative to the other.

24. The surgical instrument of claim 23 wherein:

the first control means comprises a trigger for moving the third rack; and the second control means comprises a slide operator for moving the second rack.

25. The surgical instrument of claim 1 wherein the second control means comprises means for translating the tubular member relative to the first and second elongated members.

26. The surgical instrument of claim 25 wherein the tubular member translating means comprises:

a hollow screw disposed around, and fixably attached to, the tubular member near the proximal end of the tubular member; and a rotatable pivot knob disposed around the hollow screw, the pivot knob having internal threads matable with the threads of the hollow screw, whereby manual rotation of the pivot knob causes longitudinal movement of the tubular member relative to the first and second elongated members and thereby causes the end effector to pivot.

27. The surgical instrument of claim 26 wherein the first control means comprises a lever member attached to the first elongated member such that manual operation of the lever member causes the first elongated member to move longitudinally relative to the second elongated member, thereby causing the end effector piece coupled to the first elongated member to move relative the other end effector piece.

28. The surgical instrument of claim 27 further comprising a rotation knob disposed around, and rotatable with and around, the tubular member, the rotation knob attached to the tubular member and the first and second elongated members so as to constrain the tubular member to rotate with the rotation knob yet to allow the longitudinal movement of the tubular member and the first elongated member, whereby manual rotation of the rotation knob causes rotation of the end effector about the longitudinal axis of the tubular member.

29. The surgical instrument of claim 1 wherein:

the handle further comprises a rack-and-pinion mechanism for translating the elongated members within the tubular member, the rack-and-pinion mechanism comprising:

a first pinion attached to the proximal end of the first elongated member;

a second pinion attached to the proximal end of the second elongated member;

a pivot rack slidable longitudinally within the handle and having teeth that engage the teeth of the first and of the second pinions; and at least one opposed rack within the handle, the at least one opposed rack having teeth which engage the teeth of the pinion at the side opposite that side which the pivot rack engages; and the second control means comprises a slide operator operably attached to the pivot rack, whereby the manual operation of the slide operator causes the pivot rack to move longitudinally thereby causing the first and second elongated members attached to the pinions to move longitudinally and thereby causing the end effector to pivot.

30. The surgical instrument of claim 29 wherein:

the at least one opposed rack comprises:

a stationary rack whose teeth engage either the first or the second pinion;

a longitudinally slidable operator rack whose teeth engage the pinion not engaged by the stationary rack; and the first control means comprises a trigger attached to the operator rack, whereby the manual operation of the trigger causes the operator rack to move longitudinally thereby causing the associated elongated member likewise to move longitudinally and thereby causing one of the end effector pieces to move relative to the other piece.

31. The surgical instrument of claim 30 further comprising a rotation knob disposed around, and rotatable with and around, the tubular member, whereby the manual rotation of the rotation knob causes the rotation of the end effector.

32. In a surgical instrument for use in endoscopy comprising a tubular member having a proximal end and a distal end; an end effector comprising a first piece and a second piece, each piece being pivotally attached directly to the distal end of the tubular member; linkage extending through the tubular member, the linkage comprising a first elongated member operably connected to the first end effector piece, the linkage further comprising a second elongated member operably connected to the second end effector piece; and a handle attached to the proximal end of the tubular member, the handle comprising a first control means for causing translational movement of the first elongated member relative to the second elongated member, thereby causing the end effector piece operably coupled to the first elongated member to pivot relative to the other end effector piece, the handle further comprising a second control means independent of the first control means, the second control means for causing relative translational movement between the tubular member and both the first and second elongated members without significant relative translational movement between the first and second elongated members, thereby causing the first and second end effector pieces to pivot simultaneously in the same direction; an end effector detachment means wherein:

the tubular member comprises a proximal portion and a distal portion, the end effector being pivotally attached to the distal end of the distal portion, the two portions having coupling means for attaching and detaching the proximal and distal portions; and each of the first and second elongated members comprises a proximal section and a distal section, the end effector being operably coupled to the distal end of the distal sections, each of the sections having mating means for attaching and detaching each of the proximal sections to its respective distal section, the tubular member coupling means and first and second elongated member mating means thereby allowing for detachment and replacement of an assembly comprising the end effector from and to the remainder of the surgical instrument.

33. The end effector detachment means of claim 32 wherein:

the first and second elongated members are concentric with one another and are concentric with, and internal to, the tubular member;

the tubular member coupling means comprises a twistlock fitting lockable and unlockable upon the rotation of the proximal portion of the tubular member relative to the distal portion of the tubular member; and each of the elongated member mating means comprises a twistlock fitting lockable and unlockable upon the rotation of the respective proximal section relative to the respective distal section.

34. The end effector detachment means of claim 33 wherein:

the coupling of the proximal and distal portions of the tubular member is achieved by rotating, in a given direction, the proximal portion relative to the distal portion; and the mating of the elongated member proximal sections with their respective distal sections is achieved by rotating, in the opposite direction of the given direction, each of the proximal sections relative to their respective distal sections.

35. The end effector detachment means of claim 34 wherein:

the proximal portion of the tubular member can be rotated independent of the proximal sections of the first and second elongated members; and each of the elongated member distal sections is constrained to rotate with the distal portion of the tubular member, such that when the tubular member proximal portion is rotated so as to couple the proximal and distal portions of the tubular member with one another, continued rotation of the tubular member proximal portion induces the rotation of each of the elongated member distal sections and thus allows each of the elongated member distal sections to be mated with its respective proximal section.

36. The end effector detachment means of claim 35 wherein the handle further comprises:

means for rotating the proximal portion of the tubular member; and means for restraining the rotation of the proximal sections of each elongated member while the proximal portion of the tubular member is being rotated.

37. The end effector detachment means of claim 33 wherein each of all twistlock fittings are of bayonet-type design.

38. The end effector detachment means of claim 37 wherein the slots of the bayonet fittings are tapered to facilitate connection and to minimize looseness in the connection.

* * * * *